US007482322B2

(12) United States Patent
Koga et al.

(10) Patent No.: US 7,482,322 B2
(45) Date of Patent: Jan. 27, 2009

(54) PLEXIN FAMILY-LIKE POLYPEPTIDE, AND USES THEREOF

(75) Inventors: Hisashi Koga, Kisarazu (JP); Osamu Ohara, Kisarazu (JP); Haruhiko Koseki, Yokohama (JP); Mitsuhiro Okada, Kobe (JP); Akiyoshi Uemura, Kobe (JP); Hiroki Arakawa, Sapporo (JP); Mitsuhiro Tada, Sapporo (JP)

(73) Assignee: Kazusa DNA Research Institute Foundation, Kisarazu-shi (JP)

( * ) Notice: Subject to any disclaimer, the term of this patent is extended or adjusted under 35 U.S.C. 154(b) by 0 days.

(21) Appl. No.: 10/573,262

(22) PCT Filed: Oct. 28, 2004

(86) PCT No.: PCT/JP2004/015997

§ 371 (c)(1),
(2), (4) Date: Dec. 4, 2006

(87) PCT Pub. No.: WO2005/056791

PCT Pub. Date: Jun. 23, 2005

(65) Prior Publication Data

US 2007/0212365 A1 Sep. 13, 2007

(30) Foreign Application Priority Data

Oct. 30, 2003 (JP) ............................. 2003-371040
Aug. 5, 2004 (JP) ............................. 2004-229871

(51) Int. Cl.
*A61K 38/16* (2006.01)
*A61K 38/00* (2006.01)
*C07K 14/435* (2006.01)
*C07K 14/00* (2006.01)

(52) U.S. Cl. .............................. 514/12; 514/2; 530/350

(58) Field of Classification Search ........................ None
See application file for complete search history.

(56) References Cited

U.S. PATENT DOCUMENTS

2002/0009789 A1   1/2002   Hanyu et al.

FOREIGN PATENT DOCUMENTS

WO   WO-01/14420 A2   3/2001
WO   WO-01/57188 A2   8/2001
WO   WO-02/081745 A2   10/2002

OTHER PUBLICATIONS

Van der Zwaag et al. (2002). PLEXIN-D1, a novel plexin family member, is expressed in vascular endothelium and the central nervous system during mouse embryogenesis. Developmental Dynamics. 225:336-343.*
Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Skolnick et al. (2000). From genes to protein structure and function: novel applications of computational approaches in the genomic era. Trends in Biotechnology. 18:34-39.*
Palù et al. (1999). In pursuit of new developments for gene therapy. Journal of Biotechnology. 68:1-13.*
Phillips, A.J. (2001). The challenge of gene therapy and DNA delivery. Journal of Pharmacy and Pharmacology. 53:1169-1174.*
Wang et al. (1999). Rapid analysis of gene expression (RAGE) facilitates universal expression profiling. Nucleic Acds Research. 27(23):4609-4618.*
Kaufman et al. (1999). Transgenic analysis of a 100-kb human B-globulin cluster-containing DNA fragment propagated as a bacterial artificial chromosome. Blood. 94(9):3178-3184.*
Wigley et al. (1994). Site-specific transgene insertion: an approach. Reprod. Fertil. Dev. 6:585-588.*
Accession No. Q68HV1. Duke-Cohan et al. Oct. 11, 2004.*
Accession No. AY688678. Duke-Cohan et al. Aug. 21, 2004.*
Okazaki et al., DNA Res., Aug. 2003, 10(4), pp. 167-180, Accession: AK129175.

* cited by examiner

*Primary Examiner*—Christine J Saoud
*Assistant Examiner*—Jon M Lockard
(74) *Attorney, Agent, or Firm*—Birch, Stewart, Kolasch & Birch, LLP.

(57) ABSTRACT

The present invention is directed to a novel plexin family like DNA, a gene containing the DNA, novel polypeptide encoded by the DNA, a recombinant protein containing the polypeptide or heterologous polypeptide sequences, antibodies which bind to the polypeptides, methods for producing the polypeptides of the present invention. Conditions that can be diagnosed, screened, prevented, or treated by the compositions herein include prophylactic, angiogenesis and conservation of functions in various organs, angiogenesis at the time of tumor and regeneration of various organs, proliferation, differentiation and preservation of function of the cells in various organs, aging, and dysfunction of the present invention.

5 Claims, 9 Drawing Sheets

VESSEL

Fig.3A1
Fig.3A2

Fig.4B
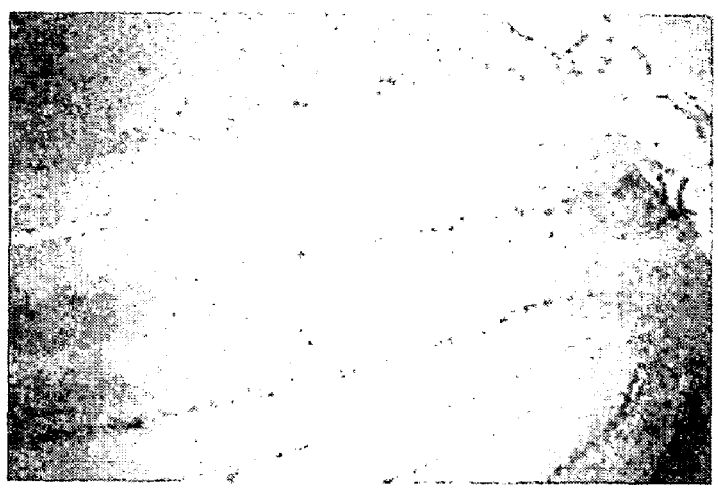
Fig.4C
Fig.5

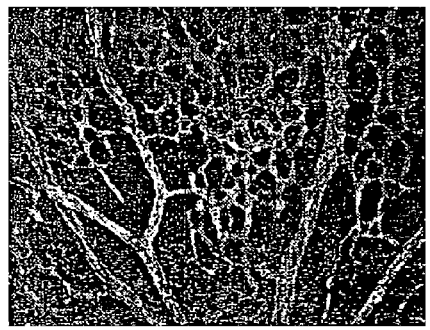
Fc
Fig.9A                    Fig.9B
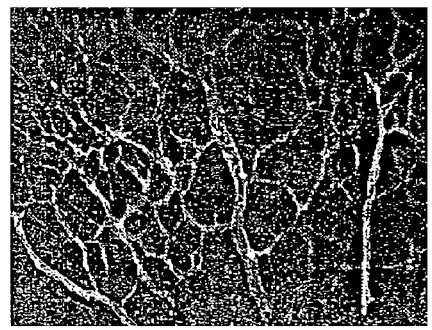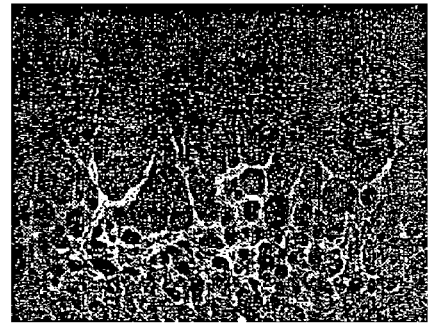
mKIAA0620
EXTRA
MEMBRANE
SEGMENT -Fc
Fig.9C                    Fig.9D
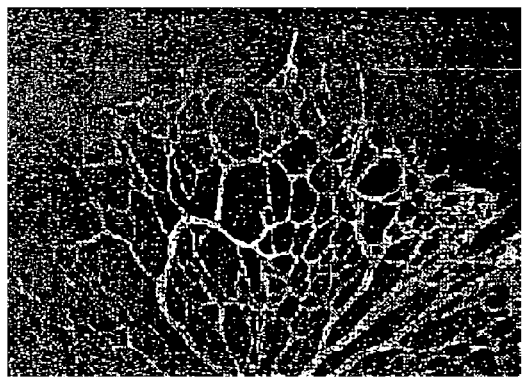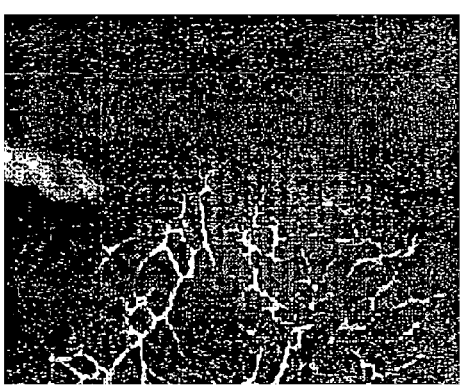
Fc                        mKIAA0620 EXTRA MEMBRANE
                          SEGMENT -Fc
Fig.10A                   Fig.10B

SEQUENCE LISTING

```
<160> NUMBER OF SEQ ID NOS: 24

<210> SEQ ID NO 1
<211> LENGTH: 1746
<212> TYPE: PRT
<213> ORGANISM: mouse

<400> SEQUENCE: 1

Ser Met Leu Asn Val Ala Ala Asn His Pro Asn Ala Ser Thr Val Gly
1               5                   10                  15

Leu Val Leu Pro Pro Thr Ser Gly Thr Gly Gly Ser Arg Leu Leu Val
            20                  25                  30

Gly Ala Thr Tyr Thr Gly Phe Gly Ser Ala Phe Phe Pro Arg Asn Arg
        35                  40                  45

Ser Leu Glu Asp His Arg Phe Glu Asn Thr Pro Glu Ile Ala Ile Arg
    50                  55                  60

Ser Leu Asp Ala Arg Gly Asp Leu Ala Lys Leu Phe Thr Phe Asp Leu
65                  70                  75                  80

Asn Pro Ser Asp Asp Asn Ile Leu Lys Ile Lys Gln Gly Ala Lys Glu
                85                  90                  95

Gln His Lys Leu Gly Phe Val Arg Ala Phe Leu His Pro Ala Val Pro
            100                 105                 110

Pro His Ser Ala Gln Pro Tyr Ala Tyr Leu Ala Leu Asn Ser Glu Ala
        115                 120                 125

Arg Ala Gly Asp Lys Asp Ser Gln Ala Arg Ser Leu Leu Ala Arg Ile
    130                 135                 140

Cys Leu Pro Arg Gly Ala Gly Gly Asp Ala Lys Lys Leu Thr Glu Ser
145                 150                 155                 160

Tyr Ile Gln Leu Gly Leu Gln Cys Ala Gly Gly Ala Gly Arg Gly Asp
                165                 170                 175

Leu Tyr Ser Arg Leu Val Ser Val Phe Pro Ala Arg Glu Gln Phe Phe
```

-continued

```
                180                 185                 190
Ala Val Phe Glu Arg Pro Gln Gly Ala Pro Gly Ala Arg Asn Ala Pro
            195                 200                 205
Ala Ala Leu Cys Ala Phe Arg Phe Asp Asp Val Gln Ala Ala Ile Arg
            210                 215                 220
Ala Ala Arg Thr Ala Cys Phe Val Glu Pro Ala Pro Asp Val Val Ala
225                 230                 235                 240
Val Leu Asp Ser Val Val Gln Gly Thr Gly Pro Ala Cys Glu Ser Lys
                245                 250                 255
Arg Asn Ile Gln Leu Gln Pro Glu Gln Leu Asp Cys Gly Ala Ala His
            260                 265                 270
Leu Gln His Pro Leu Thr Ile Leu Gln Pro Leu Arg Ala Ser Pro Val
            275                 280                 285
Phe Arg Ala Pro Gly Leu Thr Ala Val Ala Val Ala Ser Ala Asn Asn
            290                 295                 300
Tyr Thr Ala Val Phe Leu Gly Thr Ala Thr Gly Arg Leu Leu Lys Ile
305                 310                 315                 320
Ser Leu Asn Glu Ser Met Gln Val Val Ser Arg Arg Val Leu Thr Val
                325                 330                 335
Ala Tyr Gly Glu Pro Val His His Val Met Gln Phe Asp Pro Met Asp
            340                 345                 350
Pro Gly Tyr Leu Tyr Leu Met Thr Ser His Gln Met Ala Arg Val Lys
            355                 360                 365
Val Ala Ala Cys Glu Val His Ser Thr Cys Gly Asp Cys Val Gly Ala
            370                 375                 380
Ala Asp Ala Tyr Cys Gly Trp Cys Thr Leu Glu Thr Arg Cys Thr Leu
385                 390                 395                 400
Gln Gln Asp Cys Thr Asn Ser Ser Gln Pro His Phe Trp Thr Ser Ala
                405                 410                 415
Ser Glu Gly Pro Ser Arg Cys Pro Ala Met Thr Val Leu Pro Ser Glu
            420                 425                 430
Ile Asp Val His Arg Asp Tyr Thr Gly Met Ile Leu Gln Ile Ser Gly
            435                 440                 445
Ser Leu Pro Ser Leu Ser Gly Met Glu Met Ala Cys Asp Tyr Gly Asn
            450                 455                 460
Gly Val Arg Thr Val Ala Arg Val Pro Gly Pro Ala Tyr Asp His Gln
465                 470                 475                 480
Ile Ala Tyr Cys Asn Leu Leu Pro Arg Ala Gln Phe Pro Ser Phe Pro
                485                 490                 495
Ala Gly Gln Asp His Val Thr Val Glu Met Ser Val Arg Val Lys Gly
            500                 505                 510
His Asn Ile Val Ser Ala Asn Phe Thr Ile Tyr Asp Cys Ser Arg Ile
            515                 520                 525
Gly Gln Val Tyr Pro His Thr Ala Cys Thr Ser Cys Leu Ser Thr Gln
            530                 535                 540
Trp Pro Cys Ser Trp Cys Ile Gln Leu His Ser Cys Val Ser Asn Gln
545                 550                 555                 560
Ser Gln Cys Gln Asp Ser Pro Asn Pro Thr Ser Pro Gln Asp Cys Pro
                565                 570                 575
Gln Ile Leu Pro Ser Pro Leu Ala Pro Val Pro Thr Gly Gly Ser Gln
            580                 585                 590
Asp Ile Leu Val Pro Leu Thr Lys Ala Thr Phe Phe His Gly Ser Ser
            595                 600                 605
```

-continued

```
Leu Glu Cys Ser Phe Gly Leu Glu Glu Ser Phe Glu Ala Val Trp Ala
    610                 615                 620

Asn Asn Ser Leu Val Arg Cys Asn Gln Val Val Leu His Thr Thr Gln
625                 630                 635                 640

Lys Ser Gln Val Phe Pro Leu Ser Leu Lys Leu Lys Gly Pro Pro Asp
                    645                 650                 655

Arg Phe Leu Asp Ser Pro Asn Pro Met Thr Val Val Tyr Asn Cys
            660                 665                 670

Ala Met Gly Ser Pro Asp Cys Ser Gln Cys Leu Gly Arg Glu Asp Leu
            675                 680                 685

Gly His Leu Cys Val Trp Asn Asp Gly Cys Arg Leu Arg Gly Pro Leu
    690                 695                 700

Gln Pro Leu Pro Gly Thr Cys Pro Ala Pro Glu Ile Arg Ala Ile Glu
705                 710                 715                 720

Pro Leu Ser Gly Pro Leu Asp Gly Gly Thr Leu Leu Thr Ile Arg Gly
                    725                 730                 735

Arg Asn Leu Gly Arg Arg Leu Ser Asp Val Ala His Gly Val Trp Ile
            740                 745                 750

Gly Ser Val Ala Cys Glu Pro Leu Ala Asp Arg Tyr Thr Val Ser Glu
    755                 760                 765

Glu Ile Val Cys Ala Thr Gly Pro Ala Ala Gly Ala Phe Ser Asp Val
    770                 775                 780

Val Thr Val Asn Val Ser Lys Glu Gly Arg Ser Arg Glu Gln Phe Ser
785                 790                 795                 800

Tyr Val Leu Pro Thr Val His Ser Leu Glu Pro Ser Met Gly Pro Lys
                    805                 810                 815

Ala Gly Gly Thr Arg Ile Thr Ile His Gly Ser Asp Leu Asn Val Gly
            820                 825                 830

Ser Met Leu Gln Val Leu Val Asn Asp Thr Asp Pro Cys Thr Asp Leu
    835                 840                 845

Thr Arg Thr Ala Thr Ser Ile Thr Cys Thr Val Pro Gly Gly Thr Leu
    850                 855                 860

Pro Ser Pro Val Pro Val Cys Val Arg Phe Glu Ser Arg Gly Cys Val
865                 870                 875                 880

His Gly Asn Leu Thr Phe Trp Tyr Met Gln Asn Pro Val Ile Thr Ala
                    885                 890                 895

Ile Ser Pro Gly Arg Ser Pro Val Ser Gly Gly Arg Thr Ile Thr Val
            900                 905                 910

Ala Gly Glu Arg Phe His Met Val Gln Asn Val Ser Met Ala Val His
    915                 920                 925

His Ile Gly Arg Glu Pro Thr Phe Cys Lys Val Leu Asn Ser Thr Leu
    930                 935                 940

Ile Thr Cys Pro Ser Pro Gly Ala Leu Ser Asn Ala Ser Ala Pro Val
945                 950                 955                 960

Asp Phe Phe Ile Asn Gly Arg Ala Tyr Ala Asp Glu Ala Ala Glu Glu
                    965                 970                 975

Leu Leu Asp Pro Ala Glu Ala Gln Arg Gly Ser Arg Phe Arg Leu Asp
            980                 985                 990

Tyr Leu Pro Asn Pro Gln Phe Ser  Thr Ala Lys Arg Glu  Lys Trp Ile
        995                 1000                1005

Lys His  His Pro Gly Glu Pro  Leu Thr Leu Val Ile  His Lys Glu
    1010                1015                1020
```

-continued

```
Gln Asp Ser Leu Gly Leu Glu Ser His Glu Tyr His Ile Lys Ile
    1025                1030                1035

Gly Gln Val Ser Cys Asp Ile Gln Ile Ile Ser Asp Arg Val Ile
    1040                1045                1050

His Cys Ser Val Asn Glu Ser Leu Gly Thr Ala Glu Gly Gln Leu
    1055                1060                1065

Pro Ile Thr Ile Gln Val Gly Asn Phe Asn Gln Thr Ile Ala Thr
    1070                1075                1080

Leu Gln Leu Gly Gly Ser Glu Thr Ala Ile Val Val Ser Ile Val
    1085                1090                1095

Ile Cys Ser Val Leu Leu Leu Ser Val Val Ala Leu Phe Val
    1100                1105                1110

Phe Cys Thr Lys Ser Arg Arg Ala Glu Arg Tyr Trp Gln Lys Thr
    1115                1120                1125

Leu Leu Gln Met Glu Glu Met Glu Ser Gln Ile Arg Glu Glu Ile
    1130                1135                1140

Arg Lys Gly Phe Ala Glu Leu Gln Thr Asp Met Thr Asp Leu Thr
    1145                1150                1155

Lys Glu Leu Asn Arg Ser Gln Gly Ile Pro Phe Leu Glu Tyr Lys
    1160                1165                1170

His Phe Val Thr Arg Thr Phe Phe Pro Lys Cys Ser Ser Leu Tyr
    1175                1180                1185

Glu Glu Arg Tyr Val Leu Pro Ser Lys Thr Leu Asn Ser Gln Gly
    1190                1195                1200

Gly Ser Pro Pro Gln Glu Thr His Pro Leu Leu Gly Glu Trp Asn
    1205                1210                1215

Ile Pro Glu His Cys Arg Pro Ser Met Glu Glu Gly Ile Ser Leu
    1220                1225                1230

Phe Ser Ser Leu Leu Asn Asn Lys His Phe Leu Ile Val Phe Val
    1235                1240                1245

His Ala Leu Glu Gln Gln Lys Asp Phe Ala Val Arg Asp Arg Cys
    1250                1255                1260

Ser Leu Ala Ser Leu Leu Thr Ile Ala Leu His Gly Lys Leu Glu
    1265                1270                1275

Tyr Tyr Thr Ser Ile Met Lys Glu Leu Leu Val Asp Leu Ile Asp
    1280                1285                1290

Ala Ser Ala Ala Lys Asn Pro Lys Leu Met Leu Arg Arg Thr Glu
    1295                1300                1305

Ser Val Val Glu Lys Met Leu Thr Asn Trp Met Ser Ile Cys Met
    1310                1315                1320

Tyr Gly Cys Leu Arg Glu Thr Val Gly Glu Pro Phe Phe Leu Leu
    1325                1330                1335

Leu Cys Ala Ile Lys Gln Gln Ile Asn Lys Gly Ser Ile Asp Ala
    1340                1345                1350

Ile Thr Gly Lys Ala Arg Tyr Thr Leu Asn Glu Glu Trp Leu Leu
    1355                1360                1365

Arg Glu Asn Ile Glu Ala Lys Pro Arg Asn Leu Asn Val Ser Phe
    1370                1375                1380

Gln Gly Cys Gly Met Asp Ser Leu Ser Val Arg Ala Met Asp Thr
    1385                1390                1395

Asp Thr Leu Thr Gln Val Lys Glu Lys Ile Leu Glu Ala Phe Cys
    1400                1405                1410

Lys Asn Val Pro Tyr Ser Gln Trp Pro Arg Ala Glu Asp Val Asp
```

| | | | | | | | | | | |
|---|---|---|---|---|---|---|---|---|---|---|
| | 1415 | | | | 1420 | | | | 1425 | |

Leu Glu Trp Phe Ala Ser Ser Thr Gln Ser Tyr Val Leu Arg Asp
　　1430　　　　　　　　　　　1435　　　　　　　　　　1440

Leu Asp Asp Thr Ser Val Val Glu Asp Gly Arg Lys Lys Leu Asn
　　1445　　　　　　　　　　　1450　　　　　　　　　　1455

Thr Leu Ala His Tyr Lys Ile Pro Glu Gly Ala Ser Leu Ala Met
　　1460　　　　　　　　　　　1465　　　　　　　　　　1470

Ser Leu Thr Asp Lys Lys Asp Ser Thr Leu Gly Arg Val Lys Asp
　　1475　　　　　　　　　　　1480　　　　　　　　　　1485

Leu Asp Thr Glu Lys Tyr Phe His Leu Val Leu Pro Thr Asp Glu
　　1490　　　　　　　　　　　1495　　　　　　　　　　1500

Leu Val Glu Pro Lys Lys Ser His Arg Gln Ser His Arg Lys Lys
　　1505　　　　　　　　　　　1510　　　　　　　　　　1515

Val Leu Pro Glu Ile Tyr Leu Thr Arg Leu Leu Ser Thr Lys Gly
　　1520　　　　　　　　　　　1525　　　　　　　　　　1530

Thr Leu Gln Lys Phe Leu Asp Asp Leu Phe Lys Ala Ile Leu Ser
　　1535　　　　　　　　　　　1540　　　　　　　　　　1545

Ile Arg Glu Asp Lys Pro Pro Leu Ala Val Lys Tyr Phe Phe Asp
　　1550　　　　　　　　　　　1555　　　　　　　　　　1560

Phe Leu Glu Glu Gln Ala Glu Lys Arg Gly Ile Ser Asp Pro Asp
　　1565　　　　　　　　　　　1570　　　　　　　　　　1575

Thr Leu His Ile Trp Lys Thr Asn Ser Leu Pro Leu Arg Phe Trp
　　1580　　　　　　　　　　　1585　　　　　　　　　　1590

Val Asn Ile Leu Lys Asn Pro Gln Phe Val Phe Asp Ile Glu Lys
　　1595　　　　　　　　　　　1600　　　　　　　　　　1605

Thr Asp His Ile Asp Ala Cys Leu Ser Val Ile Ala Gln Ala Phe
　　1610　　　　　　　　　　　1615　　　　　　　　　　1620

Ile Asp Ala Cys Ser Ile Ser Asp Leu Gln Leu Gly Lys Asp Ser
　　1625　　　　　　　　　　　1630　　　　　　　　　　1635

Pro Thr Asn Lys Leu Leu Tyr Ala Lys Glu Ile Pro Glu Tyr Arg
　　1640　　　　　　　　　　　1645　　　　　　　　　　1650

Lys Thr Val Gln Arg Tyr Tyr Lys Gln Ile Gln Asp Met Thr Pro
　　1655　　　　　　　　　　　1660　　　　　　　　　　1665

Leu Ser Glu Gln Glu Met Asn Ala His Leu Ala Glu Glu Ser Arg
　　1670　　　　　　　　　　　1675　　　　　　　　　　1680

Lys Tyr Gln Asn Glu Phe Asn Thr Asn Val Ala Met Ala Glu Ile
　　1685　　　　　　　　　　　1690　　　　　　　　　　1695

Tyr Lys Tyr Ala Lys Arg Tyr Arg Pro Gln Ile Met Ala Ala Leu
　　1700　　　　　　　　　　　1705　　　　　　　　　　1710

Glu Ala Asn Pro Thr Ala Arg Arg Thr Gln Leu Gln His Lys Phe
　　1715　　　　　　　　　　　1720　　　　　　　　　　1725

Glu Gln Val Val Ala Leu Met Glu Asn Asn Ile Tyr Glu Cys Tyr
　　1730　　　　　　　　　　　1735　　　　　　　　　　1740

Ser Glu Ala
　　1745

<210> SEQ ID NO 2
<211> LENGTH: 6178
<212> TYPE: DNA
<213> ORGANISM: mouse

<400> SEQUENCE: 2
ccagcatgct caacgtggcc gccaaccacc caacgcgtc cactgtggga ctggtgctgc    60
cgcctacctc gggcaccggg ggcagccgtc tgctcgtggg cgccacgtac accggcttcg   120

-continued

```
gcagcgcttt cttcccgcgc aaccgtagcc tagaagacca ccgcttcgag aacacgcccg    180
agatcgctat ccgctccctg gacgcgcgtg gagacttggc caagctcttc accttcgacc    240
ttaacccgtc ggacgataac atcctgaaga tcaagcaggg cgccaaggag cagcacaagc    300
tgggcttcgt gcgtgccttc ttgcacccgg cggtgccacc gcacagcgcg cagccctacg    360
cgtacctggc gctcaacagc gaggcgcgtg cgggcgacaa ggacagccag gcgcgcagcc    420
tgctggcgcg catctgcctg ccccgcggcg cgggtggcga cgccaagaag ctcaccgagt    480
cctacatcca actgggcttg cagtgcgcgg gcggcgcggg ccgcggcgac tctacagcc     540 gcctcgtgtc ggttttcccc gcgcgcgagc agttcttcgc cgtcttcgag cggccccagg    600 gcgcccagg tgcccgcaac gccccggccg cgctttgcgc cttccgcttc gacgacgtgc     660
aggctgccat tcgtgcagcg cgcaccgcct gcttcgtgga gccggcgccc gacgtggtgg    720
cggtgttgga cagtgtggtg cagggcaccg gccggcctg cgagagcaag cgcaacatac     780
agctgcagcc ggagcaactg gattgcggag cggcccacct gcagcaccca ctgaccatcc    840
tgcagccgct gagggcatcg cccgtgttcc gtgctccagg gctcacggcc gtggctgtgg    900
ccagtgccaa caactacacg gccgtctttc tgggcaccgc cacagggagg ctcctcaaga    960
tcagcctgaa cgagagcatg caggtagtaa gcaggcgagt gctgactgta gcctatgggg    1020
agcctgtgca tcacgtcatg cagtttgacc ccatggatcc tggttaccta tacctgatga    1080
catcccacca gatggcccga gtgaaggtgg cagcgtgtga ggtacactcc acctgcgggg    1140
actgcgtggg tgcggccgat gcctactgtg gttggtgcac tctggagacc cggtgcacac    1200
tccagcagga ttgcaccaac tccagccagc cacatttctg gaccagtgcc agtgagggcc    1260
ccagccgctg ccctgccatg acagtactgc cctcggagat tgatgtgcac cgggactaca    1320
caggtatgat cttacagatc tcaggaagcc tgcccagcct cagcggcatg gagatggctt    1380
gtgactatgg aaatgcgtt cgaacggtgg cccgggtacc tggccctgcc tatgatcatc     1440
agattgccta ctgcaatctc ctgcccaggg cccagttttcc atcctttcct gctggccagg    1500
accacgtgac cgttgagatg tctgtaaggg tcaaaggaca caacattgtc tcagccaatt    1560
tcaccatcta cgactgcagc cgaattggac aagtctaccc ccatacagcc tgtaccagct    1620
gcctgtccac acagtggcct tgctcctggt gcatccagct gcattcatgt gtctccaacc    1680
agtctcagtg ccaggactcg ccaaaccca cgagtcctca ggactgtccc cagatcctgc      1740 cctcgccct agcgcccgtg cccacaggtg gctcccaaga catcctggtg cccctgacta      1800
aagccacctt cttccatggt tcctccctcg agtgcagctt tgggctggaa gagagctttg     1860
aggctgtatg ggcgaataac tcactggtcc gctgcaacca agtggtgctg cacacaaccc     1920
agaagagcca ggtatttcca ctgagtctga agctgaaggg gccgccagac cgattcctag     1980
acagccctaa ccccatgaca gttgtggtct acaactgtgc tatgggcagc cctgactgtt     2040
cccagtgcct gggccgtgag gacctgggtc acctctgtgt ttggaatgat ggctgtcgtc     2100
taagagggcc cctgcagcca ctccctggca cctgccagc ccctgaaatc cgagcgattg      2160
agcctctgag tggccccttg gacggtggga ctttgctgac catccgtggc aggaacttgg     2220
gccgtcggct cagtgatgtg gcacatggtg tgtggattgg cagtgtggcc tgtgaacccc     2280
tggctgacag atacaccgtt tcagaggaga tcgtgtgtgc cacagggcct gccgcagggg    2340
ccttctcaga cgtggtaacg gtgaacgtct ccaaggaagg caggtctcgg gaacagttct     2400
cctatgtgct gcccacggtc cactcactgg agccttccat gggcccaaag gccggggta    2460
```

```
caaggatcac cattcacggc agtgacctca acgtgggctc tatgctccag gtcctggtga   2520
atgacacgga cccctgcaca gatcttacgc gcacagccac cagcatcacc tgcactgtgc   2580
cagggggtac cctgccctct ccagtgcctg tgtgtgtgcg cttcgagagc cggggctgcg   2640
tgcacggaaa cctcaccttc tggtacatgc agaacccagt catcacagcc atcagcccag   2700
gccgcagccc tgtcagtggc ggcaggacca tcactgtggc tggcgaacgc ttccacatgg   2760
tgcagaatgt atcaatggct gtacaccaca ttggcccgga gcccacgttc tgcaaggttc   2820
tcaactccac actcatcacc tgcccatctc ctggagccct gagcaatgct tcggcgcctg   2880
tagacttctt catcaatggc cgggcatatg cagacgaggc agccgaggag ctgctggacc   2940
ctgcagaggc acagagggc agccggttcc gcctagacta cctccccaac ccacagttct   3000
ccacagccaa gagggagaag tggatcaaac atcacccagg agagccgctc accctcgtca   3060
tccataagga gcaagacagc ctggggctgg agagccatga gtaccacatc aagattggcc   3120
aggtgtcctg cgacatccag atcatctcag acagagtcat ccactgctca gtcaatgagt   3180
cgctgggcac ggctgaagga cagctgccca tcacaatcca ggtggggaac ttcaaccaga   3240
ccatcgccac actgcaactg gggggcagcg agacggccat tgtggtgtcc atcgtcatct   3300
gcagtgtcct gttgctgctg tctgtggttg ctctgttcgt cttctgcacc aagagccgcc   3360
gtgccgagcg ctactggcag aagaccctgc tgcagatgga agagatggag tctcagatcc   3420
gagaggagat ccgtaaaggc tttgcggagc tgcagacaga catgacggat ctcaccaagg   3480
agctgaaccg cagccaggc atccccttct tggagtacaa gcacttcgtg actcgaacct   3540
tcttccccaa gtgctcttcc ctctatgaag agcggtatgt gctgccctcg aagaccctca   3600
actcccaggg tggctcccg ccacaggaaa cccacccact gctgggagag tggaacatcc   3660
ctgaacactg tcggcccagc atggaggagg ggatcagcct gttctcctca ctgctcaaca   3720
acaagcactt cctcatcgtc ttcgtccatg ctctggagca gcagaaggac ttcgcagtgc   3780
gtgacaggtg cagcctggcg tccctgctga ccatcgcgct gcacggcaag ctggagtact   3840
atacgagcat catgaaggag ctgctcgtgg acctcatcga cgcctcggcg gccaagaacc   3900
ccaagctcat gttgcggcgc acggagtctg tggtggagaa gatgcttacc aactggatgt   3960
ccatctgcat gtacgctgc ctgagggaga cagtaggtga gccgttcttc ctgctgttgt   4020
gtgccatcaa gcagcagatc aacaaaggct ccatcgacgc catcacaggc aaagcccgct   4080
acacactcaa cgaggagtgg ctgctgaggg agaacattga ggccaagccc cggaacttga   4140
acgtgtcctt ccagggctgt gggatggact ccctcagcgt gcgggccatg gacaccgaca   4200
cgctgacgca ggtgaaggag aagatcctgg aagccttctg caagaacgtc cctactcac   4260 agtggccgcg ggcggaggac gtggaccttg aatggtttgc ctcgagtacc cagagctacg   4320
tcctccggga cctggatgac acatcagtgg tggaggacgg ccgtaagaaa ctgaacacac   4380
tggcccacta caagatacct gagggcgcct ccctagccat gagcctcaca gacaagaagg   4440
acagtaccct gggcagagtg aaagacttgg acacagaaaa gtatttccat tggtgctac   4500 ctacggatga gctggtagag cctaagaaat ccaccggca gagccaccgc aagaaagtat   4560
tgccagagat ctacctgacc cgcctgctgt ccaccaaggg cacgctgcag aagttcctag   4620
atgacctgtt caaggctatc ctgagcatcc gagaggacaa gccccgctg gctgtcaagt   4680 atttctttga cttcctagag aacaggcgg agaagagagg catctccgac cctgacaccc   4740
tgcatatctg gaagaccaac agccttcccc tgcgcttctg ggtgaacatc ttaaaaaatc   4800
cccagtttgt cttcgacata gagaagacgg accacatcga cgcctgcctg tctgtcatcg   4860
```

```
cacaggcctt catcgatgcc tgctccatct ctgacctgca gctgggcaag gactcaccca    4920
ccaacaagct tctgtacgcg aaggagatcc ctgagtaccg aagaccgta cagcgctatt     4980 ataaacagat ccaagacatg acgccgctca gcgagcagga aatgaacgca cacctggccg    5040
aggagtctcg gaaataccag aatgagttca acacaaacgt ggccatggct gagatttata   5100
aatatgctaa gaggtatcga ccacagatca tggctgccct ggaggccaac cccacagccc    5160
gcaggaccca gctacagcac aagtttgaac aggtggtggc tctgatggaa aacaatatct    5220
atgagtgtta cagcgaggcc tgatgcagaa gagtgaccag gagcttcggc cagggagacg    5280
gcgtgcaggc cacttggcct ccacttggtt tcttccccac atctctcact tgggctggga    5340
actgacagag gagcctgctg ggctaggagt gggggacact ggcctcttag tgcccggctg    5400
ccgagctctt ggccttgtcc cctggggcat ctctgtcccc tccacctgcc caagacccaa    5460
ctctaggatg aaggccttga atatcgatcg ctgccagtcc ctaataagac tttccctgcc    5520
aaccaggaca gcctggacca tgcctgcctg ttcactgttt caggctgctc agcacacatt    5580
gggagaggtg gccatatccc agaacactac ctcatccacc tggcagaggg aatttctgct    5640
tcagccacca agcagttgtc tgtgtccctc atccagaggg ggccttggcc accaacagtt    5700
ccaaaccagg tcagctgtta gccgtctcat tggccagtgg cagcatgggc agtgcccatt    5760
gcccacagaa cggtggagag aggggacag gctgggggtt cctggcccca ggaaagggag     5820
gaaggcgagg atgcagggct gtagctggac tactcagtct tcctggaagt gtttctaaag    5880
agcaccactt ttttttgttt tttgtttttt aagaaaaaaa aaactttat atattaaaac     5940 aaaaacttat gcaccaactg tgaatagctg ccgcttgtgc agatcccag gggctcccgg     6000 tgacacactg gaaatgactg ttccagggga cagaaaatac tcatctgtcc ccagcacagc    6060
ccccacccca cccccatag ctgctgagac tggctcacag cccaagggg ctgggctgga     6120 ggggaaggct gggactctct ggaacattct ttataataaa agcctgccgg gaaaacct     6178
```

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide forward primer

<400> SEQUENCE: 3
ccccggaact tgaacgtgtc                                                 20

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
    oligonucleotide reverse primer

<400> SEQUENCE: 4
ccacctgttc aaacttgtgc tg                                              22

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
    oligonucleotide reverse primer (GSP1)

<400> SEQUENCE: 5
aatcttgatg tggtactcat ggctctc                                    27

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide forward primer

<400> SEQUENCE: 6
aagctgctgg ggcggggaga tgggct                                     26

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide reverse primer (GSP2)

<400> SEQUENCE: 7
aatgttgtgt cctttgaccc ttac                                       24

<210> SEQ ID NO 8
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide forward primer

<400> SEQUENCE: 8
ttgtcgacac aagtttgtac aaaaaagcag gctctatggg ctgtgggcgt ggtctccacg    60
gagccgcccc cgggctgagc                                            80

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide reverse primer

<400> SEQUENCE: 9
aaatgtggct ggctggagtt ggt                                        23

<210> SEQ ID NO 10
<211> LENGTH: 753
<212> TYPE: DNA
<213> ORGANISM: mouse

<400> SEQUENCE: 10
gagatgggct gtgggcgtgg tctccacgga gccgcccccg ggctgagcgc ctcgccagag    60
tcgggccggg gcgccggggc cggggcggc aggcgcgggc aggaagcgcc tcgcggcccg   120
ggcccgcccc ccgcctctcg ccgctccga gctcccggct ccggccgcg ccgcgcccca   180 tgcactcgcc gcgccgcgca gccgcgctc gcctggatgg ctcgtcgcgc gcggggcggc   240
gcacccccta gcgccgggc cgcgcggcc gtcccttgc gtccgcgccc tcactcgcgg    300
ggccctggtc tgctgccgct gcctctgctg ctgctgctcg gggcggcacg ggccggcgcc   360

```
ctagagatcc agcgccgttt ccctcgccc acgcccacca acaacttcgc cctggacggc      420
acggcgggca ccgtgtactt ggcggcagtg aaccgcctgt accaactgtc gagtgccaac      480
ttgagcctgg aagccgaggc gaccgtgggt cccgtgccgg acagcccgct gtgtcacgcc      540
ccgcagctcc cgcaggcctc gtgcgagcac ccgcggcgcc tcacggacaa ctacaacaaa      600
atcctgcagt tggacccggg ccagggtctg gtggtcgcgt gcggctccat ctaccagggt      660
ctgtgccagc tgaggcgccg gggcaacatc tcagccctgg ccgtgagctt tccgcctgcc      720
gcgccgaccg cagaaccggt caccgtgttc ccc                                  753
```

```
<210> SEQ ID NO 11
<211> LENGTH: 251
<212> TYPE: PRT
<213> ORGANISM: mouse

<400> SEQUENCE: 11
```

```
Glu Met Gly Cys Gly Arg Gly Leu His Gly Ala Ala Pro Gly Leu Ser
 1               5                  10                  15

Ala Ser Pro Glu Ser Gly Arg Gly Ala Gly Ala Gly Gly Arg Arg
            20                  25                  30

Gly Gln Glu Ala Pro Arg Gly Pro Gly Pro Pro Ala Ser Arg Arg
        35                  40                  45

Leu Arg Ala Pro Gly Ser Arg Pro Arg Arg Ala Pro Cys Thr Arg Arg
 50                  55                  60

Ala Ala Gln Pro Ala Leu Ala Trp Met Ala Arg Arg Ala Ala Gly Gly
 65                  70                  75                  80

Ala Pro Pro Ser Ala Arg Ala Ala Ala Val Pro Leu Arg Pro Arg
                85                  90                  95

Pro His Ser Arg Gly Pro Gly Leu Leu Pro Leu Pro Leu Leu Leu Leu
                100                 105                 110

Leu Gly Ala Ala Arg Ala Gly Ala Leu Glu Ile Gln Arg Arg Phe Pro
            115                 120                 125

Ser Pro Thr Pro Thr Asn Asn Phe Ala Leu Asp Gly Thr Ala Gly Thr
130                 135                 140

Val Tyr Leu Ala Ala Val Asn Arg Leu Tyr Gln Leu Ser Ser Ala Asn
145                 150                 155                 160

Leu Ser Leu Glu Ala Glu Ala Thr Val Gly Pro Val Pro Asp Ser Pro
                165                 170                 175

Leu Cys His Ala Pro Gln Leu Pro Gln Ala Ser Cys Glu His Pro Arg
            180                 185                 190

Arg Leu Thr Asp Asn Tyr Asn Lys Ile Leu Gln Leu Asp Pro Gly Gln
        195                 200                 205

Gly Leu Val Val Ala Cys Gly Ser Ile Tyr Gln Gly Leu Cys Gln Leu
    210                 215                 220

Arg Arg Arg Gly Asn Ile Ser Ala Leu Ala Val Ser Phe Pro Pro Ala
225                 230                 235                 240

Ala Pro Thr Ala Glu Pro Val Thr Val Phe Pro
                245                 250
```

```
<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide forward primer
```

```
<400> SEQUENCE: 12
caccatgggc tgtgggcgtg gtct                                              24

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide reverse primer 1

<400> SEQUENCE: 13
tcaggcctcg ctgtaacact cataga                                            26

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide reverse primer 2

<400> SEQUENCE: 14
ggcctcgctg taacactcat aga                                               23

<210> SEQ ID NO 15
<211> LENGTH: 1997
<212> TYPE: PRT
<213> ORGANISM: mouse

<400> SEQUENCE: 15
```

Glu Met Gly Cys Gly Arg Gly Leu His Gly Ala Ala Pro Gly Leu Ser
1               5                   10                  15

Ala Ser Pro Glu Ser Gly Arg Gly Ala Gly Ala Gly Gly Arg Arg
            20                  25                  30

Gly Gln Glu Ala Pro Arg Gly Pro Gly Pro Pro Ala Ser Arg Arg
        35                  40                  45

Leu Arg Ala Pro Gly Ser Arg Pro Arg Arg Ala Pro Cys Thr Arg Arg
50                  55                  60

Ala Ala Gln Pro Ala Leu Ala Trp Met Ala Arg Arg Ala Ala Gly Gly
65                  70                  75                  80

Ala Pro Pro Ser Ala Arg Ala Ala Ala Val Pro Leu Arg Pro Arg
                85                  90                  95

Pro His Ser Arg Gly Pro Gly Leu Leu Pro Leu Pro Leu Leu Leu Leu
            100                 105                 110

Leu Gly Ala Ala Arg Ala Gly Ala Leu Glu Ile Gln Arg Arg Phe Pro
        115                 120                 125

Ser Pro Thr Pro Thr Asn Asn Phe Ala Leu Asp Gly Thr Ala Gly Thr
130                 135                 140

Val Tyr Leu Ala Ala Val Asn Arg Leu Tyr Gln Leu Ser Ser Ala Asn
145                 150                 155                 160

Leu Ser Leu Glu Ala Glu Ala Thr Val Gly Pro Val Pro Asp Ser Pro
                165                 170                 175

Leu Cys His Ala Pro Gln Leu Pro Gln Ala Ser Cys Glu His Pro Arg
            180                 185                 190

Arg Leu Thr Asp Asn Tyr Asn Lys Ile Leu Gln Leu Asp Pro Gly Gln
        195                 200                 205

Gly Leu Val Val Ala Cys Gly Ser Ile Tyr Gln Gly Leu Cys Gln Leu
    210                 215                 220

-continued

```
Arg Arg Arg Gly Asn Ile Ser Ala Leu Ala Val Ser Phe Pro Pro Ala
225                 230                 235                 240

Ala Pro Thr Ala Glu Pro Val Thr Val Phe Pro Ser Met Leu Asn Val
            245                 250                 255

Ala Ala Asn His Pro Asn Ala Ser Thr Val Gly Leu Val Leu Pro Pro
                260                 265                 270

Thr Ser Gly Thr Gly Gly Ser Arg Leu Leu Val Gly Ala Thr Tyr Thr
        275                 280                 285

Gly Phe Gly Ser Ala Phe Phe Pro Arg Asn Arg Ser Leu Glu Asp His
290                 295                 300

Arg Phe Glu Asn Thr Pro Glu Ile Ala Ile Arg Ser Leu Asp Ala Arg
305                 310                 315                 320

Gly Asp Leu Ala Lys Leu Phe Thr Phe Asp Leu Asn Pro Ser Asp Asp
                325                 330                 335

Asn Ile Leu Lys Ile Lys Gln Gly Ala Lys Glu Gln His Lys Leu Gly
                340                 345                 350

Phe Val Arg Ala Phe Leu His Pro Ala Val Pro Pro His Ser Ala Gln
        355                 360                 365

Pro Tyr Ala Tyr Leu Ala Leu Asn Ser Glu Ala Arg Ala Gly Asp Lys
370                 375                 380

Asp Ser Gln Ala Arg Ser Leu Leu Ala Arg Ile Cys Leu Pro Arg Gly
385                 390                 395                 400

Ala Gly Gly Asp Ala Lys Lys Leu Thr Glu Ser Tyr Ile Gln Leu Gly
                405                 410                 415

Leu Gln Cys Ala Gly Gly Ala Gly Arg Gly Asp Leu Tyr Ser Arg Leu
        420                 425                 430

Val Ser Val Phe Pro Ala Arg Glu Gln Phe Phe Ala Val Phe Glu Arg
            435                 440                 445

Pro Gln Gly Ala Pro Gly Ala Arg Asn Ala Pro Ala Ala Leu Cys Ala
        450                 455                 460

Phe Arg Phe Asp Asp Val Gln Ala Ala Ile Arg Ala Ala Arg Thr Ala
465                 470                 475                 480

Cys Phe Val Glu Pro Ala Pro Asp Val Val Ala Val Leu Asp Ser Val
            485                 490                 495

Val Gln Gly Thr Gly Pro Ala Cys Glu Ser Lys Arg Asn Ile Gln Leu
        500                 505                 510

Gln Pro Glu Gln Leu Asp Cys Gly Ala Ala His Leu Gln His Pro Leu
            515                 520                 525

Thr Ile Leu Gln Pro Leu Arg Ala Ser Pro Val Phe Arg Ala Pro Gly
530                 535                 540

Leu Thr Ala Val Ala Val Ala Ser Ala Asn Asn Tyr Thr Ala Val Phe
545                 550                 555                 560

Leu Gly Thr Ala Thr Gly Arg Leu Leu Lys Ile Ser Leu Asn Glu Ser
                565                 570                 575

Met Gln Val Val Ser Arg Arg Val Leu Thr Val Ala Tyr Gly Glu Pro
            580                 585                 590

Val His His Val Met Gln Phe Asp Pro Met Asp Pro Gly Tyr Leu Tyr
        595                 600                 605

Leu Met Thr Ser His Gln Met Ala Arg Val Lys Val Ala Ala Cys Glu
610                 615                 620

Val His Ser Thr Cys Gly Asp Cys Val Gly Ala Ala Asp Ala Tyr Cys
625                 630                 635                 640
```

-continued

```
Gly Trp Cys Thr Leu Glu Thr Arg Cys Thr Leu Gln Gln Asp Cys Thr
            645                 650                 655

Asn Ser Ser Gln Pro His Phe Trp Thr Ser Ala Ser Glu Gly Pro Ser
            660                 665                 670

Arg Cys Pro Ala Met Thr Val Leu Pro Ser Glu Ile Asp Val His Arg
            675                 680                 685

Asp Tyr Thr Gly Met Ile Leu Gln Ile Ser Gly Ser Leu Pro Ser Leu
            690                 695                 700

Ser Gly Met Glu Met Ala Cys Asp Tyr Gly Asn Gly Val Arg Thr Val
705                 710                 715                 720

Ala Arg Val Pro Gly Pro Ala Tyr Asp His Gln Ile Ala Tyr Cys Asn
            725                 730                 735

Leu Leu Pro Arg Ala Gln Phe Pro Ser Phe Pro Ala Gly Gln Asp His
            740                 745                 750

Val Thr Val Glu Met Ser Val Arg Val Lys Gly His Asn Ile Val Ser
            755                 760                 765

Ala Asn Phe Thr Ile Tyr Asp Cys Ser Arg Ile Gly Gln Val Tyr Pro
770                 775                 780

His Thr Ala Cys Thr Ser Cys Leu Ser Thr Gln Trp Pro Cys Ser Trp
785                 790                 795                 800

Cys Ile Gln Leu His Ser Cys Val Ser Asn Gln Ser Gln Cys Gln Asp
            805                 810                 815

Ser Pro Asn Pro Thr Ser Pro Gln Asp Cys Pro Gln Ile Leu Pro Ser
            820                 825                 830

Pro Leu Ala Pro Val Pro Thr Gly Ser Gln Asp Ile Leu Val Pro
            835                 840                 845

Leu Thr Lys Ala Thr Phe Phe His Gly Ser Ser Leu Glu Cys Ser Phe
            850                 855                 860

Gly Leu Glu Glu Ser Phe Glu Ala Val Trp Ala Asn Asn Ser Leu Val
865                 870                 875                 880

Arg Cys Asn Gln Val Val Leu His Thr Thr Gln Lys Ser Gln Val Phe
            885                 890                 895

Pro Leu Ser Leu Lys Leu Lys Gly Pro Pro Asp Arg Phe Leu Asp Ser
            900                 905                 910

Pro Asn Pro Met Thr Val Val Tyr Asn Cys Ala Met Gly Ser Pro
            915                 920                 925

Asp Cys Ser Gln Cys Leu Gly Arg Glu Asp Leu Gly His Leu Cys Val
930                 935                 940

Trp Asn Asp Gly Cys Arg Leu Arg Gly Pro Leu Gln Pro Leu Pro Gly
945                 950                 955                 960

Thr Cys Pro Ala Pro Glu Ile Arg Ala Ile Glu Pro Leu Ser Gly Pro
            965                 970                 975

Leu Asp Gly Gly Thr Leu Leu Thr Ile Arg Gly Arg Asn Leu Gly Arg
            980                 985                 990

Arg Leu Ser Asp Val Ala His Gly Val Trp Ile Gly Ser Val Ala Cys
            995                1000                1005

Glu Pro Leu Ala Asp Arg Tyr Thr Val Ser Glu Glu Ile Val Cys
    1010                1015                1020

Ala Thr Gly Pro Ala Ala Gly Ala Phe Ser Asp Val Val Thr Val
    1025                1030                1035

Asn Val Ser Lys Glu Gly Arg Ser Arg Glu Gln Phe Ser Tyr Val
    1040                1045                1050

Leu Pro Thr Val His Ser Leu Glu Pro Ser Met Gly Pro Lys Ala
```

-continued

```
            1055                1060                1065

Gly Gly Thr Arg Ile Thr Ile His Gly Ser Asp Leu Asn Val Gly
    1070                1075                1080

Ser Met Leu Gln Val Leu Val Asn Asp Thr Asp Pro Cys Thr Asp
    1085                1090                1095

Leu Thr Arg Thr Ala Thr Ser Ile Thr Cys Thr Val Pro Gly Gly
    1100                1105                1110

Thr Leu Pro Ser Pro Val Pro Val Cys Val Arg Phe Glu Ser Arg
    1115                1120                1125

Gly Cys Val His Gly Asn Leu Thr Phe Trp Tyr Met Gln Asn Pro
    1130                1135                1140

Val Ile Thr Ala Ile Ser Pro Gly Arg Ser Pro Val Ser Gly Gly
    1145                1150                1155

Arg Thr Ile Thr Val Ala Gly Glu Arg Phe His Met Val Gln Asn
    1160                1165                1170

Val Ser Met Ala Val His His Ile Gly Arg Glu Pro Thr Phe Cys
    1175                1180                1185

Lys Val Leu Asn Ser Thr Leu Ile Thr Cys Pro Ser Pro Gly Ala
    1190                1195                1200

Leu Ser Asn Ala Ser Ala Pro Val Asp Phe Phe Ile Asn Gly Arg
    1205                1210                1215

Ala Tyr Ala Asp Glu Ala Ala Glu Glu Leu Leu Asp Pro Ala Glu
    1220                1225                1230

Ala Gln Arg Gly Ser Arg Phe Arg Leu Asp Tyr Leu Pro Asn Pro
    1235                1240                1245

Gln Phe Ser Thr Ala Lys Arg Glu Lys Trp Ile Lys His His Pro
    1250                1255                1260

Gly Glu Pro Leu Thr Leu Val Ile His Lys Glu Gln Asp Ser Leu
    1265                1270                1275

Gly Leu Glu Ser His Glu Tyr His Ile Lys Ile Gly Gln Val Ser
    1280                1285                1290

Cys Asp Ile Gln Ile Ile Ser Asp Arg Val Ile His Cys Ser Val
    1295                1300                1305

Asn Glu Ser Leu Gly Thr Ala Glu Gly Gln Leu Pro Ile Thr Ile
    1310                1315                1320

Gln Val Gly Asn Phe Asn Gln Thr Ile Ala Thr Leu Gln Leu Gly
    1325                1330                1335

Gly Ser Glu Thr Ala Ile Val Val Ser Ile Val Ile Cys Ser Val
    1340                1345                1350

Leu Leu Leu Leu Ser Val Val Ala Leu Phe Val Phe Cys Thr Lys
    1355                1360                1365

Ser Arg Arg Ala Glu Arg Tyr Trp Gln Lys Thr Leu Leu Gln Met
    1370                1375                1380

Glu Glu Met Glu Ser Gln Ile Arg Glu Glu Ile Arg Lys Gly Phe
    1385                1390                1395

Ala Glu Leu Gln Thr Asp Met Thr Asp Leu Thr Lys Glu Leu Asn
    1400                1405                1410

Arg Ser Gln Gly Ile Pro Phe Leu Glu Tyr Lys His Phe Val Thr
    1415                1420                1425

Arg Thr Phe Phe Pro Lys Cys Ser Ser Leu Tyr Glu Glu Arg Tyr
    1430                1435                1440

Val Leu Pro Ser Lys Thr Leu Asn Ser Gln Gly Gly Ser Pro Pro
    1445                1450                1455
```

-continued

```
Gln Glu Thr His Pro Leu Leu Gly Glu Trp Asn Ile Pro Glu His
    1460                1465                1470

Cys Arg Pro Ser Met Glu Glu Gly Ile Ser Leu Phe Ser Ser Leu
    1475                1480                1485

Leu Asn Asn Lys His Phe Leu Ile Val Phe Val His Ala Leu Glu
    1490                1495                1500

Gln Gln Lys Asp Phe Ala Val Arg Asp Arg Cys Ser Leu Ala Ser
    1505                1510                1515

Leu Leu Thr Ile Ala Leu His Gly Lys Leu Glu Tyr Tyr Thr Ser
    1520                1525                1530

Ile Met Lys Glu Leu Leu Val Asp Leu Ile Asp Ala Ser Ala Ala
    1535                1540                1545

Lys Asn Pro Lys Leu Met Leu Arg Arg Thr Glu Ser Val Val Glu
    1550                1555                1560

Lys Met Leu Thr Asn Trp Met Ser Ile Cys Met Tyr Gly Cys Leu
    1565                1570                1575

Arg Glu Thr Val Gly Glu Pro Phe Phe Leu Leu Leu Cys Ala Ile
    1580                1585                1590

Lys Gln Gln Ile Asn Lys Gly Ser Ile Asp Ala Ile Thr Gly Lys
    1595                1600                1605

Ala Arg Tyr Thr Leu Asn Glu Glu Trp Leu Leu Arg Glu Asn Ile
    1610                1615                1620

Glu Ala Lys Pro Arg Asn Leu Asn Val Ser Phe Gln Gly Cys Gly
    1625                1630                1635

Met Asp Ser Leu Ser Val Arg Ala Met Asp Thr Asp Thr Leu Thr
    1640                1645                1650

Gln Val Lys Glu Lys Ile Leu Glu Ala Phe Cys Lys Asn Val Pro
    1655                1660                1665

Tyr Ser Gln Trp Pro Arg Ala Glu Asp Val Asp Leu Glu Trp Phe
    1670                1675                1680

Ala Ser Ser Thr Gln Ser Tyr Val Leu Arg Asp Leu Asp Asp Thr
    1685                1690                1695

Ser Val Val Glu Asp Gly Arg Lys Lys Leu Asn Thr Leu Ala His
    1700                1705                1710

Tyr Lys Ile Pro Glu Gly Ala Ser Leu Ala Met Ser Leu Thr Asp
    1715                1720                1725

Lys Lys Asp Ser Thr Leu Gly Arg Val Lys Asp Leu Asp Thr Glu
    1730                1735                1740

Lys Tyr Phe His Leu Val Leu Pro Thr Asp Glu Leu Val Glu Pro
    1745                1750                1755

Lys Lys Ser His Arg Gln Ser His Arg Lys Lys Val Leu Pro Glu
    1760                1765                1770

Ile Tyr Leu Thr Arg Leu Leu Ser Thr Lys Gly Thr Leu Gln Lys
    1775                1780                1785

Phe Leu Asp Asp Leu Phe Lys Ala Ile Leu Ser Ile Arg Glu Asp
    1790                1795                1800

Lys Pro Pro Leu Ala Val Lys Tyr Phe Phe Asp Phe Leu Glu Glu
    1805                1810                1815

Gln Ala Glu Lys Arg Gly Ile Ser Asp Pro Asp Thr Leu His Ile
    1820                1825                1830

Trp Lys Thr Asn Ser Leu Pro Leu Arg Phe Trp Val Asn Ile Leu
    1835                1840                1845
```

| | | | | | | | | | | |
|---|---|---|---|---|---|---|---|---|---|---|
| Lys | Asn | Pro | Gln | Phe | Val | Phe | Asp | Ile | Glu | Lys | Thr | Asp | His | Ile |
| | 1850 | | | | 1855 | | | | 1860 | | | | | |
| Asp | Ala | Cys | Leu | Ser | Val | Ile | Ala | Gln | Ala | Phe | Ile | Asp | Ala | Cys |
| | 1865 | | | | 1870 | | | | 1875 | | | | | |
| Ser | Ile | Ser | Asp | Leu | Gln | Leu | Gly | Lys | Asp | Ser | Pro | Thr | Asn | Lys |
| | 1880 | | | | 1885 | | | | 1890 | | | | | |
| Leu | Leu | Tyr | Ala | Lys | Glu | Ile | Pro | Glu | Tyr | Arg | Lys | Thr | Val | Gln |
| | 1895 | | | | 1900 | | | | 1905 | | | | | |
| Arg | Tyr | Tyr | Lys | Gln | Ile | Gln | Asp | Met | Thr | Pro | Leu | Ser | Glu | Gln |
| | 1910 | | | | 1915 | | | | 1920 | | | | | |
| Glu | Met | Asn | Ala | His | Leu | Ala | Glu | Glu | Ser | Arg | Lys | Tyr | Gln | Asn |
| | 1925 | | | | 1930 | | | | 1935 | | | | | |
| Glu | Phe | Asn | Thr | Asn | Val | Ala | Met | Ala | Glu | Ile | Tyr | Lys | Tyr | Ala |
| | 1940 | | | | 1945 | | | | 1950 | | | | | |
| Lys | Arg | Tyr | Arg | Pro | Gln | Ile | Met | Ala | Ala | Leu | Glu | Ala | Asn | Pro |
| | 1955 | | | | 1960 | | | | 1965 | | | | | |
| Thr | Ala | Arg | Arg | Thr | Gln | Leu | Gln | His | Lys | Phe | Glu | Gln | Val | Val |
| | 1970 | | | | 1975 | | | | 1980 | | | | | |
| Ala | Leu | Met | Glu | Asn | Asn | Ile | Tyr | Glu | Cys | Tyr | Ser | Glu | Ala | |
| | 1985 | | | | 1990 | | | | 1995 | | | | | |

```
<210> SEQ ID NO 16
<211> LENGTH: 6931
<212> TYPE: DNA
<213> ORGANISM: mouse

<400> SEQUENCE: 16
gggagatggg ctgtgggcgt ggtctccacg gagccgcccc cgggctgagc gcctcgccag      60
agtcgggccg gggcgccggg gccggggggcg gcaggcgcgg gcaggaagcg cctcgcggcc     120
cgggcccgcc cccgcctctc cgccgcctcc gagctcccgg ctcccggccg cgccgcgccc     180
catgcactcg ccgcgccgcg cagcccgcgc tcgcctggat ggctcgtcgc gccgcgggcg     240
gcgcaccccc tagcgcccgg gccgccgcgg ccgtcccctt gcgtccgcgc cctcactcgc     300
ggggccctgg tctgctgccg ctgcctctgc tgctgctgct cggggcggca cgggccggcg     360
ccctagagat ccagcgccgt ttcccctcgc ccacgcccac caacaacttc gccctggacg     420
gcacggcggg caccgtgtac ttggcggcag tgaaccgcct gtaccaactg tcgagtgcca     480
acttgagcct ggaagccgag gcgaccgtgg gtcccgtgcc ggacagcccg ctgtgtcacg     540
ccccgcagct cccgcaggcc tcgtgcgagc accgcggcg cctcacggac aactacaaca     600
aaatcctgca gttggacccg ggccagggtc tggtggtcgc gtgcggctcc atctaccagg     660
gtctgtgcca gctgaggcgc cggggcaaca tctcagccct ggccgtgagc tttccgcctg     720
ccgcgccgac cgcagaaccg gtcaccgtgt tccccagcat gctcaacgtg gccgccaacc     780
accccaacgc gtccactgtg ggactggtgc tgccgcctac ctcgggcacc gggggcagcc     840
gtctgctcgt gggcgccacg tacaccggct tcggcagcgc tttcttcccg cgcaaccgta     900
gcctagaaga ccaccgcttc gagaacacgc ccgagatcgc tatccgctcc ctggacgcgc     960
gtggagactt ggccaagctc ttcaccttcg accttaaccc gtcggacgat aacatcctga    1020
agatcaagca gggcgccaag gagcagcaca agctgggctt cgtgcgtgcc ttcttgcacc    1080
cggcggtgcc accgcacagc gcgcagcccg acgcgtacct ggcgctcaac agcgaggcgc    1140
gtgcgggcga caaggacagc caggcgcgca gcctgctggc gcgcatctgc ctgccccgcg    1200
gcgcgggtgg cgacgccaag aagctcaccg agtcctacat ccaactgggc ttgcagtgcg    1260
```

```
cgggcggcgc gggccgcggc gacctctaca gccgcctcgt gtcggttttc cccgcgcgcg    1320
agcagttctt cgccgtcttc gagcggcccc agggcgcccc aggtgcccgc aacgccccgg    1380
ccgcgctttg cgccttccgc ttcgacgacg tgcaggctgc cattcgtgca gcgcgcaccg    1440
cctgcttcgt ggagccggcg cccgacgtgg tggcggtgtt ggacagtgtg gtgcagggca    1500
ccgggccggc ctgcgagagc aagcgcaaca tacagctgca gccggagcaa ctggattgcg    1560
gagcggccca cctgcagcac ccactgacca tcctgcagcc gctgagggca tcgcccgtgt    1620
tccgtgctcc agggctcacg gccgtggctg tggccagtgc caacaactac acggccgtct    1680
ttctgggcac cgccacaggg aggctcctca agatcagcct gaacgagagc atgcaggtag    1740
taagcaggcg agtgctgact gtagcctatg gggagcctgt gcatcacgtc atgcagtttg    1800
accccatgga tcctggttac ctatacctga tgacatccca ccagatggcc cgagtgaagg    1860
tggcagcgtg tgaggtacac tccacctgcg gggactgcgt gggtgcggcc gatgcctact    1920
gtggttggtg cactctggag acccggtgca cactccagca ggattgcacc aactccagcc    1980
agccacattt ctggaccagt gccagtgagg gccccagccg ctgccctgcc atgacagtac    2040
tgccctcgga gattgatgtg caccgggact acacaggtat gatcttacag atctcaggaa    2100
gcctgcccag cctcagcggc atggagatgg cttgtgacta tggaaatggc gttcgaacgg    2160
tggcccgggt acctggccct gcctatgatc atcagattgc ctactgcaat ctcctgccca    2220
gggcccagtt tccatccttt cctgctggcc aggaccacgt gaccgttgag atgtctgtaa    2280
gggtcaaagg acacaacatt gtctcagcca atttcaccat ctacgactgc agccgaattg    2340
gacaagtcta cccccataca gcctgtacca gctgcctgtc cacacagtgg ccttgctcct    2400
ggtgcatcca gctgcattca tgtgtctcca accagtctca gtgccaggac tcgccaaacc    2460
ccacgagtcc tcaggactgt ccccagatcc tgccctcgcc cctagcgccc gtgcccacag    2520
gtggctccca agacatcctg gtgccccctga ctaaagccac cttcttccat ggttcctccc    2580
tcgagtgcag ctttgggctg aagagagct ttgaggctgt atgggcgaat aactcactgg    2640
tccgctgcaa ccaagtggtg ctgcacacaa cccagaagag ccaggtatttt ccactgagtc    2700 tgaagctgaa ggggccgcca gaccgattcc tagacagccc taaccccatg acagttgtgg    2760
tctacaactg tgctatgggc agccctgact gttcccagtg cctgggccgt gaggacctgg    2820
gtcacctctg tgtttggaat gatggctgtc gtctaagagg gccctgcag ccactccctg    2880 gcacctgccc agcccctgaa atccagcga ttgagcctct gagtggcccc ttggacggtg    2940
ggactttgct gaccatccgt ggcaggaact tgggccgtcg gctcagtgat gtggcacatg    3000
gtgtgtggat tggcagtgtg gcctgtgaac ccctggctga cagatacacc gtttcagagg    3060
agatcgtgtg tgccacaggg cctgccgcag gggccttctc agacgtggta acggtgaacg    3120
tctccaagga aggcaggtct cgggaacagt tctcctatgt gctgcccacg gtccactcac    3180
tggagccttc catgggccca aaggccgggg gtacaaggat caccattcac ggcagtgacc    3240
tcaacgtggg ctctatgctc caggtcctgg tgaatgacac ggacccctgc acagatctta    3300
cgcgcacagc caccagcatc acctgcactg tgccagggggg tacctgccc ctctccagtgc    3360 ctgtgtgtgt gcgcttcgag agccggggct gcgtgcacgg aaacctcacc ttctggtaca    3420
tgcagaaccc agtcatcaca gccatcagcc caggccgcag ccctgtcagt ggcggcagga    3480
ccatcactgt ggctggcgaa cgcttccaca tggtgcagaa tgtatcaatg gctgtacacc    3540
acattggccg ggagcccacg ttctgcaagg ttctcaactc cacactcatc acctgcccat    3600
```

-continued

```
ctcctggagc cctgagcaat gcttcggcgc ctgtagactt cttcatcaat ggccgggcat    3660
atgcagacga ggcagccgag gagctgctgg accctgcaga ggcacagagg ggcagccggt    3720
tccgcctaga ctacctcccc aacccacagt tctccacagc caagagggag aagtggatca    3780
aacatcaccc aggagagccg ctcaccctcg tcatccataa ggagcaagac agcctggggc    3840
tggagagcca tgagtaccac atcaagattg gccaggtgtc ctgcgacatc cagatcatct    3900
cagacagagt catccactgc tcagtcaatg agtcgctggg cacggctgaa ggacagctgc    3960
ccatcacaat ccaggtgggg aacttcaacc agaccatcgc cacactgcaa ctgggggca    4020 gcgagacggc cattgtggtg tccatcgtca tctgcagtgt cctgttgctg ctgtctgtgg    4080
ttgctctgtt cgtcttctgc accaagagcc gccgtgccga gcgctactgg cagaagaccc    4140
tgctgcagat ggaagagatg gagtctcaga tccgagagga gatccgtaaa ggctttgcgg    4200
agctgcagac agacatgacg gatctcacca aggagctgaa ccgcagccag ggcatcccct    4260
tcttggagta caagcacttc gtgactcgaa ccttcttccc caagtgctct tccctctatg    4320
aagagcggta tgtgctgccc tcgaagaccc tcaactccca gggtggctcc ccgccacagg    4380
aaacccaccc actgctggga gagtggaaca tccctgaaca ctgtcggccc agcatggagg    4440
aggggatcag cctgttctcc tcactgctca acaacaagca cttcctcatc gtcttcgtcc    4500
atgctctgga gcagcagaag gacttcgcag tgcgtgacag gtgcagcctg gcgtccctgc    4560
tgaccatcgc gctgcacggc aagctggagt actatacgag catcatgaag gagctgctcg    4620
tggacctcat cgacgcctcg gcggccaaga accccaagct catgttgcgg cgcacggagt    4680
ctgtggtgga gaagatgctt accaactgga tgtccatctg catgtacggc tgcctgaggg    4740
agacagtagg tgagccgttc ttcctgctgt tgtgtgccat caagcagcag atcaacaaag    4800
gctccatcga cgccatcaca ggcaaagccc gctacacact caacgaggag tggctgctga    4860
gggagaacat tgaggccaag ccccggaact tgaacgtgtc cttccaggac tgtgggatgg    4920
actccctcag cgtgcgggcc atggacaccg acacgctgac gcaggtgaag gagaagatcc    4980
tggaagcctt ctgcaagaac gtcccctact cacagtggcc gcgggcggag gacgtggacc    5040
ttgaatggtt tgcctcgagt acccagagct acgtcctccg ggacctggat gacacatcag    5100
tggtggagga cggccgtaag aaactgaaca cactggccca ctacaagata cctgagggcg    5160
cctccctagc catgagcctc acagacaaga aggacagtac cctgggcaga gtgaaagact    5220
tggacacaga aaagtatttc catttggtgc tacctacgga tgagctggta gagcctaaga    5280
aatctcaccg gcagagccac cgcaagaaag tattgccaga gatctacctg acccgcctgc    5340
tgtccaccaa gggcacgctg cagaagttcc tagatgacct gttcaaggct atcctgagca    5400
tccgagagga caagccccg ctggctgtca agtatttctt tgacttccta gaggaacagg    5460
cggagaagag aggcatctcc gaccctgaca ccctgcatat ctggaagacc aacagccttc    5520
ccctgcgctt ctgggtgaac atcttaaaaa atccccagtt tgtcttcgac atagagaaga    5580
cggaccacat cgacgcctgc ctgtctgtca tcgcacaggc cttcatcgat gcctgctcca    5640
tctctgacct gcagctgggc aaggactcac ccaccaacaa gcttctgtac gcgaaggaga    5700
tccctgagta ccggaagacc gtacagcgct attataaaca gatccaagac atgacgccgc    5760
tcagcgagcg ggaaatgaac gcacacctgg ccgaggagtc tcggaaatac cagaatgagt    5820
tcaacacaaa cgtggccatg gctgagattt ataaatatgc taagaggtat cgaccacaga    5880
tcatggctgc cctggaggcc aacccccacag cccgcaggac ccagctacag cacaagtttg    5940
aacaggtggt ggctctgatg gaaaacaata tctatgagtg ttacagcgag gcctgatgca    6000
```

```
gaagagtgac caggagcttc ggccagggag acggcgtgca ggccacttgg cctccacttg    6060
gtttcttccc cacatctctc acttgggctg ggaactgaca gaggagcctg ctgggctagg    6120
agtgggggac actggcctct tagtgcccgg ctgccgagct cttggccttg tcccctgggg    6180
catctctgtc ccctccacct gcccaagacc caactctagg atgaaggcct tgaatatcga    6240
tcgctgccag tccctaataa gactttccct gccaaccagg acagcctgga ccatgcctgc    6300
ctgttcactg tttcaggctg ctcagcacac attgggagag gtggccatat cccagaacac    6360
tacctcatcc acctggcaga gggaatttct gcttcagcca ccaagcagtt gtctgtgtcc    6420
ctcatccaga gggggccttg gccaccaaca gttccaaacc aggtcagctg ttagccgtct    6480
cattggccag tggcagcatg ggcagtgccc attgcccaca gaacggtgga gagaggggga    6540
caggctgggg gttcctggcc ccaggaaagg gaggaaggcg aggatgcagg gctgtagctg    6600
gactactcag tcttcctgga agtgtttcta aagagcacca cttttttttg ttttttgttt    6660
tttaagaaaa aaaaaacttt tatatattaa acaaaaact tatgcaccaa ctgtgaatag    6720
ctgccgcttg tgcagatccc caggggctcc cggtgacaca ctggaaatga ctgttccagg    6780
ggacagaaaa tactcatctg tccccagcac agccccacc ccaccccca tagctgctga    6840 gactggctca cagcccaagg gggctgggct ggaggggaag gctgggactc tctggaacat    6900
tctttataat aaaagcctgc cgggaaaacc t                                   6931

<210> SEQ ID NO 17
<211> LENGTH: 484
<212> TYPE: DNA
<213> ORGANISM: mouse genome

<400> SEQUENCE: 17
tgacctcgga ccgcggggcg tggcccagag gcgtggccgg gggcgtggcc cggggcgaaa      60
gggcgtgggc caagctgctg gggcggggag atgggctgtg ggcgtggtct ccacggagcc    120
gcccccgggc tgagcgcctc gccagagtcg ggccggggcg ccggggccgg gggcggcagg    180
cgcgggcagg aagcgcctcg cggcccgggc ccgcccccg cctctcgccg cctccgagct    240
cccggctccc ggccgcgccg cgcccatgc actcgccgcg ccgcgcagcc cgcgctcgcc    300
tggatggctc gtcgcgccgc gggcggcgca cccctagcg cccgggccgc cgcggccgtc    360
cccttgcgtc cgcgcccctca ctcgcggggc cctggtctgc tgccgctgcc tctgctgctg    420
ctgctcgggg cggcacgggc cggcgcccta aagatccagc gccgtttccc ctcgcccacg    480
ccca                                                                484

<210> SEQ ID NO 18
<211> LENGTH: 1337
<212> TYPE: PRT
<213> ORGANISM: mouse

<400> SEQUENCE: 18

Met Gly Cys Gly Arg Gly Leu His Gly Ala Ala Pro Gly Leu Ser Ala
 1               5                  10                  15

Ser Pro Glu Ser Gly Arg Gly Ala Gly Ala Gly Gly Arg Arg Gly
            20                  25                  30

Gln Glu Ala Pro Arg Gly Pro Gly Pro Pro Ala Ser Arg Arg Leu
        35                  40                  45

Arg Ala Pro Gly Ser Arg Pro Arg Arg Ala Pro Cys Thr Arg Arg Ala
    50                  55                  60
```

-continued

```
Ala Gln Pro Ala Leu Ala Trp Met Ala Arg Ala Ala Gly Gly Ala
 65                  70                  75                  80

Pro Pro Ser Ala Arg Ala Ala Ala Val Pro Leu Arg Pro Arg Pro
                 85                  90                  95

His Ser Arg Gly Pro Gly Leu Leu Pro Leu Pro Leu Leu Leu Leu
            100                 105                 110

Gly Ala Ala Arg Ala Gly Ala Leu Glu Ile Gln Arg Arg Phe Pro Ser
        115                 120                 125

Pro Thr Pro Thr Asn Asn Phe Ala Leu Asp Gly Thr Ala Gly Thr Val
    130                 135                 140

Tyr Leu Ala Ala Val Asn Arg Leu Tyr Gln Leu Ser Ser Ala Asn Leu
145                 150                 155                 160

Ser Leu Glu Ala Glu Ala Thr Val Gly Pro Val Pro Asp Ser Pro Leu
                165                 170                 175

Cys His Ala Pro Gln Leu Pro Gln Ala Ser Cys Glu His Pro Arg Arg
            180                 185                 190

Leu Thr Asp Asn Tyr Asn Lys Ile Leu Gln Leu Asp Pro Gly Gln Gly
        195                 200                 205

Leu Val Val Ala Cys Gly Ser Ile Tyr Gln Gly Leu Cys Gln Leu Arg
210                 215                 220

Arg Arg Gly Asn Ile Ser Ala Leu Ala Val Ser Phe Pro Pro Ala Ala
225                 230                 235                 240

Pro Thr Ala Glu Pro Val Thr Val Phe Pro Ser Met Leu Asn Val Ala
                245                 250                 255

Ala Asn His Pro Asn Ala Ser Thr Val Gly Leu Val Leu Pro Pro Thr
            260                 265                 270

Ser Gly Thr Gly Gly Ser Arg Leu Leu Val Gly Ala Thr Tyr Thr Gly
        275                 280                 285

Phe Gly Ser Ala Phe Phe Pro Arg Asn Arg Ser Leu Glu Asp His Arg
290                 295                 300

Phe Glu Asn Thr Pro Glu Ile Ala Ile Arg Ser Leu Asp Ala Arg Gly
305                 310                 315                 320

Asp Leu Ala Lys Leu Phe Thr Phe Asp Leu Asn Pro Ser Asp Asp Asn
                325                 330                 335

Ile Leu Lys Ile Lys Gln Gly Ala Lys Glu Gln His Lys Leu Gly Phe
            340                 345                 350

Val Arg Ala Phe Leu His Pro Ala Val Pro Pro His Ser Ala Gln Pro
        355                 360                 365

Tyr Ala Tyr Leu Ala Leu Asn Ser Glu Ala Arg Ala Gly Asp Lys Asp
    370                 375                 380

Ser Gln Ala Arg Ser Leu Leu Ala Arg Ile Cys Leu Pro Arg Gly Ala
385                 390                 395                 400

Gly Gly Asp Ala Lys Lys Leu Thr Glu Ser Tyr Ile Gln Leu Gly Leu
                405                 410                 415

Gln Cys Ala Gly Gly Ala Gly Arg Gly Asp Leu Tyr Ser Arg Leu Val
            420                 425                 430

Ser Val Phe Pro Ala Arg Glu Gln Phe Ala Val Phe Glu Arg Pro
        435                 440                 445

Gln Gly Ala Pro Gly Ala Arg Asn Ala Pro Ala Leu Cys Ala Phe
    450                 455                 460

Arg Phe Asp Asp Val Gln Ala Ala Ile Arg Ala Ala Arg Thr Ala Cys
465                 470                 475                 480

Phe Val Glu Pro Ala Pro Asp Val Val Ala Val Leu Asp Ser Val Val
```

-continued

```
            485                 490                 495
Gln Gly Thr Gly Pro Ala Cys Glu Ser Lys Arg Asn Ile Gln Leu Gln
            500                 505                 510

Pro Glu Gln Leu Asp Cys Gly Ala Ala His Leu Gln His Pro Leu Thr
            515                 520                 525

Ile Leu Gln Pro Leu Arg Ala Ser Pro Val Phe Arg Ala Pro Gly Leu
            530                 535                 540

Thr Ala Val Ala Val Ala Ser Ala Asn Asn Tyr Thr Ala Val Phe Leu
545                 550                 555                 560

Gly Thr Ala Thr Gly Arg Leu Leu Lys Ile Ser Leu Asn Glu Ser Met
                565                 570                 575

Gln Val Val Ser Arg Arg Val Leu Thr Val Ala Tyr Gly Glu Pro Val
            580                 585                 590

His His Val Met Gln Phe Asp Pro Met Asp Pro Gly Tyr Leu Tyr Leu
            595                 600                 605

Met Thr Ser His Gln Met Ala Arg Val Lys Val Ala Ala Cys Glu Val
            610                 615                 620

His Ser Thr Cys Gly Asp Cys Val Gly Ala Ala Asp Ala Tyr Cys Gly
625                 630                 635                 640

Trp Cys Thr Leu Glu Thr Arg Cys Thr Leu Gln Gln Asp Cys Thr Asn
                645                 650                 655

Ser Ser Gln Pro His Phe Trp Thr Ser Ala Ser Glu Gly Pro Ser Arg
            660                 665                 670

Cys Pro Ala Met Thr Val Leu Pro Ser Glu Ile Asp Val His Arg Asp
            675                 680                 685

Tyr Thr Gly Met Ile Leu Gln Ile Ser Gly Ser Leu Pro Ser Leu Ser
            690                 695                 700

Gly Met Glu Met Ala Cys Asp Tyr Gly Asn Gly Val Arg Thr Val Ala
705                 710                 715                 720

Arg Val Pro Gly Pro Ala Tyr Asp His Gln Ile Ala Tyr Cys Asn Leu
                725                 730                 735

Leu Pro Arg Ala Gln Phe Pro Ser Phe Pro Ala Gly Gln Asp His Val
            740                 745                 750

Thr Val Glu Met Ser Val Arg Val Lys Gly His Asn Ile Val Ser Ala
            755                 760                 765

Asn Phe Thr Ile Tyr Asp Cys Ser Arg Ile Gly Gln Val Tyr Pro His
            770                 775                 780

Thr Ala Cys Thr Ser Cys Leu Ser Thr Gln Trp Pro Cys Ser Trp Cys
785                 790                 795                 800

Ile Gln Leu His Ser Cys Val Ser Asn Gln Ser Gln Cys Gln Asp Ser
                805                 810                 815

Pro Asn Pro Thr Ser Pro Gln Asp Cys Pro Gln Ile Leu Pro Ser Pro
            820                 825                 830

Leu Ala Pro Val Pro Thr Gly Ser Gln Asp Ile Leu Val Pro Leu
            835                 840                 845

Thr Lys Ala Thr Phe Phe His Gly Ser Ser Leu Glu Cys Ser Phe Gly
            850                 855                 860

Leu Glu Glu Ser Phe Glu Ala Val Trp Ala Asn Asn Ser Leu Val Arg
865                 870                 875                 880

Cys Asn Gln Val Val Leu His Thr Thr Gln Lys Ser Gln Val Phe Pro
                885                 890                 895

Leu Ser Leu Lys Leu Lys Gly Pro Pro Asp Arg Phe Leu Asp Ser Pro
            900                 905                 910
```

-continued

```
Asn Pro Met Thr Val Val Tyr Asn Cys Ala Met Gly Ser Pro Asp
        915                 920                 925

Cys Ser Gln Cys Leu Gly Arg Glu Asp Leu Gly His Leu Cys Val Trp
        930                 935                 940

Asn Asp Gly Cys Arg Leu Arg Gly Pro Leu Gln Pro Leu Pro Gly Thr
945                 950                 955                 960

Cys Pro Ala Pro Glu Ile Arg Ala Ile Glu Pro Leu Ser Gly Pro Leu
                965                 970                 975

Asp Gly Gly Thr Leu Leu Thr Ile Arg Gly Arg Asn Leu Gly Arg Arg
                980                 985                 990

Leu Ser Asp Val Ala His Gly Val Trp Ile Gly Ser Val Ala Cys Glu
        995                 1000                1005

Pro Leu Ala Asp Arg Tyr Thr Val Ser Glu Glu Ile Val Cys Ala
    1010                1015                1020

Thr Gly Pro Ala Ala Gly Ala Phe Ser Asp Val Val Thr Val Asn
    1025                1030                1035

Val Ser Lys Glu Gly Arg Ser Arg Glu Gln Phe Ser Tyr Val Leu
    1040                1045                1050

Pro Thr Val His Ser Leu Glu Pro Ser Met Gly Pro Lys Ala Gly
    1055                1060                1065

Gly Thr Arg Ile Thr Ile His Gly Ser Asp Leu Asn Val Gly Ser
    1070                1075                1080

Met Leu Gln Val Leu Val Asn Asp Thr Asp Pro Cys Thr Asp Leu
    1085                1090                1095

Thr Arg Thr Ala Thr Ser Ile Thr Cys Thr Val Pro Gly Gly Thr
    1100                1105                1110

Leu Pro Ser Pro Val Pro Val Cys Val Arg Phe Glu Ser Arg Gly
    1115                1120                1125

Cys Val His Gly Asn Leu Thr Phe Trp Tyr Met Gln Asn Pro Val
    1130                1135                1140

Ile Thr Ala Ile Ser Pro Gly Arg Ser Pro Val Ser Gly Gly Arg
    1145                1150                1155

Thr Ile Thr Val Ala Gly Glu Arg Phe His Met Val Gln Asn Val
    1160                1165                1170

Ser Met Ala Val His His Ile Gly Arg Glu Pro Thr Phe Cys Lys
    1175                1180                1185

Val Leu Asn Ser Thr Leu Ile Thr Cys Pro Ser Pro Gly Ala Leu
    1190                1195                1200

Ser Asn Ala Ser Ala Pro Val Asp Phe Phe Ile Asn Gly Arg Ala
    1205                1210                1215

Tyr Ala Asp Glu Ala Ala Glu Leu Leu Asp Pro Ala Glu Ala
    1220                1225                1230

Gln Arg Gly Ser Arg Phe Arg Leu Asp Tyr Leu Pro Asn Pro Gln
    1235                1240                1245

Phe Ser Thr Ala Lys Arg Glu Lys Trp Ile Lys His His Pro Gly
    1250                1255                1260

Glu Pro Leu Thr Leu Val Ile His Lys Glu Gln Asp Ser Leu Gly
    1265                1270                1275

Leu Glu Ser His Glu Tyr His Ile Lys Ile Gly Gln Val Ser Cys
    1280                1285                1290

Asp Ile Gln Ile Ile Ser Asp Arg Val Ile His Cys Ser Val Asn
    1295                1300                1305
```

```
Glu Ser Leu Gly Thr Ala Glu Gly Gln Leu Pro Ile Thr Ile Gln
    1310                1315                1320

Val Gly Asn Phe Asn Gln Thr Ile Ala Thr Leu Gln Leu Gly
1325                1330                1335

<210> SEQ ID NO 19
<211> LENGTH: 4011
<212> TYPE: DNA
<213> ORGANISM: mouse

<400> SEQUENCE: 19
atgggctgtg gcgtggtct ccacggagcc gcccccgggc tgagcgcctc gccagagtcg      60
ggccggggcg ccggggccgg gggcggcagg cgcgggcagg aagcgcctcg cggcccgggc     120 ccgcccccg cctctcgccg cctccgagct cccggctccc ggccgcgccg cgcccatgc      180 actcgccgcg ccgcgcagcc cgcgctcgcc tggatggctc gtcgcgccgc gggcggcgca     240 cccctagcg cccgggccgc cgcggccgtc cccttgcgtc cgcgccctca ctcgcggggc      300
cctggtctgc tgccgctgcc tctgctgctg ctgctcgggg cggcacgggc cggcgcccta     360
gagatccagc gccgtttccc ctcgcccacg cccaccaaca acttcgccct ggacggcacg     420
gcgggcaccg tgtacttggc ggcagtgaac cgcctgtacc aactgtcgag tgccaacttg     480
agcctggaag ccgaggcgac cgtgggtccc gtgccggaca gccgctgtg tcacgccccg     540 cagctcccgc aggcctcgtg cgagcaccg cggcgcctca cggacaacta caacaaaatc      600
ctgcagttgg acccgggcca gggtctggtg gtcgcgtgcg gctccatcta ccagggtctg     660
tgccagctga ggcgccgggg caacatctca gccctggccg tgagctttcc gcctgccgcg     720
ccgaccgcag aaccggtcac cgtgttcccc agcatgctca acgtggccgc caaccacccc     780
aacgcgtcca ctgtgggact ggtgctgccg cctacctcgg caccggggg cagccgtctg     840 ctcgtgggcg ccacgtacac cggcttcggc agcgctttct cccgcgcaa ccgtagccta      900 gaagaccacc gcttcgagaa cacgcccgag atcgctatcc gctccctgga cgcgcgtgga     960
gacttggcca gctcttcac cttcgacctt aacccgtcgg acgataacat cctgaagatc     1020
aagcagggcg ccaaggagca gcacaagctg ggcttcgtgc gtgccttctt gcacccggcg    1080
gtgccaccgc acagcgcgca gccctacgcg tacctggcgc tcaacagcga ggcgcgtgcg    1140
ggcgacaagg acagccaggc gcgcagcctg ctggcgcgca tctgcctgcc ccgcggcgcg    1200
ggtggcgacg ccaagaagct caccgagtcc tacatccaac tgggcttgca gtgcgcgggc    1260
ggcgcgggcc gcggcgacct ctacagccgc ctcgtgtcgg ttttccccgc gcgcgagcag    1320
ttcttcgccg tcttcgagcg gccccagggc gccccaggtg cccgcaacgc ccggccgcg     1380 ctttgcgcct ccgcttcga cgacgtgcag gctgccattc gtgcagcgcg caccgcctgc    1440
ttcgtggagc cggcgcccga cgtggtggcg gtgttggaca gtgtggtgca gggcaccggg    1500
ccggcctgcg agagcaagcg caacatacag ctgcagccgg agcaactgga ttgcggagcg    1560
gcccacctgc agcacccact gaccatcctg cagccgctga gggcatcgcc cgtgttccgt    1620
gctccagggc tcacgccgt ggctgtgccc agtgccaaca actacacggc cgtcttcctg     1680
ggcaccgcca cagggaggct cctcaagatc agcctgaacg agagcatgca ggtagtaagc    1740
aggcgagtgc tgactgtagc ctatgggag cctgtgcatc acgtcatgca gtttgacccc     1800 atgcgatcctg gttacctata cctgatgaca tcccaccaga tggcccgagt gaaggtggca    1860
gcgtgtgagt acactccac ctgcggggac tgcgtgggtg cggccgatgc ctactgtggt     1920
tggtgcactc tggagacccg gtgcacactc cagcaggatt gcaccaactc cagccagcca    1980
```

```
catttctgga ccagtgccag tgagggcccc agccgctgcc ctgccatgac agtactgccc    2040
tcggagattg atgtgcaccg ggactacaca ggtatgatct tacagatctc aggaagcctg    2100
cccagcctca gcggcatgga gatggcttgt gactatggaa atggcgttcg aacggtggcc    2160
cgggtacctg gccctgccta tgatcatcag attgcctact gcaatctcct gcccagggcc    2220
cagtttccat cctttcctgc tggccaggac acgtgaccg ttgagatgtc tgtaagggtc    2280
aaaggacaca acattgtctc agccaatttc accatctacg actgcagccg aattggacaa    2340
gtctaccccc atacagcctg taccagctgc ctgtccacac agtggccttg ctcctggtgc    2400
atccagctgc attcatgtgt ctccaaccag tctcagtgcc aggactcgcc aaaccccacg    2460
agtcctcagg actgtcccca gatcctgccc tcgcccctag cgcccgtgcc cacaggtggc    2520
tcccaagaca tcctggtgcc cctgactaaa gccaccttct tccatggttc ctccctcgag    2580
tgcagctttg ggctggaaga gagctttgag gctgtatggg cgaataactc actggtccgc    2640
tgcaaccaag tggtgctgca cacaacccag aagagccagg tatttccact gagtctgaag    2700
ctgaaggggc cgccagaccg attcctagac agccctaacc ccatgacagt tgtggtctac    2760
aactgtgcta tgggcagccc tgactgttcc cagtgcctgg gccgtgagga cctgggtcac    2820
ctctgtgttt ggaatgatgg ctgtcgtcta gagggcccc tgcagccact ccctggcacc    2880
tgcccagccc ctgaaatccg agcgattgag cctctgagtg gcccccttgga cggtgggact    2940 ttgctgacca tccgtggcag gaacttgggc cgtcggctca gtgatgtggc acatggtgtg    3000
tggattggca gtgtggcctg tgaacccctg gctgacagat acaccgtttc agaggagatc    3060
gtgtgtgcca cagggcctgc cgcaggggcc ttctcagacg tggtaacggt gaacgtctcc    3120
aaggaaggca ggtctcggga acagttctcc tatgtgctgc ccacggtcca ctcactggag    3180
ccttccatgg gcccaaaggc cgggggtaca aggatcacca ttcacggcag tgacctcaac    3240
gtgggctcta tgctccaggt cctggtgaat gacacggacc cctgcacaga tcttacgcgc    3300
acagccacca gcatcacctg cactgtgcca gggggtaccc tgccctctcc agtgcctgtg    3360
tgtgtgcgct tcgagagccg gggctgcgtg cacgaaaacc tcaccttctg gtacatgcag    3420
aacccagtca tcacagccat cagcccaggc cgcagccctg tcagtggcgg caggaccatc    3480
actgtggctg cgaacgctt ccacatggtg cagaatgtat caatggctgt acaccacatt    3540
ggccgggagc ccacgttctg caaggttctc aactccacac tcatcacctg cccatctcct    3600
ggagccctga gcaatgcttc ggcgcctgta gacttcttca tcaatggccg ggcatatgca    3660
gacgaggcag ccgaggagct gctggaccct gcagaggcac agaggggcag ccggttccgc    3720
ctagactacc tccccaaccc acagttctcc acagccaaga gggagaagtg gatcaaacat    3780
cacccaggag agccgctcac cctcgtcatc cataaggagc aagacagcct ggggctggag    3840
agccatgagt accacatcaa gattggccag gtgtcctgcg acatccagat catctcagac    3900
agagtcatcc actgctcagt caatgagtcg ctgggcacgg ctgaaggaca gctgcccatc    3960
acaatccagg tggggaactt caaccagacc atcgccacac tgcaactggg g    4011
```

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide primer

<400> SEQUENCE: 20

```
cccggtgccc gaggtaggcg                                                    20

<210> SEQ ID NO 21
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 21
gcaccacttt gtacaagaaa gctgggcggc cgcttttttt ttttttttttt t               51

<210> SEQ ID NO 22
<211> LENGTH: 23
<212> TYPE: PRT
<213> ORGANISM: mouse

<400> SEQUENCE: 22

Glu Thr Ala Ile Val Val Ser Ile Val Ile Cys Ser Val Leu Leu Leu
1               5                   10                  15

Leu Ser Val Val Ala Leu Phe
            20

<210> SEQ ID NO 23
<211> LENGTH: 15
<212> TYPE: PRT
<213> ORGANISM: mouse

<400> SEQUENCE: 23

Phe Leu Glu Glu Gln Ala Glu Lys Arg Gly Ile Ser Asp Pro Asp
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide derived from mouse

<400> SEQUENCE: 24

Cys Phe Leu Glu Glu Gln Ala Glu Lys Arg Gly Ile Ser Asp Pro Asp
1               5                   10                  15
```

PLEXIN FAMILY-LIKE POLYPEPTIDE, AND USES THEREOF

BACKGROUND OF THE INVENTION

1. Field of the Invention

The present invention relates to a novel DNA and a gene comprising thereof, the DNA having Plexin-like sequence, being expressed specifically in vessels throughout all angiogenesis period from the beginning of angiogenesis in ontogenesis, being intensely expressed in stratified squamous epithelium in stomach of grown-up adults, being moderately expressed in uterus, and being expressed in various organs including brain; a novel polypeptide encoded by the DNA and a recombinant protein comprising the polypeptide; an antibody against the novel polypeptide; a screening method of an in vivo angiogenesis proliferation/differentiation control factor and compound which controls vascular cells proliferation/differentiation and is involved in inhibition of vascular proliferation which supports proliferation of cancer cells; and a measurement kit for the vascular proliferation/differentiation control activity of the differentiation control factor and compound.

2. Description of the Related Art

As the human genome project and the human cDNA project have successfully completed, many disease-related genes or candidates thereof have been identified. However, researches using human genes are limited due to ethical constraints, so that novel approach is being explored. In this circumstance, identification of homologous genes in model organisms is a crucial step to facilitate the research. Rodents, particularly mouse is a model organism which has been studied in depth so far. Relatively abundant data on genome or mutants of the mouse is available, but it is not still sufficient yet. On the other hand, as a means to analyze genes which are expressed in vivo, researches to analyze cDNA sequences randomly has been conducted, and the sequences of cDNA fragments identified in the researches have been registered as Expressed Sequence Tag (EST) in databases for publication. However, many EST has only limited data for base sequences of 100 bps to 500 bps in length. It is difficult to estimate the function of a base sequence from the data thus accumulated.

In various organs, physiological functions are regulated under control by many hormones, hormone-like substances, neurotransmitters, and physiologically active substances. Also, in the regulation of the physiological functions of various organs, proliferation, guidance and activation of specific cells responsible for the function is involved. Therefore, in order to develop a new drug, it is useful to obtain a novel gene which is specifically expressed in various organs, such as a gene expressed specifically in vessels throughout all angiogenesis period from the beginning of angiogenesis in ontogenesis, and to generate a protein which is encoded by this gene which regulates complicated functions in angiogenesis and various organs. Furthermore, in order to efficiently screen agonists and antagonists of a protein for the purpose of drug development, it is necessary to estimate the function of gene encoding the protein expressed in vivo using homology search, to generate a recombinant protein based on the information by expressing the gene in appropriate expression system, and to generate antibodies which specifically bind to the protein. In an experimental system which models angiogenesis using mouse ES cells, attempts have been made to comprehensively obtain genes involved in angiogenesis, and basic information is now being accumulated (document 14).

However, a gene which is involved in angiogenesis and has 4000 or more bps, has not been reported yet from rodents especially from a mouse.

In the Long Chain Human cDNA project, human KIAA0620 gene derived from human brain was reported (Ishikawa K., Nagase T., Suyama M., Miyajima N., Tanaka A., Kotani H., Nomura N. and Ohara, O., DNA Res., 1998, 5:169-176, Prediction of the coding sequences of unidentified human genes X. The complete sequences of 100 new cDNA clones from a brain which can code for large proteins in vitro., GenBank Accession No. AB014520, 6,754 bp, 1746aa, Homosapiens, cDNA, KIAA0620, Ohara O. et al.). Also it is reported that mRNA of a gene relating to human KIAA0620 is expressed in vascular endothelial cells or central nervous system (CNA) during development processes of a mouse (van der Zwaag, B. et al., Dev. Dyn., 2002, 225:336-343). But the function of the gene has not been identified.

Human KIAA0620 gene is located on the chromosome 3q21.3, and several SNPs of the human KIAA0620 gene are reported. As majority of human diseases are not caused by mere deletion of a specific gene, but by partial alteration in functions or activities of a protein by amino acid substitution, it is suspected that human KIAA0620 gene may be involved in healing of wound, healing of fracture, vascular occlusion and collateral vessel formation, periodic formation of vascular network in tunica mucosa uteri (transient or at the time of luteinization); various processes in which angiogenesis is undesirably involved such as proliferation of cancer cells, chronic articular rheumatism, diabetic retinopathy, endometriosis, obesity; and various processes in which angiogenesis is desirably involved such as heart attack, neurodegenerative diseases, circulatory deficits in legs, arteriosclerosis obliterans, and psoriasis vulgaris. Although it was reported that mRNA of the gene relating to human KIAA0620 gene is expressed in vascular endothelial cells or central nervous system (CNS) in a mouse during development process, researches using not human but experimental animals are essential to elucidate human KIAA0602 gene and its relationship. However, the gene that corresponds to human KIAA0620 gene has not been obtained yet from rodents particularly from a mouse which is an important model animal in researches of human pathology, thus a study that uses the gene could not have been conducted so far.

Non-Patent Document 1:1
Masashi Shibuya, 1999, Experimental Medicine, 17:712-715, Today's studies about angiogenesis and molecular regulatory mechanism Non-Patent Document 2:2
Masanori Hirashima, Shinichi Nishikawa, 1999, Experimental Medicine, 17:716-720, Embryology of vascular endothelial cells Non-Patent Document 3:3
Jun Yamashita, 2001, Experimental Medicine, 19:830-835, Angiogensis from embryonic stem cells Non-Patent Document 4:4
Nobuyuki Takakura, 2001, Experimental Medicine, 19:836-840, Vascular cells and angiogenesis Non-Patent Document 5:5
Chisa Sunami, Hiroyuki Shibata, Yuji Seki, 2001, Experimental Medicine, 19:841-846, Formation of cartilage and bone, and vascular invasion Non-Patent Document 6:6
Nariaki Matsuura, Yoshihisa Okazaki, Naoyuki Tani, Hidetoshi Eguchi, 1999, Experimental Medicine, 17:741-752, Angiogenesis inhibitors produced by tumor Non-Patent Document 7:7
Jane R. K. & Karmeri P. F., 2002, Nikkei Science, March issue, 22-29, Angiogenesis—new field of medicine Non-Patent Document 8:8
van der Zwaag, B. et al., Dev. Dyn., 2002, 225:336-343, PLEXIN-D1, a novel plexin family member, is expressed in vascular endothelium and central nervous system during mouse embryogenesis.

Non-Patent Document 9:9
Tamagnone L, Artigiani S, Chen H, He Z, Ming G I, Song H, Chedotal A, Winberg M L, Goodman C S, Poo M, Tessier-Lavigne M, Comoglio P M., 2001, Cell, 99:71-80, Plexins are a large family of receptors for transmembrane, secreted, and GPI-anchored semaphorins in vertebrates Non-Patent Document 10:10
Manahan, D., 1997, Science, 277:48-50, Signaling vascular morphogenesis and maintenance Non-Patent Document 11:11
Barinaga, M., 1997, Science, 275:482-484, Designing therapies that target tumor blood vessels Non-Patent Document 12:12
Asahara T, Murohara T, Sullivan A, Silver M, van der Zee R, Li T, Witzenbichler B, Schatteman G, Isner J M. Asahara, T. et al., 1997, Science, 275:964-967, Isolation of putative progenitor endothelial cells for angiogenesis Non-Patent Document 13:13
Risau, W., 1997, Nature, 386:671-674, Mechanisms of angiogenesis Non-Patent Document 14:14
Yamashita J, Itoh H, Hirashima M, Ogawa M, Nishikawa S, Yurugi T, Naito M, Nakao K, Nishikawa S., Flk1-positive cells derived from embryonic stem cells serve as vascular progenitors Non-Patent Document 15:15
Ishikawa K, Nagase T, Suyama M, Miyajima N, Tanaka A, Kotani H, Nomura N, Ohara O., 1998, DNA Res., 5:169-76, Prediction of the coding sequences of unidentified human genes X. The complete sequences of 100 new cDNA clones from brain which can code for large proteins in vitro Non-Patent Document 16:16
Tamagnone L, & Comoglio P M., 2000, Trends in Cell Biology, 10:377-383, Signalling by semaphorin receptors: cell guidance and beyond Non-Patent Document 17:17
Shimizu M, Murakami Y, Suto F, Fujisawa H, 2000, J. Cell Biol., 148:1283-1293, Determination of cell adhesion sites of neuropilin-1

DISCLOSURE OF THE INVENTION

Problem to be Solved by the Invention

Human KIAA0620 gene was obtained in the Human Long Chain cDNA project, but information on the gene itself was not satisfactory, and information on its function was not sufficient. That is, an experiment using human KIAA0620 gene as a probe to identify expression of human KIAA0620 related gene in a mouse during its development reported that mRNA of a gene which shows reaction to human KIAA0620 was expressed in vascular endothelial cells or central nervous system (CNS) in a mouse during its development. However, in order to study human KIAA0602 gene and a gene relating thereto in detail, a research using not human but experimental animals is essential. The gene that corresponds to human KIAA0620 gene has not been obtained yet from rodents such as a rat, a mouse or a hamster, particularly from a mouse which is an important model animal for a research of human pathology, due to difficulty. Thus a study that use the gene could not been conducted so far.

Therefore, it will be a very important means to obtain a novel gene relating to human KIAA0620 gene from rodents such as a rat, a mouse or a hamster, especially from a mouse and to obtain information on functions of the protein encoded by the novel gene of the invention, in order to detect a protein, an agonist or an antagonist which specifically bind to the polypeptide of the invention. Even if the protein specifically binding to the above-mentioned polypeptide cannot be detected, by analyzing the physiological function of the polypeptide of the invention by conducting inactivation experiments on the polypeptide (for example, producing recombinant animal cells or recombinant animals in which the gene is over-expressed or knocked-out), it will be possible to produce an agonist or an antagonist for the polypeptide of the invention. The protein, agonist or antagonist which specifically binds to the polypeptide of the invention can be used as a prophylatic, therapeutic or diagnostic drug to prevent, treat and diagnose a disease in which a function of the some organ in a patient is not in order.

In some cases, the decreased or increased function of the polypeptide of the invention in vivo may trigger a disease in various organs. In these cases, not only administration of a ligand and a ligand inhibitor, an antagonist and an agonist for the protein of the polypeptide, but also administration of the polypeptide or antibody which targets the above organs of the polypeptide of the invention, administration of an antisense nucleic acid against the gene which encodes the polypeptide and administration of short double strand RNA (RNAi) which is synthesized based on the gene sequence information of the gene, or a genetic therapy which uses the gene itself, can be devised. In these cases, the base sequence which encodes the polypeptide of the invention is essential information to identify presence or absence of deletion or mutation in the gene of a patient with a disease in various organs in which the polypeptide of the invention is involved. The gene encoding the polypeptide of the invention can be used in a prophylactic, therapeutic or diagnostic drug to prevent, treat or diagnose the diseases in which the dysfunction of the polypeptide of the invention is involved.

Means for Solving Problems

The inventors concentrated their efforts on the study with use of materials and screening methods completely different from conventional ones. And they finally succeeded in cloning a gene (DNA) which shows substantial homology to human KIAA0620 gene from cDNA library obtained from a mouse embryo tail bud. They found that the amino acid sequence of the polypeptide encoded by the gene is a novel sequence with 1,746 amino acid length and shows about 91.88% homology to the amino acid sequence of the polypeptide encoded by human KIAA 0620 gene, that the gene thus obtained is expressed specifically in vessels throughout all angiogenesis period from the beginning of angiogenesis in ontogenesis, and that the gene is intensely expressed in stratified squamous epithelium in stomach of grown-up adults, moderately expressed in uterus, and expressed in various organs including brain.

Furthermore, by using an experimental system which models angiogenesis using mouse ES cells and allows comprehensive acquisition of genes involved in the generation and proliferation of endothelial cells at early stage of angiogenesis, the gene of the invention is detected as a first large gene having more than 4,000 bps that is involved in the angiogenesis derived from a rodent, especially as a large gene derived from a mouse (document 2, 3, 14).

Furthermore, by analyzing gene information thus obtained, the inventors found that the polypeptide sequence of the invention has domains characteristic of the Plexin family. The inventors also suggested that the domains are associated with important functions such as angiogenesis, and proliferation, differentiation or guidance of cells constituting various organs, and obtained the novel polypeptide and antibody specific to the novel polypeptide based on the gene information. Furthermore, the inventors found that the region which defines extramembrane segment of the protein encoded by human or mouse KIAA0620 gene can inhibit angiogenesis, particularly inhibit normal construction of vascular network in retina. Based on the above findings, the inventors finally completed the invention.

The first aspect of the invention relates to a DNA comprising a base sequence encoding one of the following polypeptide (a) or (b):

(a) a polypeptide comprising the full length or a part of an amino acid sequence which is same or substantially same as an amino acid sequence represented by SEQ ID NO:1, SEQ ID NO:15 or SEQ ID NO:18, (e.g., novel Plexin family-like polypeptide as follows: a polypeptide comprising 1,745 amino acids from second amino acid (methionine) to 1,746th amino acid (alanine) in the amino acid sequence represented by SEQ ID NO:1; or a polypeptide comprising 1,996 amino acids from second amino acid (methionine) to 1,997th amino acid (alanine) in the amino acid sequence represented by SEQ ID NO:15) or, (b) a polypeptide comprising an amino acid sequence derived from an amino acid sequence represented by SEQ ID NO:1, SEQ ID NO:15 or SEQ ID NO:18 by deletion, substitution or addition of a part of the amino acids and having a biological activity substantially equivalent to the full length or a part of the polypeptide (a).

The second aspect of the invention relates to a DNA as set forth in one of the following (a), (b), or (c) wherein:

(a) a DNA which encodes full length or part of an amino acid sequence represented by SEQ ID NO:1 (5,238 base pairs from third to 5,240th base pair in SEQ ID NO:2), an amino acid sequence represented by SEQ ID NO:15 (5,991 base pairs from third to 5,993th base pair in SEQ ID NO:16), or an amino acid sequence represented by SEQ NO:18 (e.g., an amino acid sequence having at least one motif identified in novel Plexin sequence as set forth in below, or a polypeptide comprising 1,745 amino acids from second (methionine) to 1,746th (alanine) amino acid in the amino acid sequence represented by SEQ ID NO:1, or a polypeptide comprising 1,996 amino acid from second (methionine) to 1,997th (alanine) amino acid in the amino acid sequence represented by SEQ ID NO:15);

(b) a DNA which hybridizes with the DNA comprising a base sequence complementary to the DNA as set forth in (a) under a stringent condition; or (c) a DNA which hybridizes with the DNA comprising a base sequence complementary to the DNA as set forth in (a) under a stringent condition, and encoding a protein which has a biological activity substantially equivalent to the full length or part of the polypeptide (a).

The above DNA in the first and second aspects of the invention will be hereinafter referred to as "DNA of the invention." DNA of the invention encodes a novel polypeptide. The invention also relates to a gene comprising the DNA of the invention derived from rodents such as a rat, a mouse, or a hamster, particularly, a gene derived from a mouse. Particularly, such mouse gene is also referred to as "mouse (m) KIAA0620 gene" or "mpf00920 gene."

The invention also relates to the polypeptide (hereinafter referred to as "the polypeptide of the invention") encoded by the DNA or gene of the invention (hereinafter referred to as "KIAA0620 gene"), for example, polypeptide (hereinafter referred to as "KIAA0620 protein") which is a recombinant protein generated in host cells to which the DNA or gene of the invention is introduced. It is useful as a novel molecular marker for the vascular endothelial cells in the ontogenesis of rodents (Flk-1 positive cell: document 1, 10, 12, 14), and the cells on the way of differentiation from progenitors to the vascular endothelial cells. The polypeptide of the invention is also useful since it can provide a biomarker for angiogenesis, an amino acid sequence necessary in antibody production, or an angiogenesis inhibitor.

The invention also relates to a recombinant vector comprising the DNA or gene of the invention, the polypeptide or partial peptide of the invention (e.g., a polypeptide comprising a sequence of several to several dozen amino acids at the region near to C-terminal, as illustrated in the following examples), a recombinant protein comprising the polypeptide, or an antibody which specifically binds to the salt thereof.

Also, with use of the DNA, gene, polypeptide, recombinant protein, or antibody of the invention, the invention provides a screening method and a screening kit to screen a substance (ligand) which specifically binds to the polypeptide or recombinant protein of the invention, a ligand blocker, a chemical compound which alters the amount of the protein expressed, a chemical compound which alters the binding characteristics to the protein (antagonist and agonist).

Furthermore, the invention produces transgenic cells or a transgenic animal in which the recombinant vector of the invention is introduced, to provide in vitro or in vivo animal model of various diseases.

Furthermore, the invention provides a screening method and various screening kits for the method which use the DNA, gene, polypeptide, recombinant protein, recombinant animal, recombinant animal cell or antibody of the invention, to screen a vascular proliferation and differentiation control factor or a control compound (including synthetic compound). Particularly, the invention provides a screening method which uses the DNA or gene of the invention to screen a vascular proliferation and differentiation control factor or control compound, and a gene expression measurement kit used in the method; a screening method to screen a vascular proliferation and differentiation control factor or control compound based on a protein-protein interaction detection system or an agonist, antagonist, in vivo ligand detection system prepared by using the polypeptide or recombinant protein of the invention, and a polypeptide binding substance measurement kit used in the method; a screening method which uses a recombinant animal or recombinant animal cells to screen a vascular proliferation and differentiation control factor or control compound, and a vascular proliferation and differentiation control activity measurement kit used in the method; and a screening method to screen a vascular proliferation and differentiation factor or control compound based on a protein-protein interaction detection system or an agonist, antagonist, in vivo ligand detection system prepared by using the antibody of the invention, and an antibody titer measurement kit used in the method.

Furthermore, the invention provides a method to manufacture the polypeptide of the invention, a recombinant protein comprising the polypeptides and salt thereof, and a recombinant protein or salt thereof comprising full length or a part of the polypeptide of the invention thus obtained, characterized in, culturing a transformant comprising the DNA of the invention, a recombinant vector or an expression vector comprising the DNA of the invention; generating and accumulating the recombinant protein comprising full length or a part of the polypeptide of the invention, and collecting the protein. Furthermore, the invention provides a medicine comprising the DNA of the invention, an antisense nucleotide having a base sequence substantially complementary to the DNA which encodes the recombinant protein comprising the polypeptide of the invention or partial peptide thereof, a medicine comprising the antisense nucleotide, a short double strand RNA (RNAi) which is synthesized based on the sequence information of the DNA of the invention, a medicine comprising the short double strand RNA, and a medicine comprising the recombinant protein containing the polypeptide of the invention or partial peptide thereof.

Furthermore, the invention relates to so-called DNA chip (array) or protein chip, which can be produced by comprehensively generating and accumulating the DNA of the invention, the polypeptide of the invention, the recombinant protein comprising the polypeptide or partial peptide thereof, or antibody against the DNA or gene of the invention.

ADVANTAGE OF THE INVENTION

This time, the inventors used cDNA library derived from a mouse embryo tail bud and a special screening method, and successfully cloned a gene (DNA) having significant homology to human KIAA0620 gene which could not been obtained so far, and obtained a DNA sequence which encodes the novel Plexin polypeptide. The polypeptide encoded by the novel DNA sequence has 1,746 or 1,997 amino acid length, and a novel structure in that has Semaphorin/CD100 antigen domain, three Plexin/Semaphorin/integrin domains, three cell surface receptor IPT/TIGs, and a transmembrane segment on the C-terminal side. The polypeptide is suspected to be involved in various processes of essential for cells including proliferation, differentiation and expression of the function of vascular endothelial cells.

Furthermore, it has been first found that the gene sequence of the invention is expressed specifically in vessels throughout all angiogenesis period from the beginning of angiogenesis in ontogenesis, being intensely expressed in stratified squamous epithelium in stomach of grown-up adults, being moderately expressed in uterus, and being expressed in various organs including brain; and a possibility has been indicated that the polypeptide encoded by the gene of the invention might be involved in essential functions in angiogenesis, development and preservation of functions in various organs including brain, and diseases in which angiogenesis plays some roles in various organs.

Furthermore, it was found that the novel polypeptide corresponding to the extramembrane segment of mouse KIAA0620 protein expressed in various organs including brain, can inhibit angiogenesis, particularly, inhibit normal construction of the vascular network of the retina. That is, it was found that the recombinant Plexin is a transmembrane protein, that the extramembrane segment of the recombinant Plexin generated by expressing the extramembrane segment can inhibit angiogenesis, that the protein generated by gene recombination using mammalian cells as a host can be administered to a neonatal ICR mouse to inhibit the normal construction of the vascular network of the retina thereof, and that the extramembrane segment of recombinant Plexin has a function associated to the angiogenesis of the vascular network of retina.

BRIEF DESCRIPTION OF THE DRAWINGS

FIG. 3A1 illustrates expression sites of mpf00920 (mouse KIAA0620) gene in the sagittal direction of fetus frozen section14.5 days after fertilization detected by the in situ method. The top view illustrates an image detected by the negative control using a sense probe. FIG. 3A2, illustrates expression intensity of mpf00920 gene detected by using an antisense probe (expression sites are represented by deep stained region).

FIG. 4B illustrates expression sites of mpf00920 (mouse KIAA0620) gene represented by mRNA level in a paraffin section of a cerebrum of an adult mouse detected by the in situ method. The cerebral neuroglia cells are deeply stained.

FIG. 4C illustrates expression sites of mpf00920 (mouse KIAA0620) gene represented by mRNA level in a paraffin section of a cerebellum of an adult mouse detected by the in situ method. The cerebellar Purkinje cell layer is deeply stained.

FIG. 5 is a photograph showing electrophoresis which compares expression frequency of mouse KIAA0620 gene in mouse fetus development process represented by mRNA level detected by RT-PCR method. The top view illustrates expression intensity of Flk1 gene used as a control, and the bottom view illustrates the expression intensity of mouse KIAA0620 gene. The expression intensity is represented by ethidium bromide staining pattern after fractioning by agarose electrophoresis.

FIGS. 8 A-B are photographs that show the result of Western blot analysis of the whole protein fraction and the hydrophobic fraction extracted from the whole protein fraction. The protein was generated by using HEK 293 cells as a host, and expressing the mouse KIAA0620 full length—V5 fusion protein and a mouse extramembrane segment containing transmembrane segment (TM), that is, mouse KIAA0620 extramembrane segment (TM)—V5 fusion protein. In the figure, 1 represents the analysis result of the whole protein fraction prepared from the control cells, 2 represents that of the hydrophobic protein fraction prepared from the control cells, 3 represents that of the whole protein fractions prepared from the cells which express mouse KIAA0620 full length—V5 fusion protein, 4 represents that of the hydrophobic protein fraction from the cells which express mouse KIAA0620 full length—V5 fusion protein, 5 represents that of the whole protein fraction prepared from the cells which express mouse KIAA0620 extramembrane segment (TM)—V5 fusion protein, and 6 represents that of the hydrophobic protein fraction prepared from the cells which express mouse KIAA0620 extramembrane segment (TM)—V5 fusion protein. The photograph on the left.

FIGS. 9 A-D are microscopy photographs which show the result of the experiment to inhibit development of retinal vessels in a neonatal mouse using mouse KIAA0620 extramembrane segment—IgG1Fc fusion protein five hours after the injection on the fifth day after the birth). Five hours after injection into the eyeball, excessive formation of filopodia was observed in the retinal blood vessels on the way of development, especially in the endothelial cells at the leading end of developing vessels (FIG. 9C), (FIG. 9D): mKIAA0620 extramembrane segment-Fc). On the other hand, no change was observed in the eyeball of a mouse to which only IgG1Fc protein was injected (FIG. 9A), (FIG. 9B)(Fc).

FIGS. 10 A-B are microscopy photographs which show the result of an experiment to inhibit development of retinal vessels in a neonatal mouse using mouse KIAA0620 extramembrane segment—IgG1Fc fusion protein (three days after the injection which was performed one day after the birth). Three days after the injection into the eyeball, the construction of vascular network of retina was significantly disturbed (FIG. 10B, mKIAA0620 extramembrane segment-Fc). On the other hand, no change was observed in the eyeball of a mouse to which only IgG1Fc protein was injected (FIG.10A : Fc).

BEST MODE FOR CARRYING-OUT OF THE INVENTION

Figure 1:
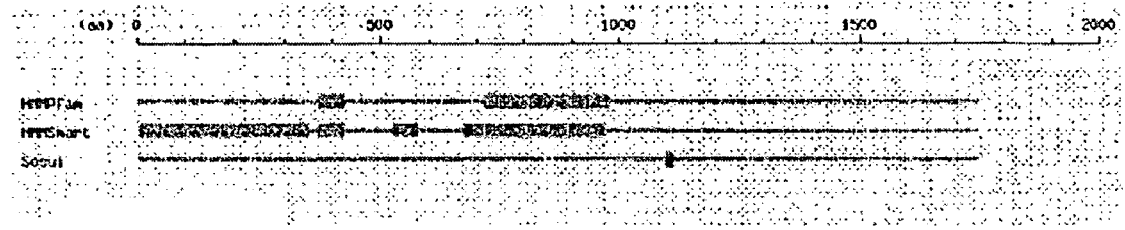
FIG. 1 illustrates Semaphorin/CD100 antigen domain, three Plexin/Semaphorin/integrin domains, three cell surface receptor IPT/TIG domains, and a transmembrane (TM) segment identified in novel Plexin polypeptide of the invention (aa: amino acid sequence (SEQ ID NO. 18) wherein the figure represents the number of amino acids. Box: domains and transmembrane (TM) segment identified by different search methods. Searches used are, from top to bottom, HMMPfam search, HMMSmart search, and Sosui search). From these results, novel Plexin polypeptide (SEQ ID NO. 18) was identified by HMMPfam search, HMMSmart search, and Sosui search.

The base sequence of the DNA of the invention is sequenced and identified from the cDNA segment isolated from the cDNA library prepared with use of mRNA as a starting material, derived from a mouse embryo tail bud collected by the inventors. Particularly, about 16,608 recombinants were selected from a cDNA library derived from a mouse embryo tail bud prepared according to (DNA Research, 2002, 9:47-57 and Nucleic Acids Res., 29, e22 (2001)), the 3'-terminal of all the recombinants were sequenced, and clones having high homology to human KIAA0620 gene were selected to sequence all bases thereof. Next, based on all the base sequences thus obtained, homology search was conducted using a DNA analysis program (GCG, Fasta & Blast). With great effort, the inventors could finally obtain the DNA of the invention which could not have been obtained due to difficulty.

The inventors tried to obtain genes having homology to human long-chain cDNA (KIAA0620) in the cDNA library derived from a mouse embryo tail bud, and surprisingly, succeeded in obtaining a clone (clone name: mpf00920) which has a base sequence (SEQ ID NO:2) containing a novel gene which encodes a novel polypeptide (the polypeptide of the invention) having novel 1,746 amino acid sequence (SEQ ID NO:1) which shows about 91.88% homology at the amino acid sequence level to the amino acid sequence of polypeptide encoded by human KIAA0620 gene.

The amino acid sequence (1,746 amino acid length) from the first amino acid to the 1,746th amino acid in the amino acid sequence represented by SEQ ID NO:1 of the invention has significant homology (about 91.88%. 1,748 amino acids from the 238th amino acid to the 1,985th amino acid of the of 1,985 amino acids) to approximately full length of the amino acid sequence encoded by human KIAA0620 gene (1,985 amino acids).

As described in the below examples, homology search was conducted by using public database, on the above amino acid sequences obtained by the invention, to find that full length of 1,746 amino acid of the "polypeptide of the invention" has relatively high homology of about 91.70% and about 91.51% to the two sequences applied so far. However, these sequences applied so far were derived from human. The invention is first to obtain the gene equivalent to human KIAA0620 gene from rodents, particularly from a mouse, which is an important model animal to elucidate the pathology of the human. Thus, by characterizing "the polypeptide of the invention" encoded by the gene, the characteristics and function of the protein having this novel sequence can be described for the first time.

The plasmid containing a DNA having a base sequence represented by SEQ ID NO:2 of this invention (plasmid name: mpf00920) was deposited to International Patent Organism Depositary of the National Institute of Advanced Industrial Science and Technology, 1-1-1 Central 6, Higashi, Tsukuba-shi, Ibaraki-ken on Sep. 10, 2003, and accession number FERMP-19518 was assigned thereto. The plasmid was transferred to the international deposition based on Budapest Treaty on the international recognition of the deposit of microorganisms for the purpose of patent procedures and regulations on Oct. 25, 2004, and accession number FERM ABP—10154 was assigned thereto.

Human KIAA0620 gene sequence is 6,754 bps, and the polypeptide encoded by the gene has 1,985 amino acid length (DNA Research, 1998, 5:169-176, http://www.kazusa.or.jp/huge/gfpage/KIAA0620/, NCBI-GenBank Accession No. AB014520). By examining human KIAA0620 gene homologues in detail, it is possible to examine the possibility that any polypeptide is encoded on the N-terminal side. Although the amino acid sequence of the polypeptide encoded by the DNA represented by SEQ ID NO:2 of the invention has 1,746 amino acids, by examining homologues of the DNA of the invention, any polypeptide encoded on the extension of N-terminal side may be identified.

Persons skilled in the art may prepare some appropriate primer (e.g., 5'-CCCGGTGCCCGAGGTAGGCG-3' (SEQ ID NO. 20) synthesized in correspondence with 5'-CGC-CTACCTCGGGCACCGGG-3' which is a segment from the 61st bp to 80th bp in the SEQ ID NO:2), hybridize the primer with commercially available mRNA derived from rodents, or with mRNA prepared from tissues derived from rodents, then carry out reverse transcription, to specifically synthesize a novel cDNA fragment containing a upstream region (5'-terminal side of the gene) of the DNA of the invention. By inserting the novel cDNA fragment containing the synthetic 5'-terminal region into a plasmid, and carrying out homology cloning such as colony hybridization with use of a part of the sequence SEQ ID NO:2 as a probe, the whole sequence of KIAA0620 gene derived from rodents containing the DNA of the invention can be prepared. Alternatively in other methods, for example, by using the DNA of this invention as a probe, and carrying out homology cloning such as colony hybridization, the 5'-terminal region of KIAA0602 gene derived form various rodents including mouse can be prepared.

In fact, in order to enable high-throughput search of lengthy text sequence such as long-chain cDNA of the mammalian genome sequence, the inventors made effort to develop a computer (hardware) and design of control algorithm which can perform parallel comparison in which the computation time is independent from length of given sequence, with use of content addressable memory (CMA) in which comparators are attached to a memory based on Japanese published unexamined application No. 2003-216615. The inventors established novel system having improved performance such as super parallel genome comparator, and completed an analysis method targeting long-chain cDNA. Then the inventors used the super parallel genome comparator to carry out extensive and high-throughput base sequence search of mouse mKIAA0620 from the published mouse genome sequence, searched information of sequences which can be added to mKIAA0620 base sequence from the published mouse genome sequences, and designed a primer sequence necessary for acquisition of amino acid sequence which can be added to the N-terminal of the amino acid sequence represented by SEQ ID NO:1 of the invention. By using the PCR methods such as 5'RACE with use of these primers, novel amino acid sequence having 251 amino acids which can be newly added to the N-terminal could be determined, as described in the example of the specification.

For the DNA of the invention, any DNA can be applicable provided that it comprises a base sequence which encodes the polypeptide of the invention as above. For example, any cDNA identified and isolated from the cDNA libraries derived from various organs of rodents such as a brain, a heart, a lung, a liver, a spleen, a kidney, a testicle, a thymus, muscle, and a bone marrow, or various tissue and cells at each stage of development, or any synthetic DNA, is applicable. The vector used for generating the library may be any suitable vector including bacteriophage, plasmid, cosmid, and phagemid. Or, the DNA can be multiplied by direct Reverse Transcriptase Polymerase Chain Reaction (hereafter abbreviated as "RT-PCR") with use of totalRNA fraction or the mRNA fraction prepared from any of above mentioned cells and tissues, or cytoplasm thereof.

The term "amino acid sequence substantially identical to the amino acid sequence represented by SEQ ID NO:1, NO:15 or NO:18" means an amino acid sequence which are at least about 92.5% homologous, preferably at least about 95% homologous, and more preferably at least about 98% homologous in average to the full length of amino acid sequence represented by SEQ ID NO:1, SEQ ID NO:15 or SEQ ID NO:18. Therefore, the polypeptides comprising amino acid sequences substantially identical to the amino acid sequence represented by SEQ ID NO:1, SEQ ID NO:15 or SEQ ID NO:18 of the invention includes polypeptides which have above mentioned homology to the amino acid sequence represented by SEQ ID NO:1, SEQ ID NO:15 or SEQ ID NO:18, and have a biological activity substantially equivalent to the polypeptide comprising an amino acid sequence represented by SEQ ID NO:1, SEQ ID NO:15 or SEQ ID NO:18. The term "substantially equivalent" means that the activity is equivalent in quality. Furthermore, the polypeptide of the invention include a polypeptide comprising an amino acid sequence derived from the amino acid sequence represented by SEQ ID NO:1, SEQ ID NO:15 or SEQ ID NO:18 by deletion, substitution or addition of a part of the amino acids (preferably about 1 to 20 amino acids, more preferably about 1 to 10 amino acids, more preferably about several amino acids) or amino acids combining thereof, and having a biological activity substantially equivalent to the polypeptide comprising an amino acid sequence represented by SEQ ID NO:1, SEQ ID NO:15 or SEQ ID NO:18.

Furthermore, the DNA of the invention includes any DNA which hybridizes with DNA encoding the amino acid sequence represented by SEQ ID NO:1 SEQ ID NO:15 or SEQ ID NO:18 derived from the base sequences represented by SEQ ID NO:2, SEQ ID NO:16 or SEQ ID NO:19, or a DNA comprising base sequences complementary to the base sequence of the DNA, under stringent conditions, and preferably encodes polypeptide (protein) which has a biological activity substantially equivalent to the polypeptide comprising an amino acid sequence represented by SEQ ID NO:1 or SEQ ID NO:15. The DNA which can hybridize with the DNA comprising a base sequence complementary to the base sequence of the DNA encoding the amino acid sequence represented by SEQ ID NO:1, SEQ ID NO:15 or SEQ ID NO:18 derived from the base sequence represented by SEQ ID NO:2, SEQ ID NO:16 or SEQ ID NO:19 includes a DNA comprising a base sequence which is at least about 87.5% homologous, preferably at least about 90% homologous, more preferably at least about 95% homologous to the DNA as average. Hybridization can be performed according to one of suitable methods known in the art, e.g., that described in Molecular cloning third ed. (Cold Spring Harbor Lab. Press, 2001) or any suitable method equivalent thereto. When using a commercially available library, hybridization can be performed according to the instruction attached thereto. The term "stringent condition" means a condition wherein if the probe is labeled by DIG DNA Labeling (Boehringer Mannheim Cat No. 1175033), the sequence can hybridizes with human DNA probe of the invention in Southern blot hybridization under the condition that sequence is hybridized in DIG Easy Hyb solution at 32° C. (Boehringer Mannheim Cat No. 1603558), and the membrane is washed in the 0.1×SSC solution at 40° C. (containing 0.1%[w/v]SDS. 1×SSC is 0.15M NaCl, 0.015M sodium citrate).

The method to clone the DNA of the invention includes PCR method wherein the DNA is multiplied by using synthetic DNA primer having an appropriate base sequence such as that encodes a part of the polypeptide of the invention, or clone can be selected through hybridization between a DNA incorporated in appropriate vector and a labeled DNA fragment or a synthetic DNA which encodes full length or a part of the polypeptide of the invention. The hybridization can be performed according to a method described in Molecular cloning third. ed. (Cold Spring Harbor Lab. Press, 2001), for example. When using a commercially available library, hybridization can be performed according to the instruction attached thereto. The base sequence of the DNA can be converted using one of suitable methods well-known in the art including Gapped duplex method, Kunkel method, or other methods equivalent thereto, with use of Super Script II reverse transcriptase kit (GIBCO BRL Co., LTD.). The cloned DNA which encodes the polypeptide can be used without change, after digestion by restriction nucleases, or after addition of appropriate linkers, as desired. The DNA may have triplet ATG as a translation initiation codon on the 5'-terminal side, and triplet TAA, TGA, or TAG as a translation stop codon on the 3'-terminal side. These translation initiation codon and translation stop codon can also be added using a suitable synthetic DNA adapter.

The expression vector of the polypeptide of the invention can be produced according to one of suitable methods well-known in the art. For example, the vector can be produced by (1) isolating a DNA fragment comprising the DNA of the invention, or a DNA fragment comprising a gene derived from rodents containing DNA of the invention, and (2) linking the DNA fragment to downstream of the promoter of an appropriate expression vector. As an expression vector, an expression vector using plasmid, such as plasmid from E. coli (e.g., pBR322, pBR325, pUC18, pUC118), plasmid from bacillus subtlis (e.g., pUB110, pTP5, pC194) and plasmid from yeast (e.g., pSH19, pSH15); bacteriophage such as λphage; or a sequence from animal virus such as SV40, CMV virus, retrovirus, vaccinia virus, baculovirus and bovine papiloma virus, can be used. Any promoter can be applicable to the invention provided that it is compatible with the host to be used for gene expression. For example, when the host is E. coli, preferable promoters include trp promoter, lac promoter, recA promoter, λPL promoter, lpp promoter, T7 promoter and any combination or composition thereof. When the host is bacillus subtilis, preferable promoters include SPO1 promoter, SPO2 promoter and penP promoter. When the host is yeast, preferable promoters include PHO5 promoter, PGK promoter, GAP promoter and ADH promoter. When using animal cells as a host, preferable promoters include SRα promoter, SV40 promoter, LTR promoter, CMV promoter, HSV-TK promoter, HSP promoter and metallothionein promoter.

Additionally, to the expression vector, many elements known in the art including enhancer, splicing signal, poly(A) addition signal, selection marker, SV40 replication origin (hereafter abbreviated as SV40ori) can be added. The protein encoded by the DNA of the invention can be expressed as a fusion protein with other protein (e.g., glutathion S transferase, histidine tag, calmodulin binding protein, protein A).

Such fusion protein can be cut using suitable protease, to be divided into each protein.

As the expression vector to be used for gene insertion to animal cells for the purpose of producing recombinant animal cells, the expression vectors as described above and vectors known in the art can be used that have Bluescript SK (+/−) vector as a template and linking Tie2 promoter (a promoter specific to vascular endothelial cells) in order to ensure expression specific in vascular endothelial cells. Endothelial cell specific expression can be achieved by using these expression vectors and promoters. Alternatively, a cloning system known as GATEWAY® cloning technology (Invitrogen: Cat. No. 11821-014) can also be used.

As host cells, escherichia, bacillus, yeast, insect cells, insects and animal cells are used, for example. Examples of the escherichia include, DH1 (Proc. Natl. Acad. Sci. USA, vol. 60, 160 (1968)), JM103 (Nucleic Acids Research, vol. 9, 309 (1981)), JA221 (Journal of Molecular Biology, vol. 120, 517 (1978)), and HB101 (Journal of Molecular Biology, vol. 41, 459 (1969)), derived from Escherichia coli K12, and a Escherichia coli B strain.

As bacillus, bacillus subtilis MI 114 (Gene, vol. 24, 255 (1983)), or 207-21 (Journal of Biochemistry, vol. 95, 87 (1984)) is used, for example. As yeasts, Saccharomyces cerevisiae AH22 and AH22R-, NA87-11A, DKD-5D, 20B-12, Schizosaccharomyces pombe NCYC1913, NCYC2036, or Pichia pastoris is used, for example. As animal cells, COS-1 or COS-7 from monkey kidney cells, Vero cells, Chinese hamster CHO cells (hereinafter abbreviated as CHO cells), dhfr knocked-out Chinese hamster cells CHO (hereinafter abbreviated as CHO (dhfr-) cells), mouse L cells, mouse AtT-20, mouse myeloma cells, rat GH3 cells, HEK293T cells, human FL cells, human Hela cells and human myeloma cells are used, for example.

As the expression vector to be used for gene insertion to animal cells for the purpose of producing recombinant animal cells, cultivated mouse embryonic stem cells, mouse fertilized ova, mouse NIH 3T3 cell strain, human fetus renal cell derived 293 cell strain, are used, for example.

The transformation of these host cells can be performed according to one of suitable methods well-known in the art. For example, reference can be made to the following documents. Proc. Natl. Acad. Sci. USA (vol. 69, 2110-, 1972), Gene (vol. 17, 107-, 1982), Molecular & General Genetics (vol. 168, p 111-, 1979), Methods in Enzymology (vol. 194, p 182-187, 1991), Proc. Natl. Acad. Sci. USA (vol. 75, 1929-, 1978), Cell Technology Separate Volume 8, New cell technology experiment protocol (p 263-267, 1995, Shujunsha) and Virology (vol. 52, 456-, 1973).

The transformation of the host animal cells for the purpose of transformation of transgenic animal can be performed according to one of suitable methods well-known in the art. For example, reference can be made to the following documents. Proc. Natl. Acad. Sci. USA (vol. 77, p 7380-7384, 1980), Experimental Medicine Separate Volume, The latest technology of gene targeting (p 34-41, 2000, Yodosha Co. Ltd.), Mouse manipulating manual 2nd ed. (p 225-252, p 279-285, 1994, Kindai Shuppan Co., Ltd.), Experimental Medicine Extra Issue, Developmental engineering experiment method (total 196 pages, 1994, Yodosha Co., Ltd.), and Trend in Genetics (vol. 5, p 70-76, 1989).

Particularly, the micro injection method is used for transgenic-mouse production. To a female mouse to collect ova therefrom (mouse strain C57BL/6, C3H BDF1), pregnant mare serum (5 units) is injected intraperitoneal, and 48 hours after the injection, human chorionic gonadotropin (5 units) is injected intraperitoneal to induce ovulation. As ovulation occurs 14 hours after the hormone injection, the female mouse is made to copulate with a male mouse during this period. A female mouse is checked for vaginal plug to confirm copulation and sacrificed, and fertilized ova are extracted from the ampulla of uterine tube. The fertilized ova thus extracted are put into a petri dish containing culture fluid, and a target gene is injected in the anterior nucleus of fertilized ova using a micromanipulator under a microscope. After injection of the target gene, surviving fertilized ova are introduced into oviduct of a pseudopregnancy mouse. About 20 days after introduction of fertilized ova, neonatal mice (transgenic mice) can be obtained.

In order to produce knockout mouse, the target gene is introduced to the cultured mouse ES cells using the electric boring method, cells in which homologous recombination has occurred are selected, ES cells thus selected are injected into other blastocysts, and resulting blastocysts are introduced in the oviduct of a foster dam to produce chimeric mouse. In this method, it is necessary to separate ES cells in which homologous recombination has occurred, from ES cells in which no gene was introduced or ES cells in which gene was introduced randomly. As a selection marker gene for this purpose, neomycin resistant gene is used. This gene is inserted between the homology regions. The success or failure of homology recombination is confirmed using Southern blot and PCR to determine that if the DNA fragment is detected. Alternatively, the positive and negative selection method can be used. In this case, unlike the method as above, a promoter must be added to the neomycin resistance gene. In order to separate from cells in which gene is randomly inserted, a thymidine kinase gene derived from herpesvirus or a diphteria toxin fragment A gene is used as a second selection marker gene. Cells in which homology recombination of the target gene has not been occurred can be killed by Ganciclovir addition or expression of diphteria toxin fragment A. When colonies are identified about 10 days from the beginning of cultivation, clones in which homology recombination has occurred can be identified using Southern blot or PCR. The identified ES cell clones are injected into blastocyst of a recipient using microinjection, and introduced into the uterus of a foster dam. About 20 days after introduction of ES cells, neonatal mice (reproductive chimeric mice) can be obtained.

The transformant thus obtained in which transformation is performed using expression vectors comprising a gene derived from rodents containing the DNA of the invention can be cultured according to one of suitable methods known in the art. For example, when the host is *Escherichia*, cultivation can usually be performed at about 15 to 43 C for about 3 to 24 hours, and aeration or agitation can be performed as necessary. When the host is *Bacillus*, cultivation can usually be performed at about 30 to 40 C for about 6 to 24 hours, and aeration or agitation can be performed as necessary. When the transformant using yeast as a host is cultured, cultivation can usually be performed using medium adjusted about 5 to 8 pH, at about 20 to 35 C for about 24 to 72 hours, and aeration or agitation can be performed as necessary. When the transformant using animal cells as a host is cultured, cultivation can usually be performed using medium adjusted to about 6 to 8 pH, at about 30 to 40 C for about 15 to 60 hours, and aeration or agitation can be performed as necessary.

In order to isolate and purify the polypeptide of the invention from the above culture, fungus or cells are collected after cultivation using one of known methods, the collected fungus or cells are suspended in appropriate buffer and destroyed using ultrasonic wave, lysozyme and/or freeze-thaw, then separated by centrifugation or filtering, to obtain crude extract of the protein. The buffer may contain protein denaturation agents such as urea and guanidine hydrochloride, or surfactants such as Triton X-100™. In the case the protein is secreted in the culture, fungus or cells and a supernatant are separated using one of known methods after cultivation in order to collect the supernatant. The culture supernatant, or a protein contained in the extract, which are obtained according to the above method, can be purified using appropriate combination of a known separation method and purification method. The polypeptide (protein) of the invention thus obtained can be converted to salt using one of known methods or methods equivalent thereto. Alternatively, when the polypeptide is obtained as salt, it can be converted into free substance or other salt using one of known methods or methods equivalent thereto. Before or after purification, any modification can be carried out on the amino acid in the protein generated by the recombinant, by removing methionine at N-terminal using methionine amino peptidase, myristoylation of N-terminal amino acid using myristoyl transferase, acetylation of N-terminal amino acid using acetyltransferase, or other modification using other modification enzymes. C-terminal amino acid of the protein can be modified by action of processing carboxyl peptidase or C-terminal amidase which modifies C-terminal. The polypeptide can be partially removed by action of appropriate limited protease such as trypsin, chymotrypsin, Factor Xa, thrombin, or KEX2 protease.

In the case that the protein is generated as a fusion protein, unnecessary polypeptide portions can be removed using appropriate limited protease.

Existence of the polypeptide (protein) of the invention or salt thereof, can be determined by various binding assays or enzyme immunoassays using specific antibodies.

The C-terminal of the polypeptide (protein) of the invention is typically carboxyl group (—COOH) or carboxylate (—COO—), however, C-terminal may be amide (—CONH$_2$) or ester (—COOR). In case of ester, one from the followings is used as R: $C_{1-6}$ alkyl group such as methyl, ethyl, n-propyl, isopropyl and n-butyl; C3-8 cycloalkyl group such as cyclopentyl and cyclohexyl; C6-12 aryl group such as phenyl and α-naphthyl; C7-14 aralkyl group such as phenyl-C1-2 alkyl group such as benzyl and phenetyl or α-naphthyl-C1-2 alkyl group such as α-naphthylmethyl; and pivaloyloxymethyl which is used widely as ester for oral administration.

When the polypeptide (it exists as protein) of the invention has carboxyl groups (or carboxylate) at sites other then its C-terminal, a protein having the amidated or esterified carboxyl group will also be included by the protein of the invention. In this case, C-terminal ester as described above is used as ester, for example. The protein of the invention includes a protein in which the amino group of the N-terminal methionine residue is protected by a protective group (e.g., C1-6 acyl group such as formyl group and acetyl group), a protein in which N-terminal glutamine residue which is generated by cutting in vivo is converted to pyroglutamic acid, a protein in which OH, COOH, NH$_2$, SH on the side chain of the amino acid in the molecule is protected by an appropriate protective group (e.g., C1-6 acyl group such as formyl group and acetyl group), or a fusion protein such as so-called glycoprotein having sugar chain bound thereto.

A peptide comprising a part of the polypeptide of the invention may be any polypeptide provided that it is a partial peptide of the polypeptides of the invention as above (the polypeptide exists as protein) and that it has a biological activity substantially equivalent to the polypeptide of the invention. For example, a peptide that has an amino acid sequence comprising at least 20 amino acids, preferably at least 50 amino acids, more preferably at least 70 amino acids, more preferably at least 100 amino acids, most preferably at least 200 amino acid in the amino acid sequence constituting the polypeptide (protein) of the invention, and biological activity substantially equivalent to the recombination protein of the invention, is used. Examples of this partial polypeptide include a polypeptide that contains a motif characteristic of novel Plexin in the amino acid sequence represented by SEQ ID NO:1, and a polypeptide that comprises 1,745 amino acids from second amino acid (methionine) to 1,746 amino acid (alanine) in the amino acid sequence represented by SEQ ID No:1. The C-terminal of the partial peptide of the invention is typically carboxyl group (—COOH) or carboxylate (—COO—), however, C-terminal may be amide (—CONH$_2$) or ester (—COOR), similar to the proteins of the invention as above. Additionally similar to the protein of the invention as above, the partial peptide of the invention includes a peptide in which the amino group of the N-terminal methionine residue is protected by a protective group, a peptide in which a glutamyl group generated by cutting N-terminal in vivo is converted to pyroglutamic acid, a peptide in which a substituent on the side chain of the amino acid in the molecule is protected by an appropriate protective group, or a fusion peptide such as so-called glycopeptide having sugar chain bound thereto.

The salt of a peptide comprising the polypeptide of the invention (it exists as protein) or part thereof may preferably be physiologically acceptable acid addition salt. Such salt includes salt of inorganic acid (e.g., hydrochloric acid, phosphoric acid, hydrobromic acid, sulfuric acid) or salt of organic acid (e.g., acetic acid, formic acid, propionic acid, fumaric acid, maleic acid, amber acid, tartaric acid, citric acid, malic acid, oxalic acid, benzoic acid, methansulfonic acid, benzenesulfonic acid).

The polypeptide (it exists as a protein) of the invention, a peptide comprising a part thereof, salt thereof, or amide thereof can be prepared using one of chemical synthesis methods known in the art. For example, using commercially available resin for protein synthesis, amino acids in which α-amino groups and functional groups on the side chain are appropriately protected are condensed on the resin in the order according to the sequence of the target protein using various condensations method known in the art. At the end of the reaction, the target protein is cut off from the resin, various protective groups are removed, and intramolecular disulfide bond formation reaction is performed in high diluted solution, to obtain a target protein, a target partial peptide thereof, or a target amide thereof. For the condensation of the above-mentioned protective amino acid, various activation reagents which can be used for the protein synthesis can be used including carbodiimides such as DCC, N,N'-diisopropyl carbodiimide, N-ethyl-N'-(3-dimethylaminoprolyl) carbodiimide. This activation can be conducted by directly adding the protective amino acid together with a racemization control additive (e.g., HOBt, HOOBt) to resin, or, the protective amino acid can be added to the resin after its activation with an acid anhydride, HOBt ester, or HOOBt ester.

As solvent to be used for activation of the protective amino acid or for condensation of the protective amino acid to the resin, appropriate solvent known in the art which can be used for protein condensation reaction can be selected. Such solvents include acid amides, halogenated hydrocarbons, alcohols, suloxides and ethers. Reaction temperature can be selected appropriately from a range which can be used for protein binding formation reaction. Typically, appropriate temperature in the range of about −20 to 50° C. will be selected. Typically, 1.5 to 4 folds excessive activated amino acid derivative is used. As a result of the test using ninhydrin reaction, when the condensation is inadequate, sufficient condensation can be obtained by repeating condensation reaction without need for desorption of the protective group. If sufficient condensation cannot be obtained even after repeated condensation reaction, unreacted amino acid can be acetylated using acetic anhydride or acetylimidazole to avoid any effect on the next reaction. Any group usually used in the art can be used as a protective group for amino group, carboxyl group, and serine hydroxyl group as materials. The protection of the functional groups which should not be involved in reaction of the material, and activation of the functional group involved in desorption or reaction of the protective group can be conducted with use of one of groups or means known in the art.

The peptide comprising a part of this invention or its salt can be produced according to an appropriate peptide synthesis method known in the art, or by cutting the protein of the invention with a suitable limited protease. As a peptide synthesis method, solid phase synthesis and liquid phase synthesis may be applicable. Examples of well-known condensation method and a desorption method of protective group, are described in following (1)-(3).
(1) Nobuo Izumiya, et al., The basic and experiment of peptide synthesis, Maruzen Co., Ltd. (1975).
(2) Haruaki Yajima, Shunpei Sakakibara, The biochemistry experiment course 1, Chemistry of protein IV, 205 (1977).
(3) Haruaki Yajima ed., Development of medicine (continued), vol. 14, Peptide Synthesis, Hirokawa Shoten.

Alternatively, a peptide comprising a part of the invention can be synthesized by using several dozens of amino acid residues from C-Terminal, or any several dozens of amino acid residues in the sequence represented by SEQ ID NO: 1, with use of well-known peptide synthesis device. Furthermore, such partial peptide may be produced by selecting a polypeptide having about 50 to 500 amino acids at a suitable site, or a polypeptide having about 500 to whole amino acids at a suitable site, and producing a recombinant protein with use of recombinant technology as above.

For purification after the reaction, suitable combinations of methods well-known in the art, for example, solvent extraction, distillation, column chromatography, liquid chromatography and recrystallization can be used for purification and isolation of the partial peptide of the invention. When a partial peptide obtained in above method is a loose body, it can be converted to a salt by a well-known method. When a partial peptide obtained from above method is a salt, it can be converted to a loose body by a well-known method.

Antibody which specifically binds to the polypeptide of the invention (it exists as a protein), or specifically binds to a peptide comprising a part thereof or a salt thereof, can be a polyclonal antibody or a monoclonal antibody provided that it can specifically recognize the polypeptide, the peptide or the salt. The antibody to the polypeptide (protein) of the invention, its partial peptide or its salt can be produced using the polypeptide (protein) of the invention or its partial peptide as antigen, according to a well-known antibody manufacturing method of antibody or antisera. A peptide which can be used as an immunogen includes a peptide comprising several dozens to one hundred amino acids at C-terminal of the polypeptide of the invention represented by SEQ ID NO: 1, as described in detail in the embodiment of the invention.

For example, in the case of a polyclonal antibody, above antigen itself or a complex of the antigen and a suitable carrier such as cellulose, polymerized amino acid, albumin, and keyhole limpet hemocyanin (KLH) can be used for immunity induction in a suitable animal such as a rat, a rabbit, sheep, a goat or a horse, under presence or absence of an adjuvant. The polyclonal antibody can be collected and purified from the serum of the immune animal according to a variety of well-known methods.

In order to manufacture a monoclonal antibody, antibody forming cells are collected from the immune animal (e.g. from a spleen or a lymph node), and the cells are fused with immortalized proliferation cells (e.g., myeloma cell strains such as mouse myeloma strain P3X63Ag8 or Sp2/OAg-14 derived therefrom, rat myeloma strains Y3-Ag1.2.3, YB2/0, or IR983F) to produce a hybridoma. This hybridoma is cloned then from the resultant clones, those that generate antibodies which specifically recognize the polypeptide of the invention are selected. The monoclonal antibodies can be obtained by collecting and purifying the same from the selected hybridoma culture.

As to manufacturing and purifying methods of an antibody against a synthetic peptide, reference can be made to the following. The Institute of Medical Science, The University of Tokyo ed., New cell technology experiment protocol published by Shunju-sha, 1993, 2-2-2, Manufacturing antibody to synthetic peptide, pp. 210-217.

Various chimeric antibodies such as a humanized antibody containing an antigen determinant of the antibody thus obtained can be produced, according to a variety of well-known genetic engineering methods. The antibody of the invention can be used to detect the polypeptide (protein) of the invention if it exists in samples, such as humor or tissues. Furthermore, the antibody can be used to produce antibody column used to purify the antibody, to detect polypeptide (protein) of the invention in each fraction during purification, and to analyze behavior of the polypeptide (protein) of the invention in sample cells.

The antibody of the invention can be used in an assay of the polypeptide (protein) of the invention in sample solution according to well-known methods. Particularly, it can be used in sandwich immunoassay which uses a monoclonal antibody, and in detection by tissue staining. By these methods, the diseases in which the polypeptide (protein) of the invention plays some role can be diagnosed. For these purposes, the antibody molecule itself, F(ab') 2 fraction, Fab' fraction, or Fab fraction of the antibody molecule can be used. The assay of the protein of the invention using the antibody of the invention is not limited to particular assay. Any assay can be used provided that it can detect the amount of antibody which corresponds to the amount of antigen (e.g., amount of protein), antigen, or antibody-antigen complex in a sample solution by chemical or physical procedures, and calculate the amount based on a standard curve generated based on a standard solution containing known amount of antigen. For example, nephrometry, competition method, immunometry, and sandwich method is preferably used. Among them, the sandwich method is the most preferable in terms of sensitivity and specificity, as described below. As a label agent used for an assay using labeled substance, a radioisotope, an enzyme, a fluorescent substance, a luminescent substance known in the art can be used, for example.

The detail of the general procedures regarding to these assays and detections can be found in several reviews and books. For example, Hiroshi Irie ed. "Radioimmunoassay" (Kodansha Ltd. Publishers, 1979), Eiji Ishikawa et al., ed. "Enzyme immunoassay" (3rd ed.) (Igaku-Shoin, Ltd. 1987), "Methods in ENZYMOLOGY" vol. 70 (Immunochemical Techniques (Part A)), ibid vol. 73 (Immunochemical Techniques (Part B)), ibid vol. 74 (Immunochemical Techniques (Part C)), ibid vol. 84 (Immunochemical Techniques (Part D: Selected Immunoassays)), ibid vol. 92 (Immunochemical Techniques (Part E: Monoclonal Antibodies and General Immunoassay Methods)), ibid vol. 121 (Immunochemical Techniques (Part I: Hybridoma Technology and Monoclonal Antibodies)), published by Academic Press Ltd. For the developmental engineering experiment method including an experiment method for ontogenesis, reference can be made to the followings. Experimental Medicine Separate Volume, Latest technology of gene targeting (p. 34-41, 2000, Yodosha Co., Ltd.), Mouse engineering manual 2nd ed., (p 225-252, p 279-285, 1994) published by Kindai Shuppan, Experimental Medicine Special Number, Developmental Engineering experiment method (total 196 pages, 1994, Yodosha Co., Ltd.).

Antisense nucleic acid having a base sequence substantially complementary to the DNA which encodes the polypeptide (protein) of the invention or a peptide comprising a part thereof includes any antisense nucleic acid provided that it has a base sequence substantially complementary to the base sequence of the DNA, and that it has an effect to suppress the expression of the DNA. A complementary base sequence includes a base sequence that is at least about 95% homologous, most preferably about 100% homologous to the whole or a part of the base sequence complementary to the DNA of the invention. A nucleic acid sequence (DNA, RNA, modified DNA or RNA) having an effect similar to above antisense nucleic acid is also included in the antisense nucleic acid of the invention. A short double strand RNA (RNAi) which is synthesized based on the base sequence information of the DNA can be produced using a known nucleic acid synthesis apparatus.

The polypeptide (protein) of the invention is useful as a reagent for screening a compound or its salt which inhibits the activity of the polypeptide (protein) of the invention. That is, the invention provides a screening method and a screening kit used therein for screening a compound (inhibitor) which inhibits the activity of the polypeptide of the invention or its salt, characterizing that it uses the polypeptide (protein) of the invention, a peptide comprising a part thereof, or a salt thereof. The compound or its salt which is obtained using the screening method or the screening kit of the invention is a compound that is selected from the above test compounds and inhibits the biological activity of the polypeptide (protein) of the invention. The compound or its salt may directly inhibit the activity of the protein of the invention, or may indirectly inhibit it by inhibiting the expression thereof. A salt of the compound includes a pharmaceutically acceptable salt. For example, a salt with inorganic base, a salt with organic base, a salt with inorganic acid, a salt with organic acid, and a salt with basic or acidic amino acid can be used. The compound which inhibits biological activity of the polypeptide (protein) of the invention may also be used as a therapeutic or prophylactic medicine against the various diseases as listed above.

By using the DNA of the invention or a gene containing the DNA derived from a rodent as a probe, any abnormality in DNA or mRNA (aberrant gene) which encodes the polypeptide of the invention or a peptide comprising a part thereof can be detected in a mouse, a rodent, and human. Thus, the DNA or gene is useful as a diagnostic agent for detecting abnormalities in a gene such as impairment, mutation, decreased expression, increase, or increased expression of the DNA and mRNA. The gene diagnosis using the DNA of this invention can be conducted by a well-known method such as Northern hybridization, the PCR-SSCP method (Genomics, vol. 5, p. 874-879 (1989), Proceedings of the National Academy of Sciences of the United States of America, vol. 86, p. 2766-2770 (1989). For a patient who lacks normal function of human KIAA0620 (homolog of the invention) due to an abnormality, deficit, or decreased expression thereof, its function can be recovered by a well-known method. Particularly, (1) the DNA of the invention or a gene derived from human can be introduced and expressed in the patient by gene therapy using a suitable vector such as retrovirus vector, adenovirus vector and adenovirus-associated virus vector as a vehicle, or (2) the polypeptide (protein) of the invention, a polypeptide (protein) derived from human, or an antibody of the invention can be introduced. In the former case, the DNA or a gene derived from human, or its complex with a vehicle of an auxiliary agent which facilitates uptake, can be administered using a gene gun or a catheter such as a hydrogel catheter.

In the specification and drawings, a base or an amino acid is abbreviated according to IUPAC-IUB Commission on Biochemical Nomenclature, or commonly used abbreviation. When an amino acid in the invention has an optical isomer, generally L type amino acid is referred unless otherwise specified.

In the sequence table in the specification, the following SEQ ID NOs represent following sequences.

[SEQ ID NO: 1]

The amino acid sequence of the polypeptide of the invention (1,746 amino acids).

[SEQ ID NO: 2]

The whole base sequence of clone mpf00920 (6,178 bps) containing the base sequence of the DNA which encodes the polypeptide of the invention having the amino acid sequence represented by SEQ ID NO: 1.

[SEQ ID NO: 15]

An amino acid sequence (1,997 amino acids) to which additional 251 amino acids (SEQ ID NO: 11) are added to N-terminal of the polypeptide of the invention represented by SEQ ID NO: 1.

[SEQ ID NO: 16]

The whole base sequence (6,931 bps) containing the base sequence of the DNA which encodes the polypeptide of the invention having the amino acid sequence represented by SEQ ID NO: 15.

[SEQ ID NO: 18]

An amino acid sequence (1,337 amino acids) of the extramembrane region of the polypeptide of the invention derived from a mouse.

[SEQ ID NO: 19]

The whole base sequence (4,011 bps) containing the base sequence of the DNA which encodes the extramembrane region of the polypeptide of the invention having the amino acid sequence represented by SEQ ID NO: 18.

EMBODIMENT

In the following paragraphs, the invention will be described in detail with reference to several embodiments, however, the invention is not limited thereto. The various gene engineering procedures described in the embodiments were carried out according to a method described in Molecular cloning third. ed. (Cold Spring Harbor Lab. Press, 2001).

(1) Construction of cDNA Library Derived from Mouse Embryo Tail Bud

With use of an oligonucleotide: 5'-FgcGCACCACTTTG-TACAAGAAAGCT GGGCGGCCGC $(T)_{18}$-3' (SEQ ID NO: 21 having attB1 site (F, g, c represent fluorescein group, phosphorothioate modified G residue, phosphorothioate modified C residue, respectively) as a primer, and mRNA derived from a mouse embryo tail bud (anterior segment mesoblast and segment mesoblast involved in S1, S0, S–1, and S–2 on the 11.5th day after ICR mouse fertilization) as a template, double strand cDNA was synthesized by Super Script II reverse transcriptase kit (Invitrogen Japan K. K.). An adapter having attB1 site was ligated to the cDNA. The resultant cDNA was fractioned by size through agarose gel to 1 kb-2 kb, 2 kb-3 kb, 3 kb-4 kb, 4 kb-5 kb and 5 kb-7 kb. The fractions were transferred by BP reaction to an attP pSPORT-1 entry vector (Invitrogen) which had been reduced in size, and the resultant substance was introduced to E. coli ElectoroMax DH10B strain (Invitrogen) by electroporation. More than $10^6$ transformants appeared on the plate were collected, and after cultivation in a liquid medium at 37° C. for 2 to 3 hours, plasmid was prepared. The plasmid was fractioned by size in form of super-coiled plasmid, and the cDNA was transferred to attR pBC destination vector (Invitrogen) by LR reaction. After purification, the plasmid was introduced to DH10B strain by electroporation. The fractioning was repeated for 2 to 3 times to obtain desired size for each fraction. Finally, the plasmid was introduced into DH10B strain for every fraction. The cloning system in above experiment using a homologous recombination reaction in a test tube followed the method disclosed by Obara (Nucleic Acids Res., 29, e22 (2001) and DNA Research Vol. 9, 47-57 (2002)).

Next, the DNA sequences of 3'-Terminal of about 16,608 clones contained in all fractions were determined. Among these sequences, whole base sequences were determined for the cDNA of clones which showed high homology to human KIAA0620. For sequencing, DNA sequencer (ABI PRISM3700) and a reaction kit from Applied Biosystems Japan Ltd. was used. A majority of the sequence was determined using the dye terminator method for shotgun clones. For some base sequences, oligonucleotide was synthesized based on the determined base sequence, and sequenced using the primer walking method.

(2) Identification of Clones Containing the DNA of the Invention by Homology Search On the whole base sequences thus obtained, a homology search was conducted using a DNA analysis program (Fasta & Blast). A candidate clone mpf00920 which shows high homology to human KIAA0620 in a public database was identified. Then, the amino acid sequences and base sequences of clone mpf00920 and human KIAA0620 were compared with use of other DNA analysis program (BEST-FIT). At amino acid sequence level, about 91.88% homology was revealed between the 238th to the 1,985th amino acid in the amino acid sequence encoded by human KIAA0620 gene (1,985 amino acids), and the first to the 1,746th amino acid of the amino acid sequence of mpf00920 represented by SEQ ID NO: 1 (1,746 amino acids). In the amino acid sequence of the polypeptide encoded by human KIAA0620 gene, two amino acids, valine and alanine (V, A) were inserted between the 974th and 975th amino acids in the amino acid sequence represented by SEQ ID NO: 1 (1,746 amino acids) of the invention.

By searching public database of amino acid sequence of polypeptide, several data were revealed to show relevant amino acid sequences, however, an amino acid sequence identical to that of the polypeptide of the invention was not found. Particularly, among already published amino acid sequence of polypeptides, two data showed relatively high homology to the amino acid sequence of mpf00920 polypeptide (1,746 amino acids) of the invention, however, substantially identical sequence was not found.

1) Relatively high homology (about 91.70%) was identified between the amino acid sequence from the 178th to the 1,925th amino acid (1,748 amino acids) of Human Plexin-D1 (1,925 amino acids) disclosed in International publication number WO 200114420-A2 (title of the invention: Human Plexin-D1, Applicant: Hyseq INC., Publication date: 11, Oct. 2001), and the amino acid sequence from the first to the 1,746th amino acid (1,746 amino acids) of mpf00920 protein of the invention. Human Plexin-D1 (1,925 amino acids) disclosed in WO 200114420-A2 is derived from human and the specification describes that the amino acid sequence of the polypeptide fraction is used for diagnostic, therapeutic and bio-medical application. However, its detailed function was unknown. In contrast to this homologous amino acid sequence (1,925 amino acids), the 1,746 amino acid sequence of the invention derived from a mouse is a novel sequence and its useful function is elucidated.

2) Relatively high homology (about 91.51%) was identified between the amino acid sequence from the 238th to the 1,992nd amino acid (1,755 amino acids) of Human Plexin-B1/SEP receptor homologue, SEQ ID NO: 2079D1 (1,992 amino acids) disclosed in International publication number WO 200157188-A2 (title of the invention: Human plexin-B1/SEP receptor homologue, SEQ ID NO: 2079, Applicant: Hyseq INC., Publication date: 09, Aug. 2001), and the amino acid sequence from the first to the 1,746th amino acid (1,746 amino acids) of mpf00920 protein of the invention. Human Plexin-B1/SEP receptor homologue, SEQ ID NO: 2079D1 (1,992 amino acids) disclosed in WO 200157188-A2 is derived from human and the specification describes that the amino acid sequence of the polypeptide fraction is used for diagnostic, therapeutic and bio-medical application. However, its detailed function was unknown. In contrast to this homologous amino acid sequence (1,925 amino acids), 1,746 amino acid sequence of the invention derived from a mouse is a novel sequence and its useful function is elucidated.

By searching public database of base sequence, several studies were revealed to report base sequences having homology to mpf00920 base sequence (6,178 bps) of the invention, however, a base sequence identical to that of mpf00920 of the invention was not found. Particularly, among already published base sequence, four data show relatively high homology to the base sequence of mpf00920 (6,178 bps) of the invention, however, substantially identical sequence was not found.

1) Relatively high homology (about 86.95%) was identified between the base sequence from the 710th to the 5,958th base (5,249 bps) of Coding sequence SEQ ID: 118, downregulated in osteogenesis (6,754 bps) disclosed in International publication number WO 200281745-A2 (title of the invention: Coding sequence SEQ ID 118, downregulated in osteogenesis, Applicant: Aventis Pharma SA., Publication date: 17, Oct. 2002), and the base sequence from the first to the 5,243rd base (5,243 bps) of base sequence (6,178 bps) of the invention. Coding sequence SEQ ID 118 is a base sequence derived from human and the expression of which is suppressed during osteogenesis. This sequence shows relatively high homology to mpf00920 base sequence (SEQ ID NO: 2, 6, 178 bps) of the invention, however, is not identical.

1) Relatively high homology (about 86.91%) was identified between a base sequence from the 542nd to the 5,790th base (5,249 bps) of Human cDNA encoding Plexin-D1 (5,892 bps) disclosed in International publication number WO 200114420-A2 (title of the invention: Human cDNA encoding Plexin-D1, Applicant: Univ. Torino, Univ. California, Publication date: 01, Mar. 2001), and the base sequence from the first to the 5,243rd base (5,243 bps) of the sequence of the invention (6,178 bps). The Human Plexin-D1 (6,178 bps) is derived from human and the specification describes that the amino acid sequence of the polypeptide fraction encoded by it is used for diagnostic, therapeutic and bio-medical application. However, its detailed function was not known. In contrast to this base sequence (6,178 bps) having relatively high homology, the 6,178 bps base sequence of the invention derived from a mouse is a novel sequence and its useful function is elucidated.

1) Relatively high homology (about 85.50%) was identified between the base sequence from the 710th to the 5,979th base (5,270 bps) of Human Plexin-B1/SEP receptor homologue-encoding cDNA, SEQ ID NO: 729 (7,080 bps) disclosed in International publication number WO 200157188-A2 (title of the invention: Human plexin-B1/SEP receptor-encoding cDNA, SEQ ID NO: 729, Applicant: HYSEQ INC., Publication date: 09, Aug. 2001), and the base sequence from the first to the 5,243rd base (5,243 bps) of the sequence (6,178 bps) of the invention. Human Plexin-B1/SEP receptor homologue-encoding cDNA SEQ ID NO: 729 (7,080 bps) is derived from human and the specification describes that the amino acid sequence of the polypeptide fraction encoded by it is used for diagnostic, therapeutic and bio-medical application. However, its detailed function was not known. In contrast to this base sequence (7,080 bps) having relatively high homology, 6,178 bps base sequence of the invention derived from a mouse is a novel sequence and its useful function is elucidated.

High homology (about 99.90%) was identified between a base sequence from the 96th to the 1,063rd base (968 bps) of Coding sequences SEQ ID: 43, downregulated in osteogenesis (1,073 bps) disclosed in International publication number WO 200281745-A2 (title of the invention: Coding sequence SEQ ID 43, downregulated in osteogenesis, Applicant: Aventis Pharma SA., Publication date: 17, Oct. 2002), and the base sequence from the 4,909th to the 5,875th base (967 bps) of sequence (6,178 bps) of the invention. Coding sequence SEQ ID 43 is a base sequence derived from human and the expression of which is suppressed during osteogenesis. This sequence shows high homology to mpf00920 base sequence (6,178 bps) of the invention, however, it has rather short base length of 1,073 bps. This sequence has a homology to a part of the base sequence of the invention at 3'-terminal non-coding region of the base sequence of the invention.

The sequences disclosed in the applications 1), 2), and 3) shows relatively high homology to the base sequence of the invention (6,178 bps), as described. However, despite this relatively high homology, the sequence of the invention can be considered to be a completely different novel sequence. The sequence disclosed in the application 4) does not cover whole length of the base sequence of the invention, i.e., gene sequence of mpf00920 (6,178 bps). It only has a high homology to the part of mpf00920 in 3'-terminal side non coding region. Therefore, the gene sequence of the invention can be considered to be a novel sequence completely different from the sequence of 4), despite partially high homology.

From the result of homology search as above, candidate clone mpf00920 shows a relatively high homology to human KIAA0620 gene. Although it is similar to some genes already published, it can be recognized as a novel gene derived from a rodent.

(3) Motif Search

On the DNA of the invention, motif search was conducted (Suyama et. al. 1999 Nucleic Acids Res. 27: 338-339) using a protein analysis program for searching PROSITE database, pftools (BairochA, Bucher P, Hofmann K, Nucleic Acids Res. 1997, Jan. 1; 25 (1): 217-21), and a protein analysis program for searching Pfam database, hmmer 2.1 (Sonnhammer, E. L. L, Eddy, S. R., Birney, E., Bateman, A., and Durbin, R., Nucleic Acids Res 1998; 26, 320-322).

Particularly, according to the HMMSmart search method (Schultz, J. et. al., 1998, Proc Natl Acad Sci USA, 95: 5857-5864), Semaphorin/CD100 antigen domain was identified at the 3rd to the 352nd amino acid from N-terminal in the amino acid sequence represented by SEQ ID NO: 1. According to the HMMPfam search as well as the HMMSmart search, Plexin/Semaphorin/integrin domain was identified at the 371st to the 424th amino acid from N-terminal in the amino acid sequence represented by SEQ ID NO: 1. According to the HMMPfam search, Plexin/Semaphorin/integrin domain was identified at the 524th to the 576th amino acid and the 671st to the 712nd amino acid. Cell surface receptor IPT/TIG domain was identified at the 713rd to the 802nd amino acid from N-Terminal according to the HMMSmart search, and at the 714th to the 802nd amino acids from N-Terminal according to the HMMPfam search. Cell surface receptor IPT/TIG domain was identified at the 803rd to the 889th amino acid from N-terminal according to the HMMSmart search, and at the 804th to the 889th amino acid from N-Terminal according to the HMMPfam search. Cell surface receptor IPT/TIG domain was identified at the 891st to the 970th from N-terminal according to the HMMSmart search, and at the 892nd to the 978th amino acid from N-terminal according to the HMMPfam search. A transmembrane (TM) segment represented by ETAIVVSIVICSVLLLLSVVALF (SEQ ID NO: 22) was identified at the 1,090th to the 1,112nd amino acid from N-terminal, according to a search using a general-purpose transmembrane (TM) segment search program SOSUI.

A Semaphorin/CD100 antigen domain is a characteristic domain highly conserved between species and is located outside of the membrane of Plexin family. It is considered to be involved in specific binding to Semaphorin (documents 9, 16). Plexin/Semaphorin/integrin domain refers to a specific domain comprising characteristic sequence identified in Plexin, Semaphorin, and Integrin. The detail of this repetitive structure which is rich in cystein and located several receptors outside of the cell is not known. But it is known as a novel neurocyte surface molecule which mediates cell adhesion via homophilicity. Plexin exists in the tissue of the brain and epithelium and is involved in collapse or loss of brain growth cane which is induced by Semaphorin, while Integrin is involved in completion of migration of the epithelium cells (documents 9, 16). IPT/TIG domain has an immunoglobulin-like folded structure, and found in cell surface receptors such as Met and Ron, as well as intracellular transcription factors involved in DNA binding. Ron tyrosine kinase receptor shares characteristic functions with the subfamily members such as Met and Sea. These functions include a control of cellular phenomena such as separation or dissociation of cells, movement of cells, and invasion of extracellular skeleton into cells (documents 9, 16).

Based on these findings, the amino acid sequence of the polypeptide encoded by mpf00920 gene of the invention can be identified as follows and its function can be estimated. Particularly, the polypeptide has 1,746 amino acid length which is 237 amino acids shorter than human KIAA0620; Semaphorin/CD100 antigen domain, three Plexin/Semaphorin/integrin domains, and three Cell surface receptor IPT/TIGs; a transmembrane (TM) segment at C-terminal side; and a structure 239 amino acids shorter than human KIAA0620 protein (1,985 amino acids) (FIG. 1).

(4-1)

Search of Expression Site of mpf00920 Gene in Development Process Using Mouse Fetus Some reports indicate that human KIAA0620 gene belongs to Plexin family (Tamagnone, L., et. al., 2001, Cell, 99: 71-80), and that mRNA which hybridizes with human KIAA0620 gene is expressed in vascular endothelial cells or CNS, a phenomenon found by mRNA search in the mouse development process using human KIAA0620 gene as a probe (van der Zwaag, B. et al., Dev. Dyn., 2002, 225: 336-343). However, the expression site of novel Plexin gene of the invention in the mouse development process was unknown. Following experiment was conducted in order to detect expression site of mouse mpf00920 gene, one of the genes of the invention, in the mouse development process.

A forward primer and a reverse primer necessary for probe production by amplifying mpf00920 genes by PCR were synthesized using a commercially available DNA automatic synthesizer. The experiment design was as follows. The forward primer was defined as 5'-CCCCGGAACTTGAACGT-GTC-3' (SEQ ID NO: 3) and a reverse primer was defined as 5'-CCACCTGTTCAAACTTGTGCTG-3' (SEQ ID NO: 4). Using these primers, the transcript products of mouse mpf00920 gene was amplified by PCRto obtain about 1,069 bps DNA fragments which served as an antisense probe or a sense probe. The target PCR products, i.e., about 1,069 bps DNA fragments for an antisense probe or sense probe were cloned to T-vector supplied by Promega Co., Ltd. Using 1,069 bps DNA fragment cloned to T-vector as a template, and T7 or SP6RNA polymerase, an antisense cRNA probe which can detect mouse mpf00920 gene expression products, and a sense cRNA probe used as a negative probe were produced according to a method indicated by Promega. These probes were used in following experiments to analyze tissue specific expression of the gene in each stage in ontogenesis.

Mouse fetuses which reflected various ontogenesis stages (d.p.c.: the development stage is represented by the number of days after fertilization) based on the number of days elapsed from fertilization, was fixed according to the in situ hybridization fixing method usually used in whole mount in situ hybridization. For this sample, tissue specific expression was analyzed according to the whole mount method, using the whole mount in situ hybridization method indicated in DIG label method supplied from SuperBioChips Lab. Co., Ltd (refer to Cell Engineering separate edition, Experiment protocol without isotope, 192-223, 1998).

New findings as follows were obtained from expression site analysis of the gene using a mouse fetus. Mouse mpf00920 gene is specifically expressed in vascular endotherlial cells only during vasculogenesis in ontogenesis. Particularly, mpf00920 positive signal was observed in vascular site in the period (7.5 to 8.0 d.p.c.) when precursor vascular cells (Flk1 positive cells) appeared during ontogenesis. The gene showed an expression pattern specific to vessels through vasculogenesis. From detailed analysis under microscope of mpf00920 expression site during ontogenesis, the expression of mpf00920 gene was not found specifically in vascular endothelial cells, but the gene showed an expression pattern specific to vascular endothelial cells at early stage of vasculogenesis in mouse fetus development processes (10.5, 8.0; and 9.5d.p.c) (FIGS. 2A, 2B, 2C, 2D). On the contrary, the vascular endothelial cell specific expression of the gene was not observed during period from late ontogenesis to adult.

Figure 2A:
FIG. 2A illustrates expression sites of mpf00920 (mouse KIAA0620) gene in various development stages of a mouse 10.5d. p. c., detected by the whole mount in situ method. Illustrated is an image detected by a negative control using a sense probe (expression sites are represented by deep stained region along the vessel).
Figure 2B:
FIG. 2B illustrates expression sites of mpf00920 (mouse KIAA0620) gene in various development stages of a mouse 10.5d. p. c., detected by the whole mount in situ method. Illustrated is the expression intensity of mpf00920 gene detected by using an antisense probe (expression sites are represented by deep stained region along the vessel).
Figure 2C:
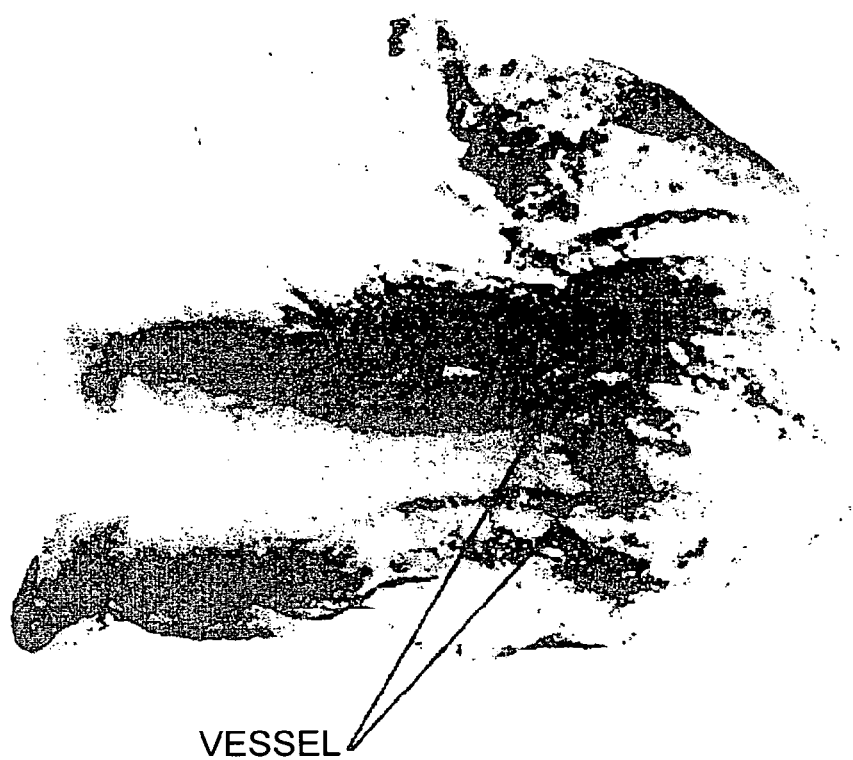
FIG. 2C illustrates expression sites of mpf00920 (mouse KIAA0620) gene in various development stages of a mouse 8 d. p. c., detected by the whole mount in situ method (expression sites are represented by deep stained region along the vessel).
Figure 2D:
FIG. 2D illustrates expression sites of mpf00920 (mouse KIAA0620) gene in various development stages of a mouse 9.5d. p. c., detected by the whole mount in situ method (deep stained region can be identified along the vessel).

The top view in FIG. 2A shows non-specific gene expression detected by using a sense cRNA fragment as a negative control, while the bottom view in FIG. 2A shows mpf00920 gene expression detected by using an antisense cRNA fragment. From these results, it is indicated that mpf00920 gene expression is detected with use of an ant sense cRNA fragment, while it is not detected with use of a sense cRNA fragment, and that the possibility that DNA fragment of about 1,069 bps used in the experiment catches signals of non-specific gene expression is low.

(4-2)

Expression Frequency Search of mpf00920 Gene at mRNA Level in Fetus 14.5 Days after Fertilization and Adult According to in Situ Hybridization There is no finding on the expression frequency of human KIAA0620 gene at mRNA level in human (http://www.kazusa.or.jp/huge/gfpage/KIAA0620/, DNA Res., 1998, 5: 169-176 earch 1997, 4: 345-349). The expression frequency of mouse mpf00920 gene, which is homologous to human KIAA0620 gene, in a mouse at mRNA level was examined by analyzing tissue specific expression using an adult mouse according to the in situ hybridization method. The forward primer and reverse primer, which were necessary to produce probe by amplifying mouse mpf00290 gene according to PCR method, were synthesized using a commercially available DNA automatic synthesizer. The experiment design was as follows. The forward primer was defined as 5'-CCCCG-GAACTTGAACGTGTC-3' (SEQ ID NO: 3) and a reverse primer was defined as 5'-CCACCTGTTCAAACTTGT-GCTG-3' (SEQ ID NO: 4). Using these primers, the transcript products of mouse mpf00920 gene were amplified by PCR to obtain about 1,069 bps DNA fragments which served as an antisense probe or a sense probe. The target PCR products, i.e., about 1,069 bps DNA fragments for an antisense probe or sense probe were cloned to T-vector supplied by Promega. Using 1,069 bps DNA fragment cloned to T-vector as a template, and T7 or SP6RNA polymerase, an antisense CRNA probe which can detect mouse mpf00920 gene expression products, and a sense cRNA probe used for negative control were produced according to a method indicated by Promega. These probes were used in following experiments to analyze tissue specific expression of the gene.

Frozen sagittal section of a mouse fetus 14.5 days after fertilization was used as a sample, and fixed in a process including 15 minutes, 37° C. Proteinase Kprocess. Then according to the in situ hybridization method indicated in DIG label method supplied by SuperBioChips Lab Co., Ltd., 500 ng DIG label RNA was used as a probe for one tissue section on one slide glass. After 16 hours hybridization at 50° C., tissue-specific expression was analyzed (refer to Cell Engineering separate edition, Experiment protocol without isotope, 192-223, 1998).

Figure 3B:
FIG. 3B is a highly enlarged image showing expression intensity of mpf00920 gene in the brain detected by using an antisense probe (expression sites are represented by deep stained region).

As shown in Table 1, the intensity analysis of mouse mpf00920 gene expression signal in various tissue sections showed following results: intense expression was observed in the brain and the cerebral cortex, and the submandibular gland; moderately intense expression was observed in the trigeminal nerve ganglion, the bone and rib, the latissimus dorsi, and the stomach and intestines; and expression was observed in several organs such as the skin and dermis, the brain and cerebellum, the bone the backbone, the vessels in the heart and atrium cordis, the myocardium of the heart and ventricle, and the vessels in the heart and ventricle. As for the epidermis of skin, the vessels in lungs, the lung and alveolar cells and myocardium of the heart and an atrium, the signal was too weak to be detected. Refer to FIGS. 3A and 3B.

As a result, intense expression of the polypeptide encoded by the gene of the invention was observed in the brain and cerebral cortex, and the submandibular gland; moderately intense expression was observed in the trigeminal nerve ganglion, the bone and rib, the latissimus dorsi, the stomach and intestines; and expression was observed in several organs including the brain and nerve, the submandibular gland, the skin, the bone, the muscle and the heart, in a mouse fetus 14.5 days after fertilization. This expression may be associated with development and differentiation of organs and tissues, and preservation of functions.

Table 1) Result of in situ hybridization using frozen sagittal section of mouse fetus 14.5 days after fertilization (+++: intense expression; ++: moderately intense expression; +expression; – too week signals to be detected)

TABLE 1

| Organ, major division | Organ, Minor division | Hybridization intensity |
| --- | --- | --- |
| Skin | Epidermis | – |
|  | Dermis | + |
| Brain | Cerebral cortex | +++ |
|  | Cerebellum | + |
| Trigeminal ganglion |  | ++ |
| Submandibular gland |  | +++ |
| Bone | Spine | + |
|  | Costea | ++ |
| Lung | Blood vessel | – |
|  | Alveolar cells | – |
| Heart | Atrium-myocardium | – |
|  | Atrium-blood vessel | + |
|  | Ventricle-myocardium | + |
|  | Ventricle-blood vessel | + |
| Latissimus dorsi muscle |  | ++ |
| Stomach |  | ++ |
| Intestine |  | ++ |

A paraffin tissue section was prepared for each tissue of an adult mouse. The section used as a sample was placed on Tissue Array Slide (manufactured by SuperBioChips Lab Co., Ltd. and supplied by Funakoshi Co., Ltd. Lot: ZE1). The sample was fixed in a process including 15 minutes, 37° C. Proteinase K process. Then according to the in situ hybridization method indicated in DIG label method supplied by SuperBioChips Lab Co., Ltd., 500 ng DIG label RNA was used as a probe for one tissue section on one slide glass. After 16 hours hybridization at 50° C., tissue-specific expression was analyzed (refer to Cell Engineering separate edition, Experiment protocol without isotope, 192-223, 1998).

Figure 4A:
FIG. 4A illustrates expression sites of mpf00920 (mouse KIAA0620) gene represented by mRNA level in a paraffin section of a stomach of an adult mouse detected by the in situ method. The stratified-squamous-epithelia site is deeply stained.

As shown in Table 2, in the intensity analysis of mouse mpf00920 gene expression signal in tissue slices excised from different organs of an adult mouse, intense expression was observed in the stratified squamous epithelium in the stomach; moderate expression was observed in the epithelial cells of the uterus, and the Purkinje cell layer in the brain; expression was observed in various organs including the skin, the spleen, the heart, the tongue, the kidney, the testicle, and the glia cells in the brain. As for the dermis of skin, the red pulp of spleen, the skeletal muscle, the lungs, the vessels in lungs, the cardiac blood vessels, the salivary glands, the liver, the pancreas, the small intestine, the colon, the ovary, and the thymus, signal was too weak to be detected. Refer to FIGS. 4A, 4B, and 4C.

In the above result, the polypeptide encoded by the gene of the invention can be observed in various organs of an adult including the stomach, the uterus and the brain. The polypeptide is involved in development and differentiation of the organs and tissues, and preservation of their functions. In particular, the polypeptide of the invention is presumed to be involved in elongation and maintenance of network of neurocytes in the brain and nervous system, and maintenance of structure in the heart, the vessels, and other organs having lumen structure. The polypeptide of the invention may have molecular functions different between development stages, namely, angiogenesis at early stage of development, and guidance of neurocytes in a various tissues including the brains in an adult. For example, a study reported that Plexin in cooperation with Neuropilin binds to a Semaphorin dimer to form a complex. This complex is associated with the adjustment to inhibit elongation of neurocytes (document 16).

Table 2) Result of in situ hybridization using adult mouse paraffin tissue section (+++: intense expression; ++: moderately intense expression; +expression; – too week signals to be detected)

TABLE 2

| Organ, major division | Organ, Minor division | Hybridization intensity |
|---|---|---|
| Skin | Epidermis | + |
| Ear lobe | Dermis | – |
| Spleen | White pulp | + |
|  | Red pulp | – |
| Skeletal muscle, Abdominal wall |  | – |
| Lung | Blood vessel | – |
|  | Aalveolar cells | – |
| Heart | Myocardium | + |
|  | Blood vessel | – |
| Tongue | Muscle layer | + |
|  | Filiform papilae | + |
|  | Stratified squamous epithelium | + |
| Salivary gland |  | + |
| Liver |  | – |
| Pancreas |  | – |
| Stomach | Stratified squamous epithelium | +++ |
|  | Fundic gland | + |
| Small intestine |  | – |
| Colon |  | – |
| Kidney, cortex | Proximal tubule | + |
|  | Tubule | + |
| Kidney, meudulla | Tubule | + |
| Urinary bladder |  | + |
| Seminal vesicle |  | + |
| Tstis | Sertoi's celles | + |
|  | Spematocytes | + |
| Eepididymis |  | – |
| Uuterus | Glandular epithelium | ++ |
| Ovary |  | – |
| Thymus |  | – |
| Cerebrum | neuroglia cells | + |
| Pons |  | + |
| Cerebellum | Guranular layer | + |
|  | Purkije cell layer | ++ |

(4-3)

Frequency of mKIAA0620 Expression at mRNA Level in Development Process of Mouse Fetus Expression of mKIAA0620 specific to development stage at mRNA level was analyzed in mouse fetus development process according to RT-PCR. The experiment design was as follows. The forward primer was defined as 5'-CCCCG-GAACTTGAACGTGTC-3' (SEQ ID NO: 3) and the reverse primer was defined as 5'-CCACCTGTTCAAACTTGT-GCTG-3' (SEQ ID NO: 4). Using these primers, the transcript products of mouse mpf00920 gene were amplified by PCR to obtain about 1,069 bps DNA fragments which served as an antisense probe or a sense probe. The target PCR products, i.e., about 1,069 bps DNA fragments for an antisense probe or sense probe were cloned to T-vector supplied from Promega. Using 1,069 bps DNA fragment cloned to T-vector as a template, and T7 or SP6RNA polymerase, an antisense cRNA probe which can detect mouse mpf00920 gene expression products, and a sense cRNA probe used for negative control were produced according to the method indicated by Promega. These probes were used in following experiments to analyze tissue specific expression of the gene at different stages in development of a mouse fetus. That is, the 1st strand cDNA at different stages in development of a mouse fetus and above primers were mixed respectively. PCR was conducted for each mixture to amplify about 1,069 bps DNA fragment in the transcription products of mouse KIAA0620 gene. PCR were conducted as follows. TaKaRa Ex Taq (Takara Shuzo Co., Ltd., #RP001A) was used as Taq polymerase. After heating above DNA mixture for 2.5 minutes at 95° C., a cycle consisting 95° C. (30 seconds)/60° C. (30 seconds)/72° C. (30 seconds) was repeated 35 times. As a control, about 1,129 bps DNA fragment derived from FLk1 transcript product generated by using a primer to detect Flk1 gene expression was also amplified in a similar manner. PCR products thus amplified, together with a size marker, was fractioned by electrophoresis using 2% agarose gel (Rockland Co., Ltd., #50070). The amount of the fractioned PCR products was compared semi-quantitatively (FIG. 5). As a result, expression of Flk1 was observed from 7.5 d.p.c., which is a stage wherein angiogenesis begins in the development process of a mouse fetus. Intense expression continued through the angiogenesis until 9.5 d.p.c. The expression of mouse KIAA0620 gene was observed from 6.5 d.p.c., which is a stage a little earlier than the angiogenesis. Intense expression continued through the angiogenesis until 9.5d.p.c. Based on this finding, it can be presumed that the expression of KIAA0620 occurs earlier than Flk1 and it may induce angiogenesis. Conventionally, FIK1 has been considered to be a marker gene of angiogenesis.

(5-1) Elongation of DNA Sequence at 5'-Terminal

As 5'-terminal of mouse mKIAA0620 (gene name: mpf00920) is shorter than human KIAA0620, it was presumed that some sequence may be added to mKIAA0620 base sequence. However, it was very difficult to obtain putative 5'-terminal sequence based on the comparison with human KIAA0620 gene as above (2), from a mouse cDNA library. Thus, in order to high throughput search of long text sequence such as long-chain cDNA of mammalian genome sequence, a computer (hardware) was developed and its control algorithm design was studied wherein computation time is independent from the length of a sequence. The computer employs content addressable memory (CAM) which has a comparator added to a memory disclosed in Japanese published unexamined application 2003-216615. This improved novel system, named super parallel genome comparator, was configured to design analysis method of long-chain cDNA. With use of the completed super parallel genome comparator, large-scale high throughput base sequence search of mouse mKIAA0620 was carried out in the public mouse genome database. In the public database, information on the sequence which may be added to mKIAA0620 base sequence (SEQ ID NO: 17) was searched. As a result, a primer was designed which is necessary to obtain 251 amino acid sequence added to N-terminal of the amino acid sequence represented by SEQ ID NO: 1 of the invention.

(5-2) Elongation of 5'-Terminal DNA Sequence

A reverse primer (SEQ ID NO: 5, AATCTTGATGTGG-TACTCATGGCTCTC, 27 bps, name GSP1. A sequence complementary to the 3,090th to the 3,166th base (27 bps) in the sequence represented by SEQ ID NO: 2) was designed based on the partial sequence information of mpf00920 gene sequence represented by SEQ ID NO: 2. With use of this reverse primer, and Total RNA isolated and purified from a mouse fetus (10.5 fetal days) as a material, in vitro reverse transcription reaction (50° C. 60 mins) was conducted to synthesize 1st strand cDNA (containing unidentified sequence) by ThermoScript RNaseH-RT (Invitrogen). Next, a forward primer (SEQ ID NO: 6, AAGCT-GCTGGGGCGGGGAGATGGGCT, 26 bps. A sequence from the 72nd to the 97th base in the sequence represented by SEQ ID NO: 17) was designed based on the putative sequence information anticipated by the comparator (anticipated from the genome sequence), and a reverse primer (SEQ ID NO: 7, AATGTTGTGTCCTTTGACCCTTAC, 24 bps, name GSP2. A sequence complementary to the sequence from the 1,524th to the 1,547th base of the sequence represented by SEQ ID NO: 2) which was located little inner from GSP1 was designed based on the partial sequence information of mpf00920 gene sequence represented by SEQ ID NO: 2. With use of these primers, a putative sequence fragment was amplified according to the PCR. However, amplification by PCR failed under general reaction condition, and PCR product could not be obtained. Therefore, it was anticipated that a special sequence (a sequence rich in GC) which inhibited the reaction existed in the region to be amplified.

In order to amplify a special DNA fragment rich in GC, the Forward primer and the Reverse primer (GSP2) was used to conduct another elongation reaction. This time, Platinum Pfx DNA Polymerase (Invitrogen: Cat No. 11708-013) and PCRx Enhancer solution attached thereto was used, and reaction condition (1×PCRxEnhancer solution. Condition: Denature: 94° C. for 15 s. Anneal: 50° C. for 30 s. Extend: 68° C. for 3 min30 s, 40 cycles) was reset anew. As a result, a DNA fragment of about 2,314 bps including the target fragment of about 2,300 bps could be amplified by a PCR reaction.

With use of the DNA fragment thus obtained as a primary template and Platinum Pfx DNA Polymerase as the above, Nested PCR was conducted. Particularly, a forward primer (SEQ ID NO: 8, TTGTCGACACAAGTTTGTA-CAAAAAAGCAGGCTCT atg ggc tgt ggg cgt ggt ctc cac gga gcc gcc ccc ggg ctg agc, 80 bps. A sequence from the 91st to the 135th base in the sequence represented by SEQ ID NO: 17) was designed, and based on the partial sequence information of mpf00920 gene sequence represented by SEQ ID NO: 2, a reverse primer (SEQNO: 9, AAATGTGGCTGGCTG-GAGTTGGT, 23 bps. A sequence complementary to the sequence from the 1,215th to 1,237th base (23 bps) in the sequence represented by SEQ ID NO: 2) was designed a little inner than GSP2. In order to amplify a special DNA fragment rich in GC, Nested PCR was conducted with reference to the PCR conditions as above. The detailed condition of PCR reaction condition was as follows: final: 1×PCRxEnhancer solution. Denature: 94° C. for 15 s. Anneal: 50° C. for 30 s. Extend: 68° C. for 3 min. 35 cycles). As a result, the target DNA fragment of about 2,020 bps could be amplified by a PCR reaction.

The resultant PCR product was inserted into pCR4 Blunt TOPO vector (Invitrogen: Cat. No. K4575-J10) to transform E. coli (DH5α strain), and a plasmid DNA containing the target PCR product was prepared. From the transformant, the plasmid DNA was amplified. With use of the amplified plasmid DNA, the novel base sequence of the target PCR product was determined by a sequencer. As a result, a base sequence of 753 bps (SEQ ID NO: 10), and an amino acid sequence encoded thereby (SEQ ID NO: 11) could be obtained as novel sequences. Based on the analysis of SEQ ID NO: 10, Met at the second position in the sequence encoded by SEQ ID NO: 11 was estimated to be N'-terminal. This position is longer by 71 amino acids than the position of Met at N'-terminal in an amino acid sequence anticipated based on the amino acid sequence of the polypeptide encoded by human KIAA0620 gene, or the position of Met at N'-terminal in amino acid sequence of human PLEXIN-D1 reported by van der Zwaag (Dev. Dyn., 2002, 225: 336-343, non-patent document 8). Therefore, we used the DNA fragment containing second Met in the sequence represented by SEQ ID NO: 11, in the expression experiment of the invention. A sequence corresponding to a signal sequence (cleavable signal sequence) of the 30th to 46th amino acid from N'-terminal in the amino acid sequence of PLEXIN-D1 reported by van der Zwaag can be observed in the 102nd to 120th amino acids in the sequence represented by SEQ ID NO: 11. Therefore, in terms of function, the protein synthesis may begin from the 73rd Met in the mouse sequence represented by SEQ ID NO: 11. That is, both of the 2nd and 73rd Met in SEQ ID NO: 11 may be a putative origin of protein synthesis.

(5-3)

Homology Search

Homology search was conducted by FASTA on the sequence of 251 amino acids and the base sequence of 753 bps added to 5'-terminal of mpf00920 base sequence. Two sequences showed relatively high homology, however, substantially identical sequence could not be found.

Particularly, relatively high homology (about 86.03%) was identified between the first to the 117th amino acid (177 amino acids) of Human Plexin-D1 (1,925 amino acids) disclosed in International publication number WO 200114420-A1 (title of the invention: Human Plexin-D1, Applicant: Hyseq INC., Publication date: 11, Oct. 2001), and the 73rd to the 251st amino acid (179 amino acids) in the sequence of 251 amino acids (an amino acid sequence from the first to the 251st amino acid in the sequence represented by SEQ ID NO: 15) which was added to 5'-terminal of mpf00920 amino acid sequence of the invention.

Relatively high homology (about 80.75%) was identified between the first to the 237th amino acid (237 amino acids) of Human Plexin-B1/SEP receptor homologue, SEQ ID NO: 2079D1 (1,992 amino acids) disclosed in International publication number WO200157188-A2 (title of the invention: Human plexin-B1/SEP receptor homologue, SEQ ID NO: 2079, Applicant: Hyseq INC., Publication date: 09, Aug. 2001), and the 13th to the 251st amino acid (237 amino acids) in the amino acid sequence (251 amino acids; the first to the 251st amino acid in the sequence represented by SEQ ID NO: 15) added to 5'-terminal of mpf00920 amino acid sequence of the invention.

As will be described below, two applications claim partial sequences which show homology to 753 bps sequence (the 1st to 753rd base in the sequence represented by SEQ ID NO: 16) added to 5'-terminal of mpf00920 base sequence. However, no application discloses a sequence substantially identical to 753 bps added in the invention.

Relatively high homology (about 89.28% and 95.15%) was identified between the 284th to the 709th base (426 bps), and the 25th to 230th base (206 bps) in Coding sequence SEQ ID 188, downregulated in osteogenesis (6,754 bps) disclosed in International publication number WO 200281745-A2 (title of the invention: Coding sequence SEQ ID 118, downregulated in osteogenesis, Applicant: Aventis Pharma SA., Publication date: 17, Oct. 2002), and the 328th to the 753rd base (426 bps), and the 64th to the 268th base (205 bps) in the 753 bps sequence (the 1st to the 753rd base sequence in the base sequence represented by SEQ ID NO: 16) which was added to 5'-terminal of the invention.

Relatively high homology (about 89.28% or 95.15%) was identified between the 284th to the 709th base (426 bps) and the 25th to the 230th base (206 bps) in Human Plexin-B1/SEP receptor homologue-encoding cDNA, SEQ ID NO: 729 (7,080 bps) disclosed in International publication number WO200157188-A2 (title of the invention: Human plexin-B1/SEP receptor-encoding cDNA, SEQ ID NO: 729, Applicant: HYSEQ INC., Publication date: 09, August), and the 328th to the 753rd base (426 bps) and the 64th to the 268th base (205 bps) in the base sequence (the first to the 753rd base in the base sequence represented by SEQ ID NO: 16) (753 bps) added to 5'-terminal of the invention.

Based on the findings obtained from homology search as above, it was determined that a base sequence (a base sequence represented by SEQ ID NO: 16) having additional 753 bps sequence added to 5'-terminal of mpf00920 gene (a base sequence represented by SEQ ID NO: 2) is a novel gene which is derived from a rodent and shows relatively high homology to human KIAA0620 gene, in spite of similarity to some *known* genes already reported.

(6) Producing Transgenic Cells

With use of mpf00921 gene sequence represented by SEQ ID NO: 2 (non full-length cDNA lacking 5'-terminal sequence: 6,178 bps), and PCR product comprising 5'-terminal DNA fragment (SEQ ID NO: 10) obtained in above (5), a full-length cDNA (SEQ ID NO: 16) corresponding to ORF was obtained according to the following procedure. First, mpf00921 gene sequence represented by SEQ ID NO: 2 (non full-length cDNA of mouse KIAA620) was inserted into a multi-cloning site of pBluescript SK (+) to prepare a recombinant plasmid. Particularly, with use of Bam HI site in the sequence of multi-cloning site of pBluescript SK (+), 5'-terminal DNA fragment which had been cut by same restricted enzyme was designed and ligated for alignment to the frame. Then, *E. coli* (DH 5α strain) was transformed to generate a plasmid DNA containing full-length DNA fragment of interest. The plasmid containing full-length ORF cDNA (5,992 bps. A sequence that encodes a polypeptide of 1,996 amino acid, plus stop codon) was transformed into *E. coli*, and purified and collected. A plurality of expression construct was prepared using this plasmid as a template. For preparing the expression construct, GATEWAY™ cloning technology (IN-VITROGEN:™ Cat. No. 11821-014) system was used, and an entry clone comprising following target PCR product incorporated into pENTR/D-TOPO Vector INVITROGEN™. PCR product to be used for native protein was prepared by designing and synthesizing following primer as full-length cDNA (from initiation codon to stop codon), and conducting PCR reaction. Particularly, with use of CAC-Catgggctgtgggcgtggtct (SEQ ID NO: 12, 24 bps. The sixth to 25th base (20 bps) in the sequence represented by SEQ ID NO: 16) as a forward primer, and Reverse primer 1 (SEQ ID NO: 13, TCAGGCCTCGCTGTAACACTCATAGA, 26 bps.

A sequence complementary to 26 bps sequence from the 5,218th to the 5,243rd base in the sequence represented by SEQ ID NO: 2, including a stop codon) as a reverse primer, entry clone was prepared. Tagged PCR product to be used for tagged fusion protein was prepared by designing, synthesizing and using the following primer as atagged full-length cDNA (from initiation codon to stop codon), by PCR reaction. Particularly, with use of above Forward primer (SEQ ID NO: 12, CACCatgggctgtgggcgtggtct, 24 bps. The 6th to 25th base (20 bps) in the sequence represented by SEQ ID NO: 16) as a forward primer, and Reverse primer 2 (SEQ ID NO: 14, GGCCTCGCTGTAACACTCATAGA, 23 bps. A sequence complementary to 23 bps sequence from the 5,218th to the 5,240th base in the sequence represented by SEQ ID NO: 2, not including a stop codon) as a reverse primer, entry clone was prepared.

Each entry clone was transformed to an expression destination vector (pcDNA-DEST40 vector, pcDNA-DEST47 vector. Both of them are plasmid vectors expressed under the control of CAG promoter), by site-specific recombination reaction using LR Clonase enzyme mix (Invitrogen: Cat. No. 11791-019), and an expression vector was constructed. And a compulsive expression vector in mammalian cells was constructed which encodes a fusion protein of mouse KIAA0620 native protein, mouse KIAA0620-GFP-HisTag fusion protein, and mouse KIAA0620—V5 fusion protein. The vector was introduced into kidney cells derived from human fetus (HEK293T cell), using Transfection reagent (Fugene6; Roche Diagnostics K. K., or, Trans IT-LT1 reagent; Mirus Co., Ltd.), and transgenic cells were prepared.

(7-1)

Producing Rabbit Polyclonal Antibody Using Synthetic Peptide as Antigen

As an immunogen (antigen), synthetic peptide prepared based on the amino acid sequence comprising a part of polypeptide encoded by mouse KIAA0620 gene was used to prepare rabbit polyclonal antibody according to conventional method. An antigen was prepared as follows. Cystein was added to the end of 15 amino acid sequence which is about 169 amino acids away from C-terminal of mpf00920 polypeptide sequence (sequence: FLEEQAEKRGISDPD) (SEQ ID NO:23) to prepare synthetic peptide (sequence: CFLEEQAEKRGISDPD)(SEQ ID NO: 24). The synthetic peptide was carrier-coupled at its N-terminal to keyhole limpet hemocyanin (KLH) as carrier. The resultant peptide was purified to 80% to 90% purity to obtain antigen. Intracutaneous immunization was conducted on *Oryctolagus cuniculus* var. *domesticus* GM (female). Immunization was conducted five times: at first time, antigen amount 0.15 mg, at second to fifth times, antigen amount 0.3 mg was respectively administered about every second weeks. About five weeks after the third intracutaneous immunization and after seven weeks after the fourth immunization, 5 ml blood sample was collected, to determine antibody level relative to the antigen according to the ELISA method using HRPO (horseradish peroxidase) binding goat anti-rabbit IgG antibody (CAPPEL Co.). In two test samples, absorbance (490 nm) 3 was obtained for 1000-fold dilution, 2000-fold dilution, 4000-fold dilution, 8000-fold dilution, and 16000-fold dilution, demonstrating sufficient rise in antibody level in sample blood. About 8 weeks after the second blood collection, 5th sensitization was conducted. About 9 weeks after the sensitization, whole blood was collected for purification of antibody. Antiserum was obtained by isolating the serum from collected blood by centrifugation. The antiserum was used as rabbit polyclonal antibody (anti-mKIAA0620 ab).

As control serum, sample blood was collected (3 ml) before immunization. For this control sample without immunization, absorbance (490 nm) 0.171, 0.101, 0.089, 0.084, and 0.076 were obtained for 1000-fold dilution, 2000-fold dilution, 4000-fold dilution, 8000-fold dilution, and 16000-fold dilution. Thus, it was confirmed that the amino acid sequence used as an antigen had specificity in that it did not react with rabbit serum without immunization.

(7-2)

Detection of Mouse KIAA0620 Protein According to Western Blotting in Various Transgenic Cells Using Purified Rabbit Polyclonal Antibody With use of the purified rabbit polyclonal antibody obtained as above, mouse KIAA0620 protein was detected in various transgenic cells according to the Western blotting. The protein was collected from the transgenic cells according to the following procedures. In order to collect protein from the transgenic cells, HEK293T cells to which mouse KIAA0620 gene compulsive expression vector was introduced were washed on a culture dish with PBS (−) solution, and solubilized by repeated pipetting with Lysis Buffer (TNE buffer). The solubilized solution was introduced into 28G injection needle. After centrifugation (700 g, 10 min), supernatant was collected as a sample solution which contained protein from mouse KIAA0620 gene transgenic cells. Other sample solution was prepared in similar manner using HEK293T cells into which expression vector which expresses mouse KIAA0620—V5 fusion protein was introduced. Sample solutions were fragmented by polyacrylamide gel electrophoresis. Polyacrylamide gel electrophoresis was conducted as follows. About 20 micrograms of different proteins derived from different transgenic cells were applied to each lane, and polyacrylamide gel electrophoresis was performed to fraction the sample. Then fractioned proteins were plotted on membrane. On the plotted membrane, immunostaining reaction was performed using 500-fold or 1000-fold diluted antibody. Polyacrylamide gel electrophoresis was conducted using 4-12% Tris-Glycine Gel (#NO. EC6035Box) supplied from INVITROGEN™. Protein was transferred using the semi-dry transfer cell supplied from Bio Rad Co., Ltd, and plotted on the membrane. As second antibody, 5000-fold diluted Goat Anti-Rabbit IgG, HRP-conjugate antibody BIOSOURCE™ (#No. ALI0404) was used, and for detection, ECL Western blotting Detection Reagents BIOSOURCE™ (#No. RPN2133) was used. In order to determine molecular weight, a pre-stained protein marker supplied from Nacalai Tesque (High Range, SDS-PAGE (#No. 26039-75) was electrophoresed together with each sample.

On a membrane having HEK293T recombinant cells or other recombinant cells as a starting material, an experiment to detect protein using anti-V5-HRP antibody (5000-fold diluted solution was used) according to the Western blotting was conducted. Into the recombinant cells, the expression vector which expresses fusion protein of mouse KIAA0620 protein and V5 protein was introduced. As a result, a distinct single band could be detected at the position corresponding to the size of mouse KIAA0620—V5 fusion protein (about 220 kDa) by anti-V5-HRP antibody. The molecular weight represented by the detected band corresponded to theoretical molecular weight of mouse KIAA0620—V5 fusion protein, indicating that mouse full-length KIAA0620 protein was expressed as a protein fused with V5.

Figure 6:
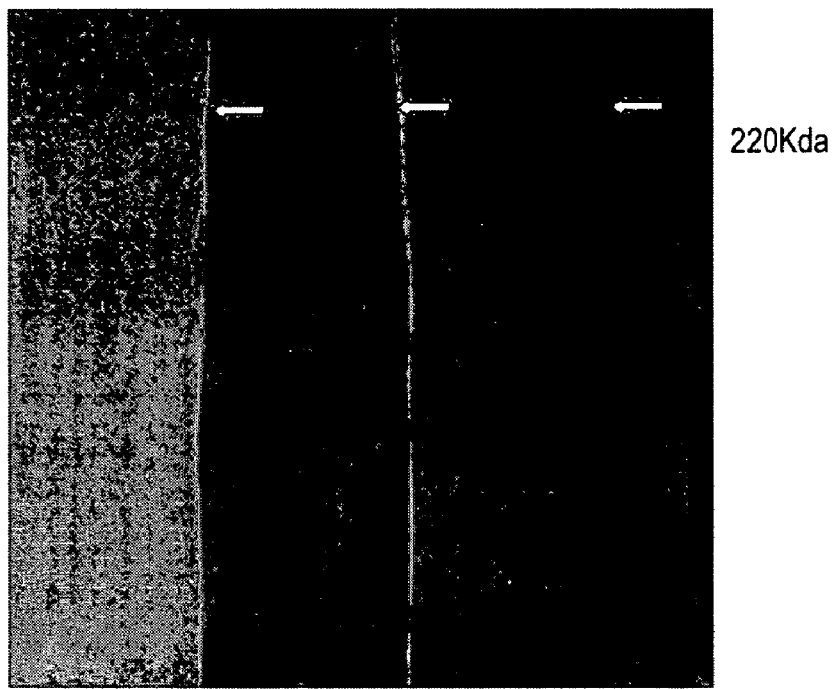
FIG. 6 is a photograph of a membrane filter which shows the result of detection of lacZ-V5 fusion protein (lacZ-V5 proteins) and mouse KIAA0620—V5 fusion protein (mKIAA0620-cds-V5 protein) which are generated in host HEK293 cells detected by Western blot with use of a rabbit polyclonal antibody. In the figure, M is a high range marker, 1 is HEK293 total proteins, 2 is lacZ-V5 protein, 3 is mKIAA0620-cds-V5 protein (these 1-4 lanes were stained with anti-V5-HRP antibody); 4 is HEK293 total proteins, 5 is lacZ-V5 protein, 6 is mKIAA0620-cds-V5 protein, 7 is HEK293 total protein, 8 is lacZ-V5 protein, 9 is mKIAA0620-cds-V5 protein (these 5-8 lanes were stained with anti-mKIAA0620 antibody). The numerical values in the figures indicate dilution factors.

On a membrane having HEK293T recombinant cells or other control recombinant cells as a starting material, a distinct single band could be detected at the position corresponding to the size of mouse KIAA0620—V5 fusion protein (about 220 kDa), in a detection system which used 500-fold or 1000-fold diluted purified rabbit polyclonal antibody (anti-mKIAA0620 antibody) as above. Into the recombinant cells, the expression vector which expresses fusion protein of mouse KIAA0620 protein and V5 protein was introduced. However several bands were detected at additional positions other than the position corresponding to 220 kDa. It could not be confirmed in this experiment whether those bands were attributable to mouse KIAA0620—V5 fusion protein. Since mouse KIAA0620 comprises a transmembrane region, the region might have not been solubilized sufficiently during sample preparation and remained to the membrane fraction. This region might have been detected as apparently less content than several bands of low molecular weight. Based on the result, it was determined that the polyclonal antibody thus prepared reacted with target mKIAA0620 fusion protein, and that the polyclonal antibody (anti-mKIAA0620 antibody) was useful for detection of mKIAA0620 protein amino acid sequence. The above result was summarized in FIG. 6.

Figure 7:
FIG. 7 is a microscopy photograph that shows the result of detection of mouse KIAA0620 gene expression in the retinal blood vessels of a neonatal mouse detected by the in situ hybridization method (left: two days after the birth, central: four days after the birth, right: seven days after the birth. Deeply stained sites can be identified along the newly generated vessels).

(8) Temporal/Spatial Identification of Mouse KIAA0620 Gene Expression in Retinal Blood Vessels of Neonatal Mouse According to In Situ Hybridization Method Temporal/spatial expression of mKIAA0620 gene at mRNA level in retinal blood vessels of a mouse fetus was analyzed. The experiment was designed as follows. A forward primer sequence was defined as 5'-CCCCGGAACTTGAACGTGTC-3' (SEQ ID NO: 3), and a reverse primer sequence was defined as 5'-CCACCTGTTCAAACTTGTGCTG-3' (SEQ ID NO: 4). With use of these primers, the transcription product of mouse mpf00920 gene was amplified by PCR, and DNA fragments of about 1,069 bps which served as either an antisense probe or an sense probe could be generated. The target PCR products, i.e., about 1,069 bps DNA fragment for an antisense probe or a sense probe was cloned to T-vector supplied by Promega. Using 1,069 bps DNA fragment cloned to T-vector as a template, an antisense cRNA probe which can detect mouse mpf00920 gene expression products and a sense cRNA probe to be used as a negative control were prepared according to the method indicated by Roche using a RNA synthetic enzyme (Roche K. K., DIG RNA Labeling Kit). Using these probes, the expression of mouse KIAA0620 gene in retina excised from a neonatal ICR mouse was observed according to the flat mount in situ hybridization of retina. On the same sample, immunostaining was conducted concurrently using an anti-mouse collagen antibody type IV (LSL Co., Ltd. Rabbit polyclonal antibody) to observe the network of vessels in retina. The expression of mouse KIAA0620 gene was confirmed along vessels. By these experiments, in developing vessels in the retina of a neonatal mouse (2 to 4 days after birth), especially in endothelium cells at leading edge of new blood vessels, intense expression was observed. On the contrary, in the retina of a mouse 7 days after birth, expression was only observed in new blood vessels in the peripheral of retina. At the center of retina in which the vessels had already been formed, the expression was significantly decreased. (FIG. 7)

(9) Putative Function of the Gene of the Invention

Based on the motif search for the polypeptide of the invention, the polypeptide had Semaphorin/CD100 antigen domain, three Plexin/Semaphorin/integrin domains, and three Cell surface receptors IPT/TIG, and a structure wherein a transmembrane (TM) segment is present at C-terminal side. The polypeptide can be considered to be novel type Plexin polypeptide derived from a rodent.

It is reported that Plexin family has 4 subfamilies; Plexin-A (type A1, type A2, type A3, type A4), Plexin-B (type B1, type B2, type B3), Plexin-C1, and Plexin-D1, and that Plexin A serves as a functional receptor for semaphorin 1a, Plexin B1 serves as a receptor for transmembrane semaphorin Sema 4D (CD00), and Plexin-C1 serves as a receptor for semaphorin Sema7A (Sema-K1) to which GPI anchors (Tamagnone L., Artigiani S., Chen H., He Z., Ming G I., Song H., Chedotal A., Winberg M L., Goodman C S., Poo M., Tessier-Lavigne M., Comoglio P M., 2001, Cell, 99: 71-80). A plexin protein belonging to Plexin family is a transmembrane protein having large molecular weight, and containing a characteristic extramembrane domain rich in cystein. Semaphorin and neuropilin are known as its receptors. Semaphorin is reported to affect on nerve axon guidance as a reaction in nerve system, and affect on development of vessels and muscle, immune reaction, angiogenesis, and growth and metastasis of tumor. Especially, Plexin-A is known to adjust nerve axon guidance of motor nerve and CNS (Central Nervous system).

The polypeptide of the invention has relatively high homology to human Plexin-D1, and has an extramembrane sema domain which is commonly found in Plexin family, MRS motif rich in cystein, and an intramembrane domain called SP domain characteristic in Plexin. The consensus sequence of MRS motif rich in cystein is C-X(5-6)-C-X(2)-C-X(6-8)-C-X(2)-C-X(3-5)-C. The sequence of the invention has one perfect MRS motif and another imperfect MRS motif. The Plexin protein having these characteristic structures plays an important role in axon guidance, morphogenesis, and phenomenon during process of disease (e.g., invasion and metastasis of tumor) (Tamagnone, L. et al., 2001, Cell, 99: 71-80). Therefore, the polypeptide of the invention is important for homeostatic control of animals in that it plays an important role in guidance necessary for angiogenesis, phenomenon associated with angiogenesis which is completed through a series of processes including vasculogenesis and construction of the vessel, and phenomenon associated with disease (e.g., invasion and metastasis of tumor). For example, in cranial nerve system, the novel Plexin polypeptide of the invention may bind to Semaphorin in cooperation with Neuropilin, or bind to VEGF in cooperation with Neuropilin during angiogenesis (document 16, 17), to adjust proliferation and differentiation of nerve and vascular endothelium via novel signal transduction system.

Based on tissue-specific expression pattern of mpf00920 gene in an adult animal, the polypeptide of the invention may be involved not only in angiogenesis during ontogenesis, but also in important cell functions in various organs. In summary, at early stage of ontogenesis, the novel Plexin polypeptide of the invention may be mainly involved in angiogenesis and differentiation, while in grown-ups, it is involved in an important role in important cell processes in a tissue having lumen structure such as gastric gland, uterine gland or renal tubule. The polypeptide may be an essential in vivo fusion protein that assumes important roles in various organs.

A probe for detecting expression of mpf00920 gene derived therefrom can specifically stain vascular endothelial cell (Flk-1 positive cells: documents 1, 10, 12, 14) during ontogenesis of a rodent. Therefore it can detect vascular endothelial cells (Flk-1 positive cell) appearing from very early stage in angiogenesis (period of proliferation and differentiation of endothelial cells). During next stage of angiogenesis (period of morphogenesis and differentiation into artery and vein of endothelial cell), constituting endothelial cells turns to be Flt-1 positive (Flt-1 positive cell: document 1, 10). In this stage, the gene of the invention is expressed as well. Since the polypeptide encoded by the gene of the invention has a structure of a cell membrane receptor, a ligand binding thereto may be a novel vascular-inducing factor. The polypeptide and its corresponding antibody may be used as a tool to search a putative vascular-inducing factor.

Until now, novel DNA which relates to human KIAA0620 gene and encodes Plexin-like polypeptide has not been obtained from a rodent, such as a rat, or a hamster, especially a mouse. Based on the expression frequency analysis at mRNA level of the gene sequence of the invention which encodes the novel Plexin amino acid sequence, it is identified for the first time that the gene is specifically expressed in vessels through whole angiogenesis period from early stage of angiogenesis in ontogenesis. On the other hand in adults, it is intensely expressed in stratified squamous epithelium in the stomach, moderately expressed in uterus, and expressed in a variety of organs including the brain. Based on these findings, a possibility is indicated that the protein encoded by the gene of the invention is involved specifically in vessels during whole angiogenesis process from its early stage, and that the protein is involved in an important function to control proliferation and differentiation of cells in various tissues in adults.

It is obvious that the gene which encodes the novel polypeptide of the invention is characterized in that it is expressed specifically in vessels during whole angiogenesis process from its early stage, and that it is expressed in a variety of organs in adults. Also, the advantage of the invention is obvious in that the polypeptide of the invention is a novel polypeptide and useful for elucidating development and preservation of function of tissues, and systemic pathology (for example, canceration, aging, dysfunction), and for development of prophylactic, therapeutic and diagnostic agent. Another advantage is that by using recombinant protein of the invention or a transgenic mouse that expresses the recombinant protein, the protein can be used for screening of an agonist, an antagonist, and drug design.

It is anticipated that mpf00920 gene may be useful as a novel marker of vascular endothelial cells during ontogenesis of a rodent (Flk-1 positive cells: documents 1, 2, 3, 10, 12, 14), or cells on the way of differentiation from a precursor to a mature vascular endothelial cell, and that the ligand binding thereto may be a novel vascular-inducing factor based on the finding that the polypeptide encoded by the gene has a cell membrane receptor structure. Therefore, the polypeptide or its corresponding antibody may be useful as a tool for detecting anticipated vascular-inducing factor.

Although no finding is available in regard to expression of human KIAA0620 gene in human at mRNA level, it is reported that mRNA which hybridizes with the gene is expressed in vascular endothelial cells or CNS during development process of a mouse (van der Zwaag, B. et al., Dev. Dyn., 2002, 225: 336-343). Mpf00920 gene of the invention is expressed specifically in vessels for whole period of angiogenesis from its early stage in ontogenesis. In an adult, it is intensely expressed in stratified squamous epithelium of a stomach, moderately expressed in uterus, and expressed in a various organs including the brain. Therefore, the gene may be used to elucidate mechanism of development and preservation of function of organs, aging, dysfunction, congenital abnormality, and a disease in an organ in which angiogenesis is involved. It also may be useful to develop diagnostic, therapeutic and test drug of the disease as above. The recombinant protein or a recombinant cell according to the invention may be used for screening of an agonist and an antagonist, and for drug-design.

The gene which relates to human KIAA0620 gene which encodes Plexin-like polypeptide that is crucially important in proliferation, differentiation or aging of vascular endothelium, and derived from a rodent including a rat, a mouse, or a hamster, may be a causative gene of disease. It can be easily anticipated that Plexin-like polypeptide of the invention may be a cause of diseases as follows.

For example, the polypeptide is suspected to be involved in pathologic processes in which angiogenesis plays some role (e.g., healing of wound, healing of fracture, vascular occlusion and collateral vessel formation); processes in which angiogenesis plays some undesirable role such as proliferation of cancer cells, chronic articular rheumatism, diabetic retinopathy, endometriosis, obesity; and processes in which angiogenesis plays some desirable role such as heart attack, neurodegenerative diseases, circulatory disorder in legs, arteriosclerosis obliterans, and psoriasis vulgaris.

The amino acid sequence of the polypeptide of mouse mKIAA0620 of the invention, a nucleic acid sequence which encodes the amino acid sequence, and an antibody which specifically binds to the amino acid sequence may be applied to various medical fields in which angiogenesis is involved in pathologic condition. They can be used for development of an angiogenesis control factor or agent, and a differentiation control factor or agent, in following processes: processes in which normal angiogenesis in adults is involved such as healing of wound, healing of fracture, vascular occlusion and collateral vessel formation, periodic formation of vascular network in tunica mucosa uteri (transient or at the time of luteinization); processes in which angiogenesis is undesirably involved such as proliferation of cancer cells, chronic articular rheumatism, diabetic retinopathy, endometriosis, obesity; and processes in which angiogenesis is desirably involved such as heart attack, neurodegenerative diseases, circulatory disorder in legs, arteriosclerosis obliterans, and psoriasis vulgaris (documents 1, 4, 5, 7, 11). Particularly, the polypeptide is anticipated to be involved in angiogenesis in tumor tissue during proliferation of cancer cells. Therefore, if an inhibitory growth factor or agent which can specifically inhibit angiogenesis is identified with use of a tool which may be available based on the invention, it may be used as anticancer drug. Such inhibitory factor includes a various inhibitory growth factors which are generated in vivo and can inhibit proliferation of solid cancer including endostatin and angiostatin (document 6, 7), a blocker of receptor, a monoclonal antibody binding to extracellular binding site. In regeneration medicine, the polypeptide of the invention can be used in a novel screening system to screen a protein or an antibody used for isolation of angioblasts, a growth factor and an inhibitory growth factor involved in proliferation of isolated angioblasts (documents 1, 2, 3, 14).

With use of amino acid sequence of mouse mKIAA0620 polypeptide of the invention which has homology to human KIAA0620 protein or Plexin family D1, a nucleic acid sequence which encodes the amino acid sequence, and an antibody which specifically binds to the amino acid sequence, it is possible to device a screening method and a measurement kit which uses the target gene or gene products derived form a rodent such as a mouse, for screening and measurement of a vascular proliferation and differentiation control factor or compound. In other words, it is possible to produce interaction detection system and an agonist, antagonist, in vivo ligand detection system using the recombinant protein. Furthermore, by producing transgenic cells and animals, an in vitro or in vivo model of disease can be produced and it can be used for evaluation of a compound that controls the expression of the gene, and for studies on vascular cell proliferation and differentiation control, and for studies on inhibition of vascular proliferation which undesirably supports proliferation of cancer cells. Also, the invention has an advantage in that it may be used for screening of an agonist and an antagonist, and drug design study with recombinant cells, and an animal model of disease such as a mouse. The invention has another advantage in that it may be useful for elucidating the mechanism to control vascular cell proliferation and differentiation, the mechanism to inhibit vascular proliferation, by using the amino acid sequence of the polypeptide of the invention, a nucleic acid sequence which encodes the amino acid sequence, and an antibody which specifically binds to the amino acid sequence. The invention has yet another advantage in that that may be useful in development of prophylactic, therapeutic and diagnostic medicine for disease in which the above mechanism is involved.

(10)

Compulsive Expression of Full-Length Polypeptide of KIAA0620 or its Extramembrane region by recombinant Cell As described in the paragraph 0079, from a search using a ETAIVVSIVICSVLLLLSVVALF (SEQ ID NO. 22) was found in the 1,090th to the 1,112nd amino acid from N-terminal in the amino acid sequence represented by SEQ ID NO: 1 (the 1,341st to the 1,363rd amino acid in the sequence represented by SEQ ID NO: 15). It was anticipated that the polypeptide of the invention may be a membrane protein because it has a transmembrane (TM) segment. This anticipation was confirmed by following experiment.

First, a compulsive expression vector of full-length mouse KIAA0620 and V5 fusion protein was constructed using a mammalian cell as a host. Particularly, as indicated in the paragraph 1110, a forward primer was defined as CAC-Catgggctgtgggcgtggtct (SEQ ID NO: 12, 24 bps. A 24 bps sequence including 20 bps from the sixth to 25th base in the sequence represented by SEQ ID NO: 16), and a reverse primer 2 was defined as GGCCTCGCTGTAACACT-CATAGA (SEQ NO: 14, 23 bps. A sequence complementary to 23 bps sequence from the 5,218th to the 5,240th base in a sequence represented by SEQ ID NO: 2, not including a stop codon. Alternatively, 23 bps sequence from the 5,971st to the 5,993rd base in the sequence represented by SEQ ID NO: 15). Using these primers, entry clones were prepared. Entry clones were transformed to an expression destination vector (pcDNA-DEST40 vector, pEF5/FRT/V5-DEST vector. Former is a plasmid vector expressed under the control of CMV promoter and the latter is a plasmid vector expressed under the control of EF-1α promoter) to construct a compulsive expression vector, by a site specific recombination reaction using LR Clonase enzyme mix (Invitrogen: Cat. NO. 11791-019). The compulsive expression vector which encodes full-length mouse KIAA 0620—V5 fusion protein, that is, an amino acid sequence (the 2nd to the 1997th amino acid (1,996 amino acids) on the N-terminal side of the sequence represented by SEQ ID NO: 15, excluding the 1st Glu) to which 250 amino acid sequence (the 2nd to the 251st amino acid (250 amino acids) on the N-terminal side of the sequence represented by SEQ ID NO: 11, excluding the 1st Glu) was added to the N-terminal of the polypeptide of the invention represented by SEQ ID NO: 1, was constructed using mammalian cell as a host.

Next, a compulsive expression vector which encodes mouse KIAA0620 extramembrane region(TM)—V5 fusion protein, that is, a polypeptide containing an extramembrane region and a transmembrane region comprising the 2nd to the 1,363rd amino acid (1,362 amino acids) in the sequence represented by SEQ ID NO: 15 was constructed in a similar manner using mammalian cells as a host. Particularly, entry clone was transformed to an expression destination vector (pcDNA-DEST40 vector, pEF5/FRT/V5-DEST vector.

Former is a plasmid vector expressed under the control of CMV promoter and the latter is a plasmid vector expressed under the control of EF-1α promoter), by a site specific recombination reaction using LR Clonase enzyme mix (Invitrogen: Cat. NO. 11791-019).

The plasmid vector which expresses mouse KIAA0620 full-length—V5 fusion protein and the plasmid vector which expresses mouse KIAA0620 extramembrane region (TM)—V5 fusion protein thus constructed (both of them were derived from pEF5/FRT/V5-DEST (Invitrogen), an expression vector for Flp-ln, by cloning the target gene) were introduced in kidney cells derived from human fetus (HEK293T cell) to produce transgenic cells which compulsively express either KIAA0620 full-length polypeptide or extramembrane region thereof.

With use of a 6 well plate filled with DMEM medium containing 10% fetal bovine serum, and as gas phase air containing 5% $CO_2$ saturated with moisture, HEK294 host cells were cultured until reaching to subconfluent, in a carbon dioxide incubator in which the temperature was kept at 37° C. Next, transfection solution 3 μL (FuGENE6 transfection Reagent solution supplied by Roche) and plasmid vector 2 μg which expresses mouse KIAA0620 full-length—V5 fusion protein was added to 2 wells, and the transfection solution 3 μL and plasmid vector 2 μg which expresses mouse KIAA0620 extramembrane region (TM)—V5 fusion protein was added to another 2 wells, for transformation. Remaining 2 wells were used as controls, that is, transfection solution without plasmid vector (FuGENE6 Transfection Reagent solution) was added. Then culture was continued.

After transfection, cells were collected from total 6 wells which had been cultured for two days. From these cells, proteins were collected using two different methods. In order to prepare whole protein, the culture was solubilized using a conventional method using SDS sample buffer. From 3 wells in 6 wells, whole protein derived from each cell was obtained.

Next, using Mem-PER Eukaryote Membrane protein Extraction Kit supplied by PIERCE biotechnology Inc., whole protein was prepared according to the condition indicated by the PIERCE. From the whole protein as a material, hydrophobic fraction of the protein was isolated and extracted. By above procedures, whole protein derived from different cells in 3 wells, and whole protein and membrane protein fraction derived from different cells in 3 wells using membrane protein fraction kit supplied by PIERCE biotechnology Inc., were obtained. The protein fractions derived from recombinant cells transformed by the expression vector which expresses mouse KIAA0620 full-length—V5 fusion protein, that derived from recombinant cells transformed by the expression vector which expresses mouse KIAA0620 extramembrane region (TM)—V5 fusion protein, and that derived from the control cells were size-fractioned by SDS-polyacrylamide electrophoresis, as described in above (7-2). By chemiluminescence using anti-V5 monoclonal antibody which recognizes V5 tag (Invitrogen; V5-HRP, R961-25, or V5, R960-25) and ECL kit (Amersham), or by Western blotting using conventional luminescence using these antibodies, the target recombinant protein was detected. For the control cells, the recombinant protein of interest could not be detected either in whole protein fraction derived from the cells, whole protein fraction and membrane protein fraction obtained by membrane protein fraction kit supplied from PIERCE biotechnology Inc. On the other hand, bands were detected around about 200 kDa or 140 kDa of interest in whole protein fraction derived from the recombinant cells transformed by the expression vector which expresses mouse KIAA0620 full-length—V5 fusion protein, and in whole protein fraction derived from the recombinant cells transformed by the expression vector which expresses mouse KIAA0620 extramembrane region (TM)—V5 fusion protein. For whole protein fraction obtained by membrane protein fraction kit supplied by PIERCE, a weak band was detected around about 200 kDa for the recombinant cells transformed by the expression vector which expresses mouse KIAA620 full-length—V5 fusion protein, and a weak band was detected around about 140 kDa for the recombinant cells transformed by the expression vector which expresses mouse KIAA 0620 extramembrane region (TM)—V5 protein.

On the whole protein fraction obtained using Mem-PER Eukaryote Membrane protein Extraction Kit supplied by PIERCE, and the hydrophobic protein fraction which was isolated therefrom, detection experiment using Western blotting as above was conducted after the protein in the solution was concentrated by additional concentration process using ultra-filtration, using various cells prepared in similar method as above. As a result, for the control cells, the recombinant protein could not be detected either in the whole protein fraction, or the hydrophobic protein fraction which was separated and prepared therefrom. On the other hand, in the whole protein fraction derived from the recombinant cells transformed by the expression vector which expresses mouse KIAA0620 full-length—V5 fusion protein, a distinct band was detected around 200 kDa of interest. In a hydrophobic protein fraction separated and prepared from the whole protein fraction, a weak band was detected around 200 kDa. In the whole protein fraction derived from the recombinant cells transformed by the expression vector which expresses mouse KIAA0620 extramembrane (TM)—V5 fusion protein containing mouse extramembrane region and transmembrane region (TM), a distinct band was detected around 140 kDa. In the hydrophobic protein fraction separated from the whole protein fraction, a weak band was detected around 140 kDa.

Figure 8A:
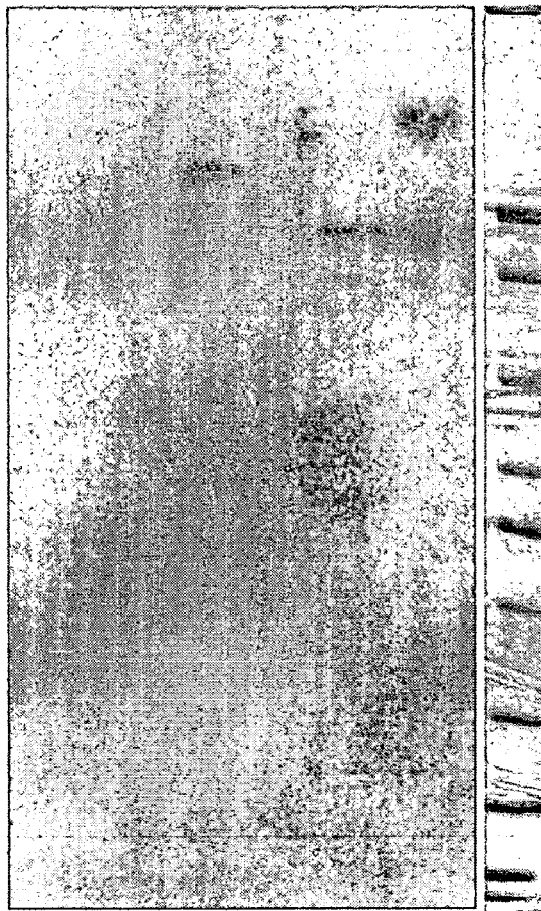
FIG. 8A is an image obtained by color development, that on the right.
Figure 8B:
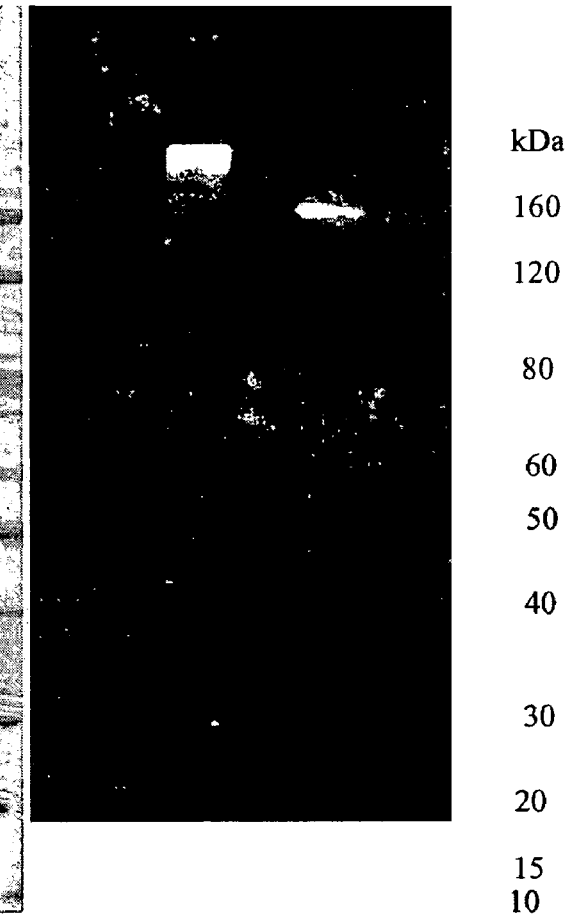
FIG. 8B is an image obtained by chemiluminescence, and the ladder and numerical values in the center indicate the size marker and molecular weight (kDa) represented by the marker.

Mouse KIAA0620 full-length—V5 fusion protein was detected in the whole protein fraction and the hydrophobic protein fraction. Thus, it was confirmed that KIAA0620 protein comprises a functional transmembrane (TM) segment and located in membrane as a membrane protein. As the synthetic polypeptide prepared as a recombinant protein containing the extramembrane and transmembrane (TM) regions comprises transmembrane (TM) region, it was detected in the whole protein fraction and the hydrophobic protein fraction as expected. Under the condition to separate hydrophobic protein and hydrophilic protein using a solvent specified in Mem-PER Eukaryote Membrane protein Extraction Kit supplied by PIERCE, the polypeptide of the invention was not definitely separated into hydrophobic fraction despite that it contained one transmembrane region (TM). However from the above result, it was confirmed that the expression vector which expresses mouse KIAA0620 full-length—V5 fusion protein and the expression vector which expresses mouse KIAA0620 extramembrane region (TM)—V5 fusion protein generated recombinant protein using mammalian cells as a host, and that mouse KIAA0620 full-length—V5 fusion protein was present in the hydrophobic protein fraction. The above result is shown in FIG. 8.

(11)

Compulsive Expression of KIAA0620 Full-Length Polypeptide and Extramembrane Region Using Recombinant Cells As described in above (10), entry clones were transformed to an expression destination vector (pcDNA-DEST40 vector, pEF5/FRT/V5-DEST vector. Former is a plasmid vector expressed under the control of CMV promoter and the latter is a plasmid vector expressed under the control of EF-1α promoter), by site-specific recombination reaction using LR Clonase enzyme mix (Invitrogen: Cat. NO. 11791-019). Compulsive expression vectors in mammalian cells were constructed for mouse KIAA0620 full-length native protein, mouse KIAA0620 full-length—V5 fusion protein, mouse KIAA0620 extramembrane region—V5 fusion protein, mouse KIAA0620 full-length-GFP fusion protein, mouse KIAA0620 extramembrane region—GFP fusion protein, mouse KIAA0620 full-length—DsRed fusion protein, mouse KIAA0620 extramembrane region—DsRed fusion protein, mouse KIAA0620 full-length—human IgGIFc fraction fusion protein, and mouse KIAA0620 extramembrane region—human IgGIFc fraction fusion protein. These vectors were introduced into kidney cells derived from human fetus (HEK293 cell) using Transfection reagent (Fugene 6; Roche) and transgenic cells were prepared. By using these cells, the expression of fusion proteins was confirmed in the following experiments.

First, on a membrane having HEK293 recombinant cells or other recombinant cells as a starting material, a detection experiment according to the Western blotting using anti-V5-HRP antibody was conducted, as described in (10). Into the recombinant cells, the expression vector that expresses mouse KIAA0620 full-length—V5 fusion protein or the expression vector that expresses mouse KIAA0620 extramembrane region—V5 fusion protein was introduced. By anti-V5-HRP antibody, distinct single band was detected at the position corresponding to the size (about 200 kDa) of mouse KIAA0620 full-length—V5 fusion protein, or the size (about 140 kDa) of KIAA0620 extramembrane region—V5 fusion protein. Based on the finding that the molecular weight of the detected band corresponded to the theoretical molecular weight of the fusion protein of mouse KIAA0620 full-length protein or mouse kIAA0620 extramembrane region, it could be confirmed that the mouse KIAA0620 full-length protein or mouse KIAA0620 extramembrane region protein was expressed as a V5 fusion protein.

On a membrane having HEK293 recombinant cells or other recombinant cells as a starting material, a detection experiment according to the Western blotting using one of anti-GFP mouse monoclonal antibody (Nacalai tesque Part No: 04363-24), anti-DsRed rabbit polyclonal antibody (BD Biosciences Clontech Co., Ltd., Part No: 632397), or anti-human IgG1Fc mouse monoclonal antibody (CHEMICON International Inc., Part No: MAB1302) was conducted in the same manner. Into the recombinant cells, the expression vectors that respectively express one of fusion proteins of mouse KIAA0620 full-length and GFP, DsRed or human IgGIFc fraction, or fusion proteins of mouse KIAA0620 extramembrane region and GFP, DsRed or human IgGIFc fraction were introduced. By these antibodies, distinct single band was detected at the positions corresponding to the size of corresponding fusion proteins. Based on the finding that the molecular weight of the detected bands corresponded to the theoretical molecular weight of the fusion protein of mouse KIAA0620 full-length or mouse KIAA0620 extramembrane region and proteins as above, it could be confirmed that the mouse KIAA0620 full-length protein or mouse KIAA0620 extramembrane region protein was expressed as a fusion protein having respective tag.

(12)

Production of Gene Strain which Shows Stable Expression

Plasmid vectors which express mouse KIAA0620 full-length—GFP fusion protein or mouse KIAA0620 extramembrane region—GFP fusion protein (expression vector for Flp-In derived form pEF5/FRT/V5-DEST supplied by Invitrogen, by cloning the target gene), and plasmid vectors which express mouse KIAA0620 full-length—DsRed fusion protein or mouse KIAA0620 extramembrane region—DsRed fusion protein (expression vector for Flp-In derived form pEF5/FRT/V5-DEST supplied by Invitrogen, by cloning the target gene), were introduced in Flp-in expression system supplied by Invitrogen, into kidney cells derived from human fetus (HEK293 cell) to produce transgenic strains which compulsively and stably express the KIAA0620 full-length polypeptide or extramembrane region thereof.

With use of a 6 well plate filled with DMEM medium containing 10% fetal bovine serum, and as gas phase air containing 5% $CO_2$ saturated with moisture, HEK294 host cells were cultured until reaching to subconfluent in carbon dioxide incubator in which temperature was kept at 37° C. Culture was continued until when the HEK293 host cells (Flp-in-293 cells by Invitrogen. Derived from 293 Human embryonic kidney cells and has single Flp recombinase target site (FRT site) at the position in the genome to be transferred) reached to subconfluent.

Next, transfection solution 3 μL (FuGENE6 Transfection Reagent solution supplied by Roche) and plasmid vector 2 μg which expresses mouse KIAA0620 full-length—GFP fusion protein was added to 2 wells, and the transfection solution 3 μL and plasmid vector 2 μg which expresses mouse KIAA0620 extramembrane region (TM)—GFP fusion protein was added to another 2 wells, for transformation. Remaining 2 wells were used as controls, that is, transfection solution without plasmid vector (FuGENE6 Transfection Reagent solution) was added. As to fusion protein with DsRed, similar procedures were conducted. Then culture was continued.

After transformation, culture for 2 days, and culture for 10 days under selective force using Hygromycin B selective medium (200/microg/ml) was conducted. Transformed cells grown in wells were sorted by FACS to select those indicated color of luminescent fusion protein (GFP or Ds Red), to establish a stable strain by collecting cells that showed stable expression of introduced gene.

(13)

Analysis of Polypeptide Function of the Invention in Angiogenesis in the Retina of a Neonatal Mouse Using Mouse KIAA620 Protein Extramembrane Region—IgG1Fc Fusion Protein The extramembrane region polypeptide having 1,337 amino acids (identical to the sequence from the 2nd to the 1,338 amino acid in the sequence represented by SEQ ID NO: 15) was fused to human IgG1Fc fragment region using gene recombination method, and a plasmid vector which expresses the product of this gene under the control of CAG promoter. The plasmid vector was introduced to 293T cells using Trans IT-LT1 Transfection Reagents supplied by Mirus Bio Corporation. The resultant cells were cultured for 3 days in a serum free medium INVITROGEN™(GibcoCD293) The culture was applied to Protein G column HI TRAP™ Protein G HP, Amersham Biosciences) to purify mouse KIAA0620 extramembrane region—IgG1Fc fusion protein from the supernatant of the culture.

500 nl of the fusion protein solution thus obtained (2.3 mg/1 ml in phosphoric acidbuffer) was injected into the eyeballs of a neonatal ICR mouse (1, 3, or 5 days after birth) using a micro injector incorporating glass capillary (Drummond Co., Ltd., NANOJECT II, Drummond Scientific Co., Broomall, Pa., USA). As a control, a sample was prepared by injecting human IgG1Fc fragment (Jackson ImmunoResearch Laboratories, West Grove, Pa., USA) of same concentration into the eyeballs in same manner. Any change in the blood vessels in retina of both samples was observed according to the retina flat mount luminescence stain method using anti-mouse PECAM-1 monoclonal antibody (BD Pharmingen, Mec 13.3). For observation, Axioplan 2 luminescence microscope and Axiovision 3.0 software (Carl Zeiss Co., Ltd., Oberkochen, Germany), were used. For observation of images using confocal microscope system, Axiovert 200M laser microscope and LSM510-V3.2 software (Carl Zeiss Co., Ltd., Oberkochen, Germany), were used.

As a result, five hours after the injection into the eyeball, excessive formation of filopodium was observed in the developing blood vessels of retina, especially in the endothelial cells at the leading edge of angiogenesis (FIG. 9). 2 to 3 days after the injection (FIG. 10), normal construction of the blood vessel network in the retina was significantly obstructed. On the contrary, no change was observed in the negative control wherein only IgG1Fc protein was injected to the eyeballs. (FIG. 9, FIG. 10)

INDUSTRIAL APPLICATION

Based on the above description, the DNA, the polypeptide, or the antibody of the invention, can be considered to be essential in angiogenesis, and development and conservation of functions in various organs including the brain. It also is a key to elucidate mechanism of human diseases in which angiogenesis is involved such as aging, dysfunction, congenital abnormality, and to develop diagnosis, treatment, preservation and prevention of diseases in various organs. The expression pattern information obtained from expression frequency analysis at mRNA level in each tissue and development stage indicated that the gene is expressed ubiquitously in various organs. This implies that the gene of the invention is essential in development, differentiation, preservation of function and aging of organs.

Therefore, the DNA of the invention, the gene which contains the DNA and is derived from a rodent, full-length or a part of the polypeptide encoded by the DNA, the antibody against the full-length or a part of the polypeptide, and antisense DNA can be used as a therapeutic or diagnostic medicine in the development of treatment and prevention of various diseases using a mouse which is a model animal for human disease including cancer and congenital abnormality.

What is claimed is:

1. An isolated polypeptide comprising the full length of amino acid sequence of SEQ ID NO: 18.

2. An isolated polypeptide according to claim 1, wherein the polypeptide is recombinantly produced.

3. A polypeptide binding kit comprising the polypeptide according to claim 1 or 2.

4. A composition comprising the polypeptide according to claim 1 or 2 as an active ingredient, and a pharmaceutically acceptable carrier.

5. A method of inhibiting angiogenesis which comprises contacting a vascular cell with an isolated polypeptide of claim 1 or 2.

* * * * *